United States Patent [19]

Hibino et al.

[11] Patent Number: 4,982,725
[45] Date of Patent: Jan. 8, 1991

[54] ENDOSCOPE APPARATUS

[75] Inventors: Hiroki Hibino; Yoshikatsu Nagayama; Mutsumi Yoshikawa, all of Hachioji; Toshiyuki Takara, Higashimurayama; Masahito Goto; Akira Suzuki, both of Hachioji; Sakae Takehana, Machida; Yoshinao Oaki, Hachioji; Koichi Yoshimitsu, Hachioji; Yoshisada Aoki, Hachioji, all of Japan

[73] Assignee: Olympus Optical Co., Ltd., Tokyo, Japan

[21] Appl. No.: 535,216

[22] Filed: Jun. 8, 1990

[30] Foreign Application Priority Data

Jul. 4, 1989 [JP] Japan .................................. 1-173604
Sep. 5, 1989 [JP] Japan .................................. 1-230234
Mar. 30, 1990 [JP] Japan .................................. 2-86178

[51] Int. Cl.$^5$ .............................................. A61B 1/00
[52] U.S. Cl. ...................................................... 128/4
[58] Field of Search .......................... 128/4, 6; 358/98

[56] References Cited

U.S. PATENT DOCUMENTS 4,292,961 10/1981 Kawashima ............................ 128/6
4,559,928 12/1985 Takayama .............................. 128/6

FOREIGN PATENT DOCUMENTS 53-39685 4/1978 Japan .
59-57906 4/1984 Japan .
61-87530 5/1986 Japan .
63-252128 10/1988 Japan .

Primary Examiner—William H. Grieb
Attorney, Agent, or Firm—Armstrong, Nikaido, Marmelstein, Kubovcik & Murray

[57] ABSTRACT

The endoscope apparatus comprises an endoscope having an elongate insertable part having a bendable part and a driving apparatus for bending and driving the bendable part, a first bending controlling apparatus for controlling the driving apparatus and a second bending controlling apparatus for controlling the driving apparatus independently of the first bending controlling apparatus when the first bending controlling apparatus is controllable.

38 Claims, 36 Drawing Sheets

FIG.14 (A)     FIG.14 (B)
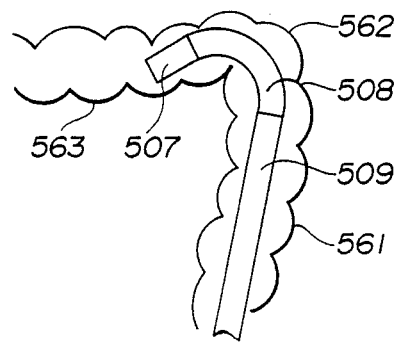
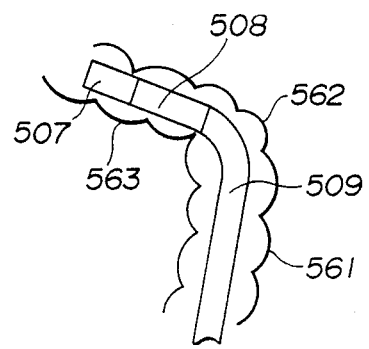
FIG.15
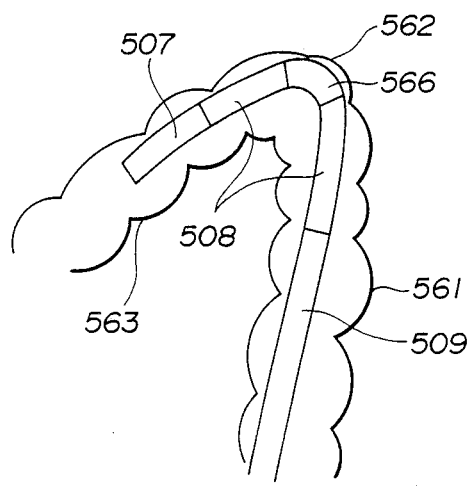

ENDOSCOPE APPARATUS

BACKGROUND OF THE INVENTION

1. Field of the Invention:

This invention relates to an endoscope apparatus provided with an endoscope having a driving means for bending a bendable part with a motor.

2. Related Art Statement

There is already extensively used an endoscope (scope or fiber scrope) whereby, by inserting an elongate insertable part into a body cavity, organs within the body cavity can be diagnosed or inspected. It is used for not only medical but also industrial uses in observing or inspecting objects within a pipe of a boiler, machine or chemical plant or within a machine.

Further, there are used various endoscopes using such solid state imaging device as a charge coupled device (CCD) for the imaging means.

There is recently suggested an endoscope wherein a motor is used for a driving means for a bending operation of bending, for example, vertically/horizontally a bendable part provided in an insertable part of the above mentioned endoscope.

However, if the operation of bending the insertable part is thus electrically made, in the case of the bending operation, the bent state of the insertable part and the size of the load then will not be easily felt by hand. Therefore, there has been a problem that the insertable part will be bent more than is required within the body cavity and will contact at the tip with the body cavity wall or the like so strongly as to hurt it in the worst case.

An endoscope apparatus provided with a means for solving the above described problem is suggested, for example, in the publication of Japanese patent application laid open No. 87530/1986.

However, in the above described endoscope apparatus, in case the insertable part strongly contacts at the tip with the body cavity wall or the like, the bending will only stop but the problem that the danger of hurting the body cavity wall or the like will not be able to be avoided will still remain.

Also, in the case of inserting the insertable part, for example, of a medical endoscope through, for example, a spleen bent part of a large bending angle in the large intestine, if the insertable part is only pushed in, the insertable part on the tip side will only push the body cavity wall in the spleen bent part, it will be difficult to insert the insertable part and further the insertable part on the tip side will be Pushed back by the body cavity wall in some case.

In order to advance the insertable part in the above described state, it is necessary to make the bending angle of the bendable part substantially straighrt and at the same time to make an operation of pushing in the insertable part and there is a problem that the operation requires a skill.

As a means of solving such problems, for example, the pesent applicant suggests to make the bending angle of the bendable part substantially straight by using an elastic sheath for the bendable part to utilize the elasticity of this sheath as shown in the publication of Japanese patent application laid open No. 252128/1988.

However, in the endoscope using a motor for the driving means for bending the bendable part, in case the lever of a bending switch is placed in a neutral position, the bendable part will act to be fixed as bent in a predetermined direction, therefore there will be problems that, in order to make the bending angle a predetermined angle, for example, substantially straight, the lever will have to be operated to bend the bendable part in the direction reverse to the bending direction and that the direction will be missed during the operation and the operation will be complicated.

Further, in such endoscope having a motor as is described above, in case a momentary switch is used for the above mentioned bending switch, the operator will not be able to easily recognize the bending angle of the above mentioned bendable part and, even if a bending angle displaying means for displaying the bending angle is provided, the bending direction, for example, for making the bendable part substantially straight will have to be judged at a moment from the bending angle displayed by the bending angle displaying means and there is a problem that a skill is required.

OBJECT AND SUMMARY OF THE INVENTION

An object of the present invention is to provide an endoscope apparatus whereby, in order to make a safe and quick inspection, in case the insertable part is bent and contacts an object to be inspected, this contact state will be able to be avoided.

Another object of the present invention is to provide an endoscope apparatus whereby, in order to make an accurate and quick inspection, in case the above mentioned insertable part is bent and the bending direction is missed, the insertable part will be able to be bent in a predetermined angle so as to be able to be easily inserted by such control as an automatic control or switching.

A further object of the present invention is to provide an endoscope apparatus whereby, in case the insertable part is bent to contact an inspected object during the insertion, the contact state will be prior avoided even during the bending operation and the bending angle will be kept in a predetermined shape by such control as by switching a switch.

An object of the pesent invention is to provide an endoscope apparatus whereby, in order to avoid the contact state of the insertable part with an inspected object or to make a predetermined bending angle, in consideration of the safety, the insertable part is bent quicker or, on the contrary, slower than an ordinary bending operation so as to control the bending operation at a speed adapted to the state.

Another object of the present invention is to provide an endoscope apparatus whereby, as connected with the endoscope by a connecting means connectable with an endoscope having a bending resistance detecting means, by the result of the detection by the bending resistance detecting means, the bending part of the endoscope is driven or the bending driving part provided within the endoscope is controlled so as to reduce the bending resistance to be lower than a predetermined bending resistance value.

The endoscope apparatus of the present invention comprises an endoscope having an elongate insertable part having a bendable part which can be bent and a driving means for bending and driving the above mentioned bendable part, a first bending controlling means for controlling the above mentioned driving means and a second bending controlling means for controlling the above mentioned driving means independently of the above mentioned first bending controlling means when the above mentioned first bending controlling means is controllable.

The endoscope apparatus of the present invention further comprises a bending resistance detecting means for detecting the bending resistance, for example, of the insertable part.

The endoscope apparatus of the present invention comprises also a switching means for controlling, for example, the second bending controlling means.

The second bending controlling means is provided with a means for controlling the bendable part to be of a bending angle, for example, with a predetermined time.

The other features and advantages of the present invention will become apparent enough with the following explanation.

BRIEF DESCRIPTION OF THE DRAWINGS

FIG. 1 is a block diagram showing an endoscope apparatus.

FIG. 2 is a circuit diagram showing a concrete formation of a bending switch controlling circuit.

FIG. 3 is a circuit diagram showing a concrete formation of a contact pressure detecting circuit.

FIG. 4 is a circuit diagram showing a concrete formation of a USM controlling circuit.

FIG. 5 is a circuit diagram showing a concrete formation of a USM controlling circuit.

FIG. 6 is a concrete formation diagram of a USM controlling circuit.

FIG. 7 is a sectioned view of an essential part of a USM.

FIG. 8 is a time chart showing an operation of a USM controlling circuit.

FIG. 9 is a formation diagram of a USM controlling circuit.

FIG. 10 is a formation diagram of a bending motor controlling circuit.

FIGS. 12 to 14 relate to the sixth embodiment of the present invention.

FIG. 12 is a block diagram showing a formation of an endoscope apparatus.

FIG. 13 is a block diagram showing a formation of an ultrasonic motor controlling circuit.

FIGS. 14(A) and 14(B) are explanatory views of an insertable part inserted into a spleen bent part.

FIG. 15 relates to the seventh embodiment of the present invention.

FIG. 15 is an explanatory view of an endoscope as inserted at the tip into a spleen bent part.

FIG. 16 is an explanatory view showing a formation of an endoscope apparatus.

FIG. 17 is an explanatory view showing a formation of an endoscope apparatus.

FIG. 18 is an explanatory view showing a formation of an endoscope apparatus.

FIG. 19 is an explanatory view of a bending controlling method.

FIG. 20 is an explanatory view of an endoscope apparatus.

FIG. 21 is a block diagram of a bending resistance notifying means.

FIG. 22 is an explanatory view of an endoscope apparatus.

FIG. 23 is a block diagram of a motor abnormal operation notifying means.

FIG. 24 is an explanatory view of an endoscope apparatus.

FIG. 25 is a block diagram of a bending angle notifying means.

FIG. 26 is an explanatory view of a joy stick type bending switch.

FIG. 27 is a block diagram of a bending resistance notifying means.

FIG. 28 is a block diagram of a bending resistance notifying means.

FIG. 29 is an explanatory view of a joy stick type bending switch.

FIG. 30 is a block diagram of a bending resistance notifying means.

FIG. 31 is a block diagram of a circuit for detecting and notifying the driving state of an endoscope bendable part.

FIG. 32 is a formation view of an electronic endoscope apparatus.

FIG. 33 is a sectioned view of an essential part of an ultrasonic motor.

FIG. 34 is an explanatory view of a bendable part driving mechanism.

FIG. 35 is a formation view of a bending driving circuit of an endoscope bendable part.

FIG. 36 is a block diagram of a circuit for detecting and notifying the driving state of an endoscope bendable part.

FIG. 37 is a formation view of a fiber scope.

FIG. 38 is a block diagram of a circuit for detecting and notifying the driving state of an endoscope bendable part.

FIG. 39 is a formation view of an endoscope apparatus.

FIG. 40 is an explanatory view of a means for notifying a bending resistance.

FIG. 41 is an explanatory view of a means for notifying a bending resistance.

FIG. 42 is a formation view of an electronic endoscope apparatus.

FIG. 43 is a formation view of an endoscope apparatus.

FIG. 44 is an explanatory view of a means for detcting a bending resistance.

FIG. 45 is an explanatory view of a means for notifying a bending resistance.

FIG. 46 is an explanatory view of a means for notifying a bending resistance.

FIG. 47 is an explanatory view showing the formatiion of an essential part of an endoscope apparatus.

FIG. 48 is a circuit diagram showing a driving system of a DC motor.

FIG. 49 is an explanatory view showing a tip part of an insertable part of an endoscope.

DETAILED DESCRIPTION OF THE PREFERRED EMBODIMENTS

In FIGS. 1 to 4 is shown the first embodiment of the present invention.

Figure 1:
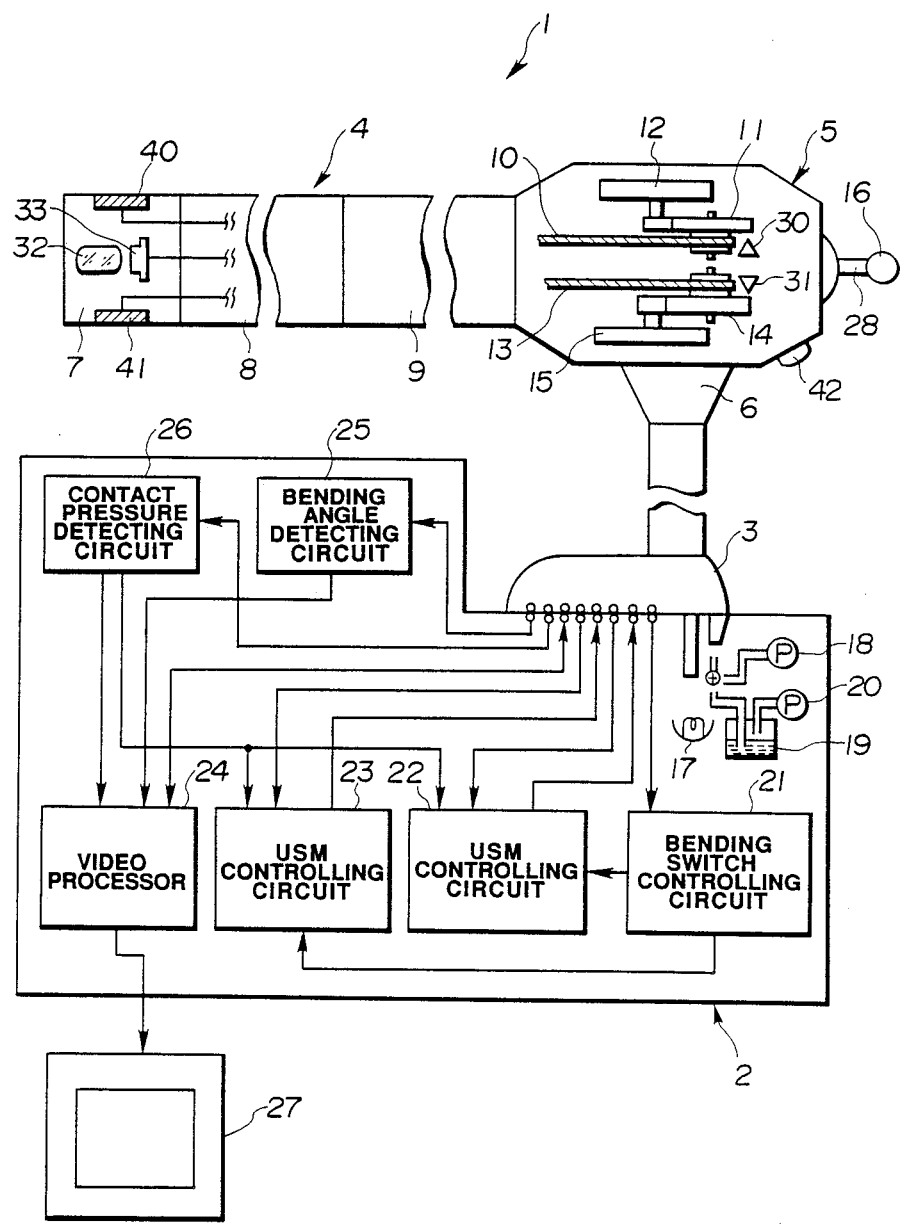
FIGS. 1 to 4 relate to the first embodiment of the present invention.

As shown in FIG. 1, an endoscope 1 is to be removably connected to a universal controlling apparatus (mentioned as a UCA hereinafter) 2 through a connector 3.

The above mentioned endoscope 1 comprises an elongate, for example, flexible insertable part 4 to be inserted into a body cavity or the like, a thick holding part 5 connected to the above mentioned insertable part 4 at the rear end, a flexible universal cable 6 extended sidewise from the above mentioned holding part 5 at the rear end and the above mentioned connector 3 provided at the tip of the above mentioned universal cable 6. The above mentioned insertable part 4 comprises a rigid tip part 7, a bendable part 8 capable of being bent and provided on the rear side adjacent to the above mentioned tip part 7 and a flexible tube part 9 provided in the rear of the abve mentioned bendable part 8.

An objective lens 32 is provided in the above mentioned tip part 7. A solid state imaging device 33 is arranged in the image forming position of the above mentioned objective lens 32. An image of an object to be imaged is to be formed on the imaging surface of the above mentioned solid state imaging device 33. Signal lines (not illustrated) are connected to the above mentioned solid state imaging device 33 and are inserted through the above mentioned universal cable 6 to transmit an image signal of the object to a video processor 24 within the above mentioned UCA 2 through the above mentioned connector 3. A contact pressure sensor 40 for detecting a contact pressure when the above mentioned bendable part 8 is bent upward to contact at the above mentioned tip part 7 with a body cavity interior or the like, a contact pressure sensor 41 for detecting a downward contact pressure in the same manner and contact pressure sensors (not illustrated) for detecting rightward and leftward contact pressures in the same manner are pasted to the above mentioned tip part 7. Signal lines (not illustrated) are connected respectively to the above mentioned contact pressure sensors 40 and 41 and are inserted through the above mentioned universal cable 6 to transmit respective contact pressure detecting signals to a contact pressure detecting circuit 26 within the above mentioned UCA through the above mentioned connector 3.

Figure 3:
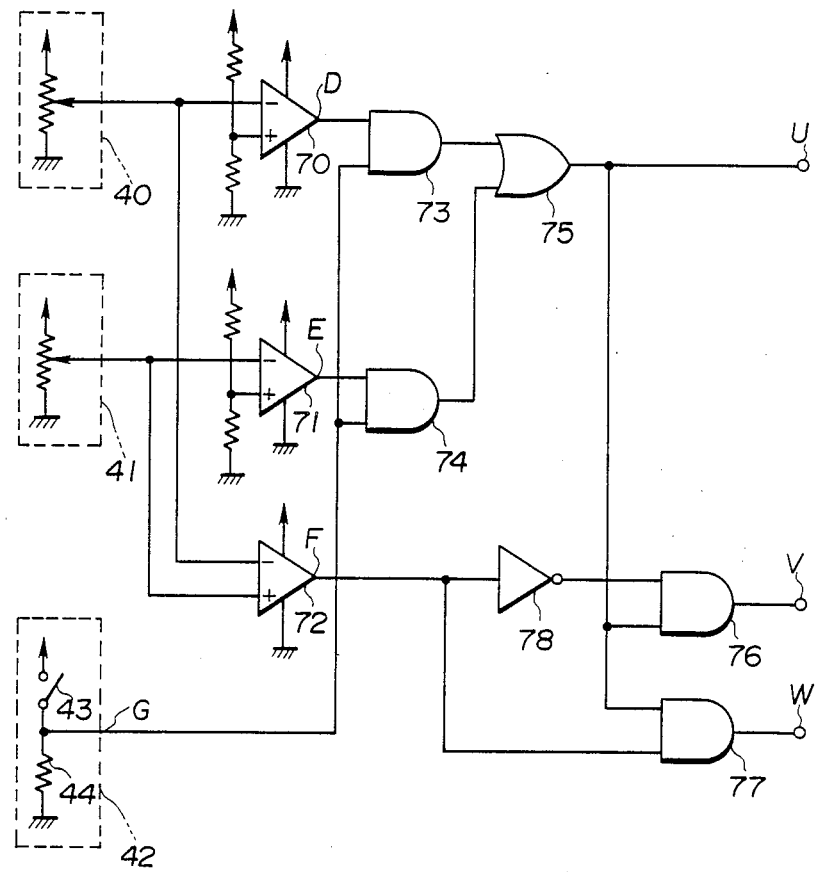

An oscillating wave motor (mentioned as a USM hereinafter) 12 as a motor driven, for example, by ultrasonic waves to pull a vertically bending wire 10 through a reduction gear 11 and a USM 15 to pull a horizontally bending wire 13 through a reduction gear 14 are provided within the above mentioned holding part 5. The above mentioned holding part 5 is provided on the surface with an air/water feeding button, sucking button, $CO_2$, gas feeding button, forceps raising mechanism, video processor controlling freezing and releasing and VTR starting switches, bending direction controlling bending switch 16 and free/lock switch (mentioned as an F/L switch hereinafter) 42 relating to the present invention. By the way, as shown in FIG. 3, the above mentioned F/L switch 42 is a combination of a switch 43 and resistance 44 which can be equivalently represented.

Within the above mentioned endoscope 1 are built-in a light guide fiber, air/water feeding tube, treating instrument inserting channel and others.

The above mentioned UCA 2 is provided with a lamp 17 feeding an illuminating light to the above mentioned endoscope 1, air feeding pump 18 feeding air, water feeding tank 19 storing water to be fed, water feeding pump 20 to feed water, bending switch controlling circuit 21 for controlling the above mentioned bending switch 16, USM controlling circuits 22 and 23 for controlling the above mentioned USM's 12 and 15, the above mentioned video processor 24 for processing the image signal obtained by the above mentioned endoscope 1, a bending angle detecting circuit 25 for detecting the bending angle of the above mentioned bendable part 8 and the above mentioned contact pressure detecting circuit 26 for detecting the contacting pressure with a body cavity wall. By the way, the above mentioned UCA 2 may be made by electrically and physically connecting apparatus of respectively separate formations. A monitor 27 is connected to the above mentioned video processor 24 so that the image signal variously processed by the above mentioned video processor 24 may be displayed.

The above mentioned bending angle detecting circuit 25 is to obtain the bending angle detecting information from rotation angle sensors 30 and 31 formed of photoreflectors or the like and feed the information to the above mentioned video processor 24.

The contact pressure detecting signals from the above mentioned contact pressure sensors 40 and 41 and the right and left contact pressure sensors (not illustrated) are to be input into the above mentioned contact pressure detecting circuit 26. The contact pressures are detected from these contact pressure detecting signals and are fed to the above mentioned USM controlling circuits 22 and 23 and the above mentioned video processor 24. By the way, as shown in FIG. 3, the above mentioned contact pressure sensors 40 and 41 are equivalent to variable resistances so that, the larger the contact pressure, the lower the resistance value and, in case there is no contact pressure, the resistance will be high.

In the above mentioned video processor 24, the image signal from the above mentioned solid state imaging device 33 and the signal from the above mentioned contact pressure detecting circuit 26 are variously processed such as synthesized and are displayed in the above mentioned monitor 27.

Now, the above mentioned bending switch 16 is a joy stick type switch so that, when a lever 28 is inclined, the bending of the above mentioned bendable part 8 will be controlled to be in respective vertical/horizontal directions and, in response to the inclination, when the angle of inclination is small, the resistance value will be small and, when the angle of inclination is large, the resistance value will be large. Also, in the respective vertical/horizontal directions, when the bendable part is upward (downward), it will not be able to be bent downward (upward) and, when it is bent rightward (leftward), it will not be able to be bent leftward (rightward). In the combinations of upward and rightward, upward and leftward, downward and rightward and downward and leftward, it can be bent simultaneously. That is to say, it can be bent in the intermediate direction of each combination. By the way, the above mentioned bending switch 16 is to be automatically returned to the neutral position by the energizing force of a spring or the like.

Figure 2:
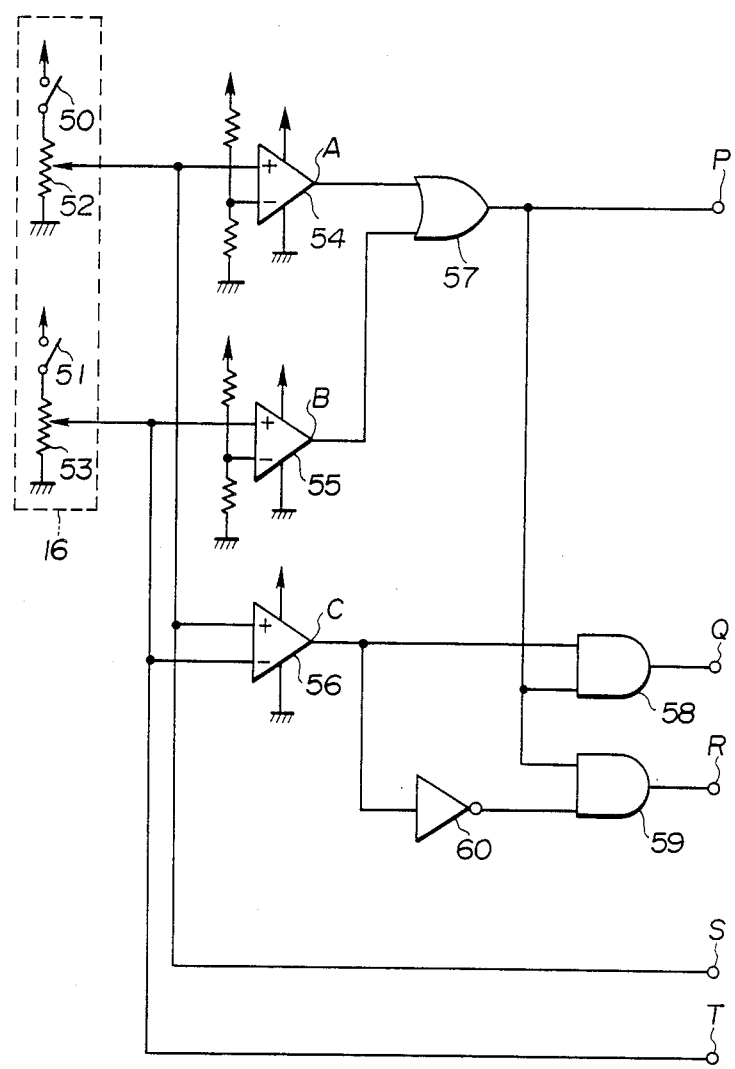

As shown in FIG. 2, the above mentioned bending switch 16 can be equivalently represented by a switch 50 showing that the above mentioned lever 28 is inclined upward, a variable resistance 52 showing the angle of upward inclination of the above mentioned lever 28, in the same manner, a switch 51 showing that the above mentioned lever 28 is inclined downward, a variable resistance 53 showing the angle of upward inclination of the above mentioned lever 28, a switch not illustrated showing that the above mentioned lever 28 is inclined rightward and leftward and a variable resistance showing the angles of rightward and leftward inclinations of the above mentioned lever 28.

FIG. 2 shows a formation of the above mentioned bennding switch controlling circuit 21 for controlling the above mentioned bendable part 8 to be bent upward and downward. The formation for controlling the above mentioned bendable part 8 to be bent rightward and leftward is the same as of bending upward and downward and therefore shall not be described here.

The above mentioned variable resistance 52 is connected at one end to a constant current source through the above mentioned switch 50, is earthed at the other end and is connected at the intermediate point to a comparator 54 at the irreversible input end, to a comparator 56 at the irreversible input end and to an S terminal. The above mentioned variable resistance 53 is connected at one end to a constant current source through the above mentioned switch 51, is earthed at the other end and is connected at the intermediate point to a comparator 55 at the irreversible input end, to the above mentioned comparator 56 at the reversible input end and to a T terminal. The above mentioned comparator 54 is connected at the irreversible input end with the above mentioned variable resistance 52 and at the reversible input end with a comparative potential. The above mentioned comparator 55 is connected at the irreversible input end with the above mentioned variable resistance 53 and at the reversible end with a comparative potential. The above mentioned comparator 56 is connected at the irreversible input end with the above mentioned variable resistance 52 and at the reversible input end with the above mentioned variable resistance 53. The above mentioned comparator 54 is connected at the output end A to an OR circuit 57 at the first input end. The above mentioned comparator 55 is connected at the output end B to the above mentioned OR circuit 57 at the second input end. The above mentioned comparator 56 is connected at the output end C to an AND circuit 58 at the first input end and to an AND circuit 59 at the first input end through an inverter 60. The above mentioned OR circuit 57 is connected at the output end to the above mentioned AND circuits 58 and 59 at the second input ends and to a P terminal. The above mentioned AND circuit 58 is connecated at the output end to a Q terminal. The above mentioned AND circuit 59 is connected at the output end to an R terminal.

FIG. 3 shows a formation of processing the contact pressure detecting signals of the above mentioned contact pressure sensors 40 and 41 pasted to the upper and lower positions of the above mentioned tip part 7. The formation of processing the contact pressure detecting signals of the contact pressure sensors pasted to the right and left is the same as in the upper and lower lower positions and therefore shall not be explained here.

The above mentioned contact pressure sensor 40 is connected at one end to an electric power source, is earthed at the other end and is connected at the intermediate point to a comparator 70 at the reversible input end and to a comparator 72 at the reversible input end. The above mentioned contact pressure sensor 41 is connected at one end to an electric power source, is earthed at the other end and is connected at the intermediate point to a comparator 71 at the reversible input end and to the above mentioned comparator 72 at the irreversible input end. The above mentioned resistance 44 is earthed at one end, is connected at the other end to an electric power source through the above mentioned switch 43 and is connected as the output end G of the above mentioned F/L switch 42 to the AND circuits 73 and 74 at the second input ends. The above mentioned comparator 70 is connected at the reversible input end with the above mentioned contact pressure sensor 40 and at the irreversible input end with a comparative potential. The above mentioned comparator 71 is connected at the reversible input end with the above mentioned contact pressure sensor 41 and at the irreversible input end with a comparative potential. The above mentioed comparator 72 is connected at the reversible input end with the above mentioned contact pressure sensor 40 and at the irreversible input end with the above mentioned contact pressure sensor 41. The above mentioned comparator 70 is connected at the output end D with the above mentioned AND circuit 73 at the first input end. The above mentioned comparator 71 is connected at the output end E with the above mentioned AND circuit 74 at the first input end. The above mentioned AND circuit 73 is connected at the output end with an OR circuit 75 at the first input end. An AND circuit 74 is connected at the output end with the above mentioned OR circuit 75 at the second input end. The above mentioned OR circuit 75 is connected at the output end with the above mentioned AND circuits 76 and 77 at the input ends and with a U terminal. The above mentioned comparator 72 is connected at the output end F with the AND circuits 76 and 77 at the first input ends through an inverter 78. The above mentioned AND circuit 76 is connected at the output end with a V terminal. The above mentioned AND circuit 77 is connected at the output end with a W terminal.

Figure 4:
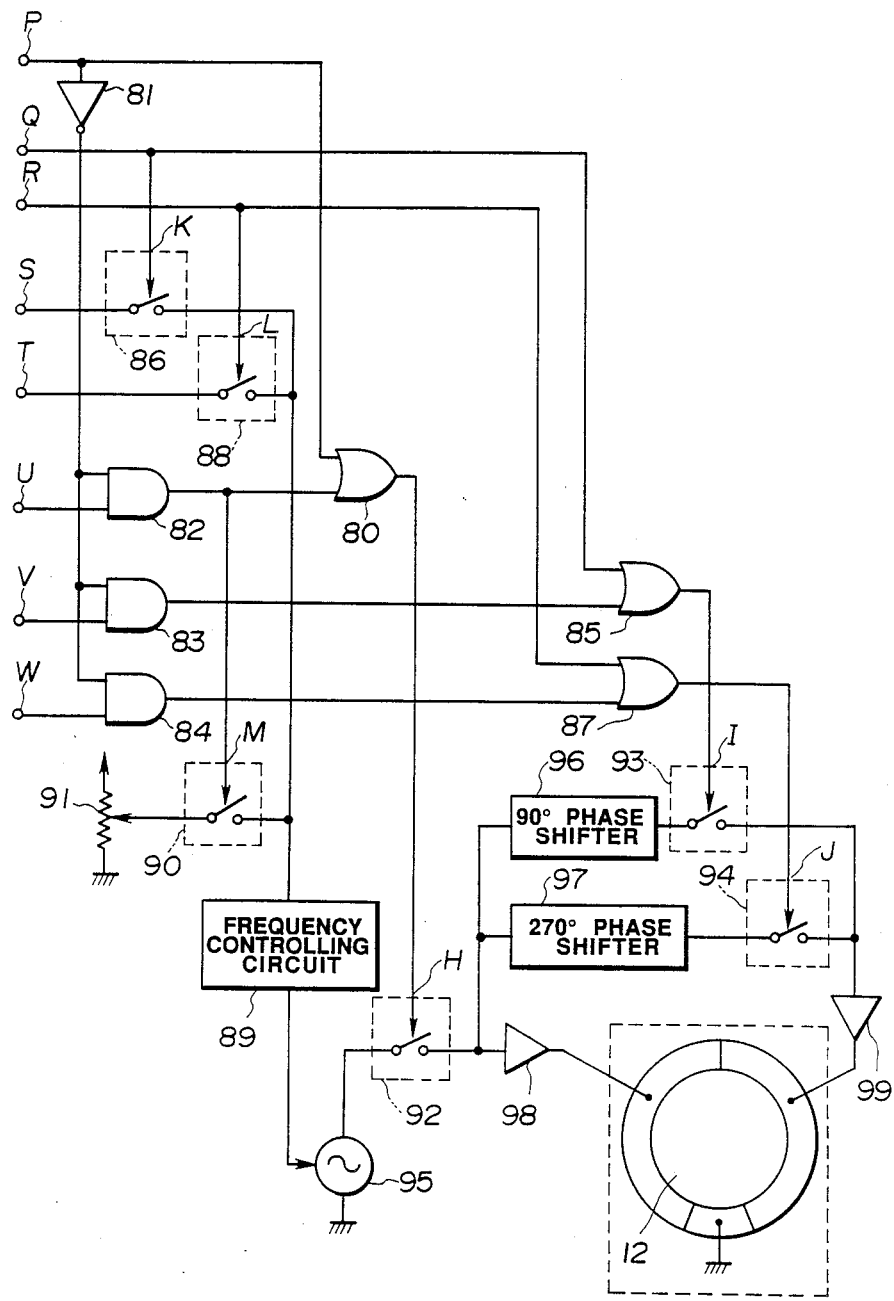

FIG. 4 shows a formation of the above mentioned USM controlling circuit 22 for controlling the above mentioned USM 12 in the vertical direction. The above mentioned USM controlling circuit 23 for controlling the USM 15 in the horizontal direction is the same as in the vertical direction and therefore shall not be described here.

The P to T terminals are connected respectively to terminals of the same names of the above mentioned bending switch controlling circuit 21 shown in FIG. 2. The U to W terminals are connected respectively to terminals of the same names of the above mentioned contact pressure detecting circuit 26 shown in FIG. 3.

Also, the above mentioned P terminal is connected to AND circuits 82, 83 and 84 at the second input ends through an inverter 81 and to an OR circuit 80 at the first input end. The above mentioned Q terminal is connected to a switch 86 at the control end K and to an OR circuit 85 at the first input end. The above mentioned R terminal is connected to a switch 88 at the control end L and to an OR circuit 87 at the first input end. The above mentioned U terminal is connected to the above mentioned AND circuit 82 at the first input end. The above mentioned V terminal is connected to the above mentioned AND circuit 83 at the first input end. The abve mentioned W terminal is connected to the above mentioned AND circuit 84 at the first input end. The above mentioned AND circuit 82 is connected at the output end to a switch 90 at the control end M and to the above mentioned OR circuit 80 at the second input end. The above mentioned AND circuit 83 is connected at the output end to the above mentioned OR circuit 85 at the second input end. The above mentioned AND circuit 84 is connected at the output end to the above mentioned OR circuit 87 at the second input end. The above mentioned OR circuit 80 is connecated at the output end to a switch 92 at the control end H. The above mentioned OR circuit 85 is connected at the output end to a switch 93 at the control end I. The above mentioned OR circuit 87 is connected at the output end to a switch 94 at the control end J. A variable resistance 91 is connected at one end to an electric power source, is earthed at the other end and is connected at the intermediate point to a frequency controlling circuit 89 at the input end through the above mentioned switch 90. The above mentioned frequency controlling circuit 89 is connected at the input end to the above mentioned S terminal through the above mentioned switch 86, to the above mentioned T terminal through the above mentioned switch 88 and to the abpve mentioned variable resistance 91 at the intermediate point through the above mentioned switch 90. The above mentioned frequency controlling circuit 89 is connected at the output end to a sine wave generating circuit 95 at the control input end. The above mentioned sine wave generating circuit 95 is connected at the output end to a 90 degree phase shifter 96, 270 degree phase shifter 97 and amplifier 98 at the input ends through the above mentioned switch 92. An amplifier 99 is connected at the input end to the above mentioned 90 degree phase shifter 96 at the output end through the above mentioned switch 93 and to the above mentioned 270 degree phase shifter 97 at the output end through the above mentioned switch 94. The above mentioned amplifiers 98 and 99 are connected at the output ends to the above mentioned USM 12.

First of all, the operation of the above mentioned bending switch controlling circuit 21 shown in FIG. 2 shall be explained.

When the above mentioned lever 28 of the above mentioned bending switch 16 is in the neutral position, that is to say, the above mentioned switches 50 and 51 are OFF, no current will flow through the above mentioned variable resistances 52 and 53 and the electromotive voltage will be zero. Therefore, as the voltage at the input ends connected to the above mentioned variable resistances 52 and 53 will be zero, the above mentioned comparators 54 and 55 at the output ends A and B will be of low level logical values (which shall be mentioned as "L" hereinafter). Thereby, as the input ends connected to the above mentioned comparators 54 and 55 will be of "L", the above mentioned OR circuit 57 will be of "L" at the output end. That is to say, as the input end connected to the above mentioned OR circuit 57 will be of "L", even if the input end connected to the output end of the above mentioned comparator 56 is of a high level logical value (which shall be mentioned as "H" hereinafter) or "L", the above mentioned AND circuit 58 will be of "L" at the output end. Also, as the input end connected to the above mentioned OR circuit 57 will be of "L", even if the input end connected to the output end of the above mentioned inverter 60 is of "H" or "L", the above mentioned AND circuit 59 will be of "L" at the output end.

That is to say, when the above mentioned lever 28 of the above mentioned bending switch 16 is in the neutral position, the above mentioned P to R terminals will be of "L" and the above mentioned S and T terminals will be of zero potential.

Here, if the above mentioed lever 28 of the above mentioned bending switch 16 is inclined so that the above mentioned bendable part 8 may bend upward, the above mentioned switch 50 will be ON and an electric current will flow through the above mentioned variable resistance 52. Thereby, a voltage corresponding to the inclination of the above mentioned lever 28 will be produced at the intermediate point of the above mentioned variable resistance 52. Therefore, when the voltage at the intermediate point of the above mentioned variable resistance 52 gradually increases to exceed a threshold level, the above mentioned comparator 54 will be of "H" at the output end A.

Also, as the above mentioned switch 51 will not be ON simultaneously with the above mentioned switch 50 as described above, no current will flow through the above mentioned variable resistance 53 and the voltage of the above mentioned variable resistance 53 at the intermediate point will be zero. Therefore, as the voltage of the above mentioned variable resistance 53 at the intermediate point will be zero, the above mentioned comparator 55 will be of "L" at the output end B.

Thereby, as the input end connected to the output end A of the above mentioned comparator 54 will be of "H", even if the input end connected to the output end B of the above mentioned comparator 55 is of "L" or "H", the above mentioned OR circuit 57 will be of "H" at the output end.

Also, the above mentioned comparator 56 will be of "H" at the output end C by comparing the voltage of the above mentioned variable resistance 52 at the intermediate point connected to the irreversible input end and the voltage of the above mentioned variable resistance at the intermediate point connected to the reversible input end with each other. Thereby, as the input end connected to the output end of the above mentioned OR circuit will be of "H" and the input end connected to the output end C of the above mentioned comparator 56 will be also of "H", the above mentioned AND circuit 58 will be of "H" at the output end. As the input end connected to the output end C of the above mentioned comparator 56 will be of "H", the above mentioned inverter 60 will be of "L" at the output end. Therefore, even if the input end connected to the output end of the above mentioned OR circuit 57 is "H", as the input end connected to the output end of the above mentioned inverter 60 will be of "L", the above mentioned AND circuit 59 will be of "L" at the output end.

That is to say, when the above mentioned lever 28 of the above mentioned bending switch 16 is inclined so that the above mentioned bendable part 8 may bend upward, the above mentioned P terminal will be of "H", the above mentioned Q terminal will be of "L", the above mentioned S terminal will be of a voltage corresponding to the inclination of the above mentioned lever 28 and the above mentioned T terminal will be of zero potential.

Also when the above mentioned lever 28 of the above mentioned bending switch 16 is inclined so that the above mentioned bendable part may bend downward, the above mentioned switch 51 will be ON and an electric current will flow through the above mentioned variable resistance 53. Thereby, a voltage corresponding to the inclination of the above mentioned lever 28 will be produced in the above mentioned variable resistance at the intermediatae point. Therefore, when the voltage of the above mentioned variable resistance 53 at the intermediate point gradually increases to exceed a threshold level, the above mentioned comparator 55 will be of "H" at the output end B.

As the above mentioned switch 50 will not be ON simultaneously with the above mentioned switch 51 as described above, no current will flow through the above mentioned variable resistance 52 and the voltage of the above mentioned variable resistance 52 at the intermediate point will be zero. Therefore, as the voltage of the above mentioned variable resistance 52 at the intermediate point is zero, the above mentioned comparator 54 will be of "L" at the output end A.

Thereby, as the input end connected to the output end A of the above mentioned comparator 54 will be of "L" but the input end connected to the output end B of the above mentioned comparator 55 will be of "H", the above mentioned OR circuit 57 will be of "H" at the output end.

Also, the above mentioned comparator 56 will be of "L" at the output end by comparing the voltage of the above mentioned variable resistance 52 at the intermediate point connected to the irreversible input end and the voltage of the above mentioned variable resistance 53 at the intermediate point with each other. Thereby, as the input end connected to the output end C of the above mentioned comparator 56 will be of "L", the above mentioned inverter 60 will be of "H" at the output end. Therefore, as the input end connected to the output end of the above mentioned OR circuit 57 will be of "H" and the input end connected to the output end of the above mentioned inverter 60 will be also of "H", the above mentioned AND circuit 59 will be of "H" at the output end. As the input end connected to the output end of the above mentioned OR circuit 57 will be of "H" but the input end connected to the output end C of the above mentioned comparator 56 will be of "L", the above mentioned AND circuit 58 will be of "L" at the output end.

That is to say, if the above mentioned lever 28 of the above mentioned bending switch 16 is inclined so that the above mentioned bendable part 8 may bend downward, the abode mentioned P terminal will be of "H", the above mentioned Q terminal will be of "L", the abve mentioned R terminal will be of "H", the above mentioned T terminal will be of a voltage corresponding to the inclination of the above mentioned lever 28 and the above mentioned S terminal will be of zero voltage.

By the way, a switch by which the above mentioned switches 50 and 51 may be simultaneously ON may be used. In such case, a higher voltage value will be selected by the above mentioned comparator 56.

The operation of the above mentioned contact pressure detecting circuit 26 shown in FIG. 3 shall be explained in the following.

When the above mentioned F/L switch 42 is locked (L), that is, the above mentioned switch 43 is OFF, no current will flow through the above mentioned resistance 44 and the output end G of the above mentioned F/L switch 42 will be of "L". Therefore, as the input ends connected to the above mentioned F/L switch 42 are of "L", even if the input ends connected to the above mentioned compators 70 and 71 are of "H" or "L", the output ends of the above mentioned AND circuits 73 and 74 will be of "L".

Thereby, as the input ends connected to the output ends of the above mentioned AND circuits 73 and 74 will be of "L", the output end of the above mentioned OR circuit 75 will be of "L".

Therefore, as the input end connected to the above mentioned OR circuit 75 will be of "L", even if the input end connected to the output end of the above mentioned inverter 78 is of "H", the output end of the above mentioned AND circuit 76 will be of "L". Also, as the input end connected to the above mentioned OR circuit will be of "L", even if the input end connected to the output end of the above mentioned comparator 72 is of "H" or "L", the output end of the above mentioned AND circuit 77 will be of "L". Also, as the input end connected to the above mentioned OR circuit 75 will be of "L", even if the input end connected to the output end of the above mentioned comparator 72 is of "H" or "L", the output end of the above mentioned AND circuit 77 will be of "L".

That is to say, if the above mentioned F/L switch 42 is locked (L), even if the voltage of the above mentioned contact pressure sensor 40 at the intermediate point gradually reduces until the output end of the above mentioned comparator 72 becomes to be of "H" or, even if the voltage of the above mentioned contact pressure sensor 41 at the intermediate point gradually reduces until the output end of the above mentioned comparator 72 becomes to be of "H", the above mentioned U to W terminals will be of "L".

If the above mentioned F/L switch 42 is free (F), that is, if the above mentioned switch 43 is ON, an electric current will flow through the above mentioned resistance 44 and the output end G of the above mentioned F/L switch 42 will become to be of "H".

In this state, if the above mentioned contact pressure sensor 40 pasted to the upper part of the above mentioned tip part 7 contacts such inspected part as the inside wall of a body cavity, the voltage of the above mentioned contact pressure sensor 40 at the intermediate point will gradually reduce so that, if the voltage of the above mentioned contact pressure sensor 40 at the intermediate point exceeds a threshold level, the above mentioned comparator 70 will be of "H" at the output end D. Therefore, as the input end connected to the output end D of the above mentioned comparator 70 will be of "H" and the input end connected to the output end G of the above mentioned F/L switch 42 will be of "H", the above mentioned AND circuit 73 will be of "H" at the output end.

However, as the above mentioned contact pressure sensor 41 will be of a high impedance and its output voltage will not exceed a threshold level, the above mentioned comparator 71 will be of "L" at the ourput end E. Therefore, as the output end E of the above mentioned comparator 71 will be of "L", even if the input end connected to the output end G of the above mentiioned F/L switch 42 is of "H" or "L", the above mentioned AND circuit 74 will be of "L"at the output end.

Thereby, as the input end connected to the output end of the above mentioned AND circuit 73 will be of "H", even if the input end connected to the output end of the above mentioned AND circuit 74 is of "L" or "H", the above mentioned OR circuit 75 will be of "H" at the output end.

Also, the above mentioned comparator 72 will be of "H" at the output end F by comparing the voltage of the above mentioned contact pressure sensor 40 at the intermediate point connected to the reversible input end and the voltage of the above mentioned contact pressure sensor 41 at the intermediate point connected to the irreversible input end with each other. Therefore, as the input end connected to the above mentioned OR circuit 75 will be of "H" and the input end connected to the output end of the above mentioned comparator 72 will be of "H", the above mentioned AND circuit 77 will be of "H" at the output end. As the input end connected to the above mentioned comparator 72 will be of "H", the above mentioned inverter 78 will be of "L" at the output end. Therefore, even if the input end connected to the above mentioned OR circuit 75 is of "H", as the input end connected to the above mentioned inverter 78 will be of "L", the above mentioned AND circuit 76 will be of "L" at the output end.

That is to say, when the above mentioned F/L switch 42 is locked (L), the above mentioned contact pressure sensor 40 contacts such inspected part as the inside wall of a body cavity and the voltage of the above mentioned contact pressure sensor 40 at the intermediate point gradually reduces until the above mentioned comparator 70 becomes to be of "H" at the output end D, the above mentioned U terminal will be of "H", the above mentioned V terminal will be of "L" and the above mentioned W terminal will be of "H".

When the above mentioned contact pressure sensor 41 pasted to the lower part of the insertable part 7 contacts such inspected part as the inside wall of a body cavity, the voltage of the above mentioned contact pressure sensor 41 at the intermediate point will gradually reduce so that, when the voltage of the above mentioned contact pressure sensor 41 at the intermediate point exceeds a threshold level, the above mentioned comparator 71 will be of "H" at the output end E. Therefore, as the input end connected to the output end E of the above mentioned comparator 71 will be of "H" and the input end connected to the output end G of the above mentioned F/L switch 42 will be of "H", the above mentioned AND circuit 74 will be of "H" at the output end.

However, as the above mentioned contact pressure sensor 40 will be of a high impedance and its output voltage will not exceed the threshold level, the above mentioned comparator 70 will be of "L" at the output end D. Therefore, even if the output end E of the above mentioned comparator 70 is of "L" and the input end connected to the output end G of the above mentioned F/L switch 42 is of "H", the above mentioned AND circuit 73 will be of "L" at the output end.

Thereby, as the input end connected to the output end of the above mentioned AND circuit 74 will be of "H", even if the input end connected to the output end of the above mentioned AND circuit 73 is of "L", the above mentioned OR circuit 75 will be of "H" at the output end.

Also, the above mentioned comparator 72 will be of "L" at the output end F by comparing the voltage of the above mentioned contact pressure sensor 40 at the intermediate point connected to the reversible input end and the voltage of the above mentioned contact pressure sensor 41 at the intermediate point connected to the irreversible input end with each other. Therefore, as the input end connected to the above mentioned comparator 72 will be of "L", the above mentione inverter 78 will be of "H" at the output end. Thereby, as the input end connected to the above mentioned OR circuit 75 will be of "H" and the input end connected to the output end of the above mentioned inverter 78 will be of "H", the above mentioned AND circuit 78 will be of "H" at the output end. Even if the input end connected to the above mentioned OR circuit 75 is of "H", as the input end connected to the above mentionend comparator 72 will be of "L", the above mentioned AND circuit 77 will be of "L" at the output end.

That is to say, when the above mentioned F/L switch 42 is locked (L), the above mentioned contact pressure sensor 41 contacts such inspected part as the inside wall of a body cavity and the voltage of the above mentioned contact pressure sensor 41 at the intermediate point gradually reduces until the above mentioned comparator 71 becomes to be of "H" at the output end E, the above mentioned U terminal will be of "H", the above mentioned V terminal will be of "H" and the above mentioned W terminal will be of "L".

The operation of the above mentioned USM controlling circuit 22 shown in FIG. 4 shall be explained in the following.

As described above, if the above mentioned lever 28 of the above mentioned bending switch 16 is in the neutral position and the above mentioned F/L switch 42 is (L), the above mentioned P to R terminals and the above mentioned U to W terminals will be of "L". Therefore, as the input end connected to the above mentioned P terminal will be of "L", the above mentioned inverter 81 will be of "H" at the output end. However, even if the input end connecated to the output end of the above mentioned inverter 81 is of "H", as the input end connected to the above mentioned U terminal will be of "L", the above mentioned AND circuit 82 will be of "L" at the output end. Even if the input end connected to the output end of the above mentioned inverter 81 is of "H", as the input end connected to the above mentioned V terminal will be of "L", the above mentioned AND circuit 83 will be of "L" at the output end. Even if the input end connected to the output end of the above mentioned inverter 81 is of "H", as the input end connected to the above mentioned W terminal will be of "L", the above mentioned AND circuit 84 will be of "L" at the output end.

Also, the above mentioned OR circuit 80 will be of "L" at the output end because the input end connected to the above mentioned F terminal will be of "L" and the inpput end connected to the output end of the above mentioned AND circuit 82 will be also of "L". Thereby, the above mentioned switch 92 will be OFF because the control end H connected to the output end of the above mentioned OR circuit 80 will be of "L". Therefore, as the above mentioned switch 92 will be OFF, the output of the above mentioned sine wave generating circuit 95 will not be input into the above mentioned 90 degree phase shifter 96, 270 degree phase shifter 97 and amplifier 98.

By the way, the above mentioned OR circuit 85 will be of "L" because the input end connected to the above mentioned Q terminal will be of "L" and the input end connected to the output end of the above mentioned AND circuit 83 will be also of "L". Therefore, the above mentioned switch 93 will be OFF because the above mentioned OR circuit 85 will be of "L" at the output end connected to the control end I. Also, the above mentioned OR circuit 87 will be of "L" at the output end because the input end connected to the above mentioned R terminal will be of "L" and the input end connected to the output end of the above mentioned AND circuit 84 will be also of "L". Therefore, the above mentioned switch 94 will be OFF because the output end of the above mentioned OR circuit 87 connected to the control end J will be of "L".

By the way, the above mentioned switches 86 and 88 will be both OFF because the control ends K and L connected respectively to the above mentioned Q and R are of "L". The above mentioned switch 90 will be OFF because the control end M connected to the output end of the above mentioned AND circuit 82 will be of "L". Thereby, the above mentioned frequency controlling circuit 89 will be opened at the input end because the above mentioned switches 86, 88 and 90 will be respectively OFF.

That is to say, when the above mentioned lever 28 of the above mentioned bending switch 16 is in the neutral position and the above mentioned F/L switch 42 is (L), the above mentioned USM 12 will not be fed with the output of the sine wave generating circuit 92 and will be locked to be stationary so as not to easily collapse in the state even if an external force is applied.

Next, when the above mentioned lever 28 of the above mentioned bending switch 16 is inclined so that the above mentioned bendable part 8 may bend upward, the above mentioned P terminal will be of "H", the above mentioned Q terminal will be of "H", the above mentioned R terminal will be of "L" and the above mentioned S terminal will be of a voltage corresponding to the inclination of the above mentioned lever 28. Therefore, the above mentioned inverter 81 will be of "L" at the output end because the input end connected to the above mentioned P terminal will be of "H". Thereby, the above mentioned AND circuit 82 will be of "L" at the output end because the input end connected to the output end of the above mentioned inverter 81 will be of "L" and even if the input end connected to the above mentioned U terminal is of "H". Also, the above mentioned AND circuit 83 will be of "L" at the output end because the input end connected to the output end of the above mentioned inverter 81 will be of "L" and even if the input end connected to the above mentioned V terminal is of "H" or "L". The above mentioned AND circuit 84 will be of "L" at the output end because the input end connected to the output end of the above mentioned inverter 81 will be of "L" and even if the input end connected to the above mentioned W terminal is of "H" or "L".

The above mentioned OR circuit 80 will be "H" at the output end because the input end connected to the above mentioned P terminal will be of "H" and even if the input end connected to the output end of the above mentioned AND circuit 82 is of "L". Therefore, the above mentioned switch 92 will be ON because the control end H connected to the output end of the above mentioned OR circuit 80 will be of "H". Thereby, as the above mentioned switch 92 will be ON, the output of the above mentioned sine wave generating circuit 95 will be input into the above mentioned 90 degree phase shifter 96, 270 deree phase shifter 97 and amplifier 98.

Also, the above mentioned OR circuit 85 will be of "H" at the output end because the input end connected to the above mentiooed Q terminal will be of "H" and even if the input end connected to the outpurt end of the above mentioned AND circuit 83 is of "L". Therefore, the above mentioned switch 93 will be ON because the control end I connected to the output end of the above mentioned OR circuit 85 will be of "H". Thereby, as the above mentioned switch 93 will be ON, the output of the above mentioned 90 degree phase shifter 96 will be input into the above mentioned amplifier 99.

However, the above mentioned OR circuit 87 will be of "L" at the output end because the input end connected to the above mentioned R terminal will be of "L" and the input end connected to the output end of the above mentioned AND circuit 84 will be also of "L". Therefore, the above mentioned switch 94 will be OFF because the control end J connected to the output end of the above mentioned OR circuit 87 will be of "L". Thereby, as the above mentioned switch 94 will be OFF, the output of the above mentioned 270 degree phase shifter 97 will not be input into the above mentioned amplifier 99.

The above mentioned switch 86 will be ON because the control end K connected to the above mentioned Q terminal will be of "H". The above mentioned switch 88 will be OFF because the control end L connected to the above mentioned R terminal will be of "L". The above mentioned switch 90 will be OFF because the output end of the above mentioned AND circuit 82 connected to the control end M will be of "L". Therefore, the voltage of the above mentioned S terminal will be applied to the input end of the above mentioned frequency controlling circuit 89. Thereby, the above mentioned frequency controlling circuit 89 will control the output frequency of the above mentioned sine wave generating circuit 95.

Therefore, the output of the above mentioned sine wave generating circuit 95 will be input into the above mentioned amplifier 98, the output of the above mentioned 90 degree phase shifter 96 will be input into the above mentioned amplifier 99 and the outputs of the above mentioned amplifiers 98 and 99 will be input into the above mentioned USM 12 provided in the above mentlioned holding part 5 of the above mentioned endoscope 1.

By the way, the rotating speed of the above mentioned USM 12 depends on the output frequency of the above mentioned sine wave generating circuit 95. When the inclination of the above mentioned lever 28 of the above mentioned bending switch 16 is small and the input voltage of the above mentioned frequency controlling circuit 89 is low, the output frequency of the above mentioned sine wave generating circuit 95 will become high and the rotating speed of the above mentioned USM 12 will be low. As the inclination of the above mentioned lever 28 becomes larger and the input voltage of the above mentioned frequency controlling circuit 89 becomes larger, the output frequency will become lower to be equal to the resonance frequency of the above mentioned USM 12. The output frequency at which the inclination of the above mentioned lever 28 becomes maximum is so set as to be a frequency somewhat higher than the resonance frequency of the above mentioned USM 12.

That is to say, when the above mentioned lever 28 of the above mentioned bending switch 16 is inclined so that the above mentioned bendable part 8 may bend upward, the output of the above mentioned sine wave generating circuit 95 will be applied to the above mentioned USM 12 through the above mentioned amplifier 98, 90 degree phase shifter 96 and amplifier 99 and the above mentioned USM 12 will rotate at a speed corresponding to the inclination of the above mentioned lever 28 so as to bend the above mentioned bendable part 8 upward.

While the above mentioned lever 28 of the above mentioned bending switch 16 is being operated, the above mentioned P terminal will be of "H" and therefore, even if the above mentioned U to W terminals become to be of "H", the control of the above mentioned USM 12 will not be influenced. That is to say, the control of the above mentioned bending switch controlling circuit 21 will be preferred to the control of the above mentioned contact pressure detecting circuit 26.

When the above mentioned lever 28 of the above mentioned bending switch 16 is inclined so that the above mentioned bendable part 8 may bend downward, the above mentioned P terminal will be of "H", the above mentioned Q terminal will be of "L" and the above mentioned T terminal will be of a voltage corresponding to the inclination of the above mentioned lever 28. Therefore, the above mentioned inverter 81 will be of "L" at the output end because the input end connected to the above mentioned P terminal will be of "H". Thereby, the above mentioned AND circuit 82 will be of "L" at the output end because the input end connected to the output end of the above mentioned inverter 81 will be of "L" and even if the input end connected to the above mentione U terminal is of "H" or "L". The above mentioned AND circuit 83 will be of "L" at the output end because the input end connected to the output end of the above mentioned inverter 81 will be of "L" and even if the input end connected to the above mentione V terminal is of "H" or "L". The above mentioned AND circuit 84 will be of "L" at the output end because the input end connected to the output end of the above mentioned inverter 81 will be of "L" and even if the input end connected to the above mentione W terminal is of "H" or "L".

Also, the above mentioned OR circuit 80 will be of "H" at the output end because the input end connected to the above mentioned P terminal will be of "H" and even if the input end connected to the output end of the above mentioned AND circuit 82 is "L". Therefore, the above mentioned switch 92 will be ON because the control end H connected to the output end of the above mentioned OR circuit 80 will be of "H". Thereby, as the above mentioned switch 92 will be ON, the output of the above mentioned sine wave generating circuit 95 will be input into the above mentioned 90 degree phase shifter 96, 270 degree phase shifter 97 and amplifier 98.

The above mentioned OR circuit 87 will be of "H" at the output end because the input end connected to the above mentioned R terminal will be of "H" and even if the input end connected to the output end of the above mentioned AND circuit 84 is of "L". Therefore, the above mentioned switch 94 will be ON because the control end I connected to the output end of the above mentioned OR circuit 87 will be of "H". Thereby, as the above mentioned switch 94 will be ON, the output of the above mentioned 270 degree phase shifter 97 will be input into the above mentioned amplifier 99.

However, the above mentioned OR circuit 85 will be of "L" at the output end because the input end connected to the above mentioned Q terminal will be of "L" and the input end connected to the outpput end of the above mentioned AND circuit 83 will be also of "L". Therefore, the above mentioned switch 93 will be OFF because the control end I connected to the output end of the above mentioned OR circuit 85 will be of "L". Thereby, as the above mentione switch 93 will be OFF, the output of the above mentioned 90 degree phase shifter 96 will not be input into the above mentione amplifier 99.

Also, the above mentioned switch 86 will be OFF because the control end K connected to the above mentioned Q terminal will be of "L". The above mentioned switch 88 will be ON because the control end L connected to the above mentioned R terminal will be of "H". The above mentioned switch 90 will the OFF because the control end M connected to the output end of the above mentioned AND circuit 82 will be of "L". Therefore, the voltage of the above mentioned T terminal will be applied to the above mentioned frequency controlling circuit 89 at the input end. Thereby, the above mentioned frequency controlling circuit 89 will control the output frequency of the above mentioned sine wave generating circuit 95.

Therefore, the output of the above mentioned sine wave generating circuit 95 will be input into the above mentioned amplifier 98. The output of the above mentioned 270 degree phase shifter 97 will be input into the above mentioned amplifier 99. The outputs of the above mentioned amplifiers 98 and 99 will be input into the above mentioned USM 12 provided in the above mentioned holding part 5 of the above mentionend endoscope 1.

That is to say, when the above mentioned lever 28 of the above mentionend bending switch is inclined so that the above mentioned bendable part 8 may bend downward, the output of the sire wave generating circuit 92 will be applied to the above mentioned USM 12 through the above mentioned amplifier 98, 270 degree phase shifter 97 and amplifier 99 and the above mentioned USM 12 will rotate at a speed corresponding to the inclination of the above mentioned lever 28 so as to bend the above mentioned bendable part 8 downward.

When the above mentioned lever 28 of the above mentioned bending switch 16 is in the neutral positiion, the above mentioned P to R terminals will be of "L". In this state, when the above mentioned contact pressure sensor 40 contacts such inspected part as a part within a body cavity, the above mentioned U terminal will be of "H", the above mentioned V terminal will be of "L" and the above mentioned W terminal will be of "H". Therefore, the above mentioned inverter 81 will be of "H" at the output end because the input end connected to the above mentioned P terminal will be of "L". Thereby, the above mentioned AND circuit 82 will be of "H" at the output end because the input end connected to the above mentioned U terminal will be of "H" and the input end connected to the output end of the above mentioned inverter 81 will be also of "H". The above mentioned AND circuit 84 will be of "H" at the output end because the input end connected to the above mentioned W terminal will be of "H" and the input end connected to the output end of the above mentioned inverter 81 will be also of "H". However, the above mentioned AND circuit 83 will be of "L" at the output end because the input end connected to the above mentioned V terminal will be of "L" and even if the input terminal connected to the output end of the above mentioned inverter 81 is of "H".

Thereby, the above mentioned switch 90 will be ON because the control end M connected to the output end of the above mentioned AND circuit 82 will be of "H". Also, the above mentioned switches 86 and 88 will be OFF because the control ends K and L connected respectively to the above mentioned Q and R terminals will be of "L". Therefore, the voltage of the above mentioned variable resistance 91 at the intermediate point will be applied to the above mentioned frequency controlling circuit 89 at the input end. By the way, the voltage of the above mentioned variable resistance 91 at the intermediate point is so set as to be such voltage as slowly rotates the above mentioned USM 12.

Also, the above mentioned OR circuit will be of "H" at the output end because the input end connected to the AND circuit 82 will be of "H" and even if the input end connected to the above mentioned P terminal is of "L". Therefore, the above mentioned switch 92 will be ON because the control end H connected to the output end of the above mentioned OR circuit 80 will be of "H". Thereby, the output of the above mentioned sine wave generating circuit 95 will be input into the above mentioned amplifier 98, 90 degree phase shifter 96 and 270 degree phase shifter 97 through the above mentioned switch 92.

The above mentioned OR circuit 87 will be of "H" at the output end because the input end connected to the output end of the above mentioned AND circuit 84 will be of "H" and even if the input end connected to the above mentioned R terminal is of "L". Therefore, the above mentioned switch 94 will be ON because the control end J connected to the output end of the above mentioned OR circuit 87 will be of "H". Thereby, the output of the above mentioned 270 degree phase shifter 97 will be input into the above mentioned amplifier 99 through the above mentioned switch 94.

That is to say, when the above mentioned contact pressure sensor 40 pasted to the upper part of the above mentioned insertable part 4 contacts such inspected part as a part within a body cavity, the output of the sine wave generating circuit 92 will be applied to the above menntioned USM 12 through the above mentioned amplifier 98, 270 degree phase shifter 97 and amplifier 99 and the above mentioned USM 12 will rotate at a speed set by the above mentioned variable resistance 91 so as to bend the above mentioned bendable part 8 downward.

When the above mentioned contact pressure sensor pasted to the lower part of the above mentioned insertable part 4 contacts such inspected part as a part within a body cavity, the above mentioned U terminal will be of "H", the above mentioned V terminal will be of "H" and the above mentione W terminal will be of "L". Therefore, the above mentioned inverter 81 will be of "H" at the output end because the input end connected to the above mentioned P terminal will be of "L". Thereby, the above mentioned AND circuit 82 will be of "H" at the output end because the input end connected to the above mentioned U terminal will be of "H" and the input end connected to the output end of the above mentioned inverter 81 will be also of "H". Also, the above mentioned AND circuit 83 will be of "H" at the output end because the input end connected to the above mentioned V terminal will be of "H" and the input end connected to the output end of the above mentioned inverter 81 will be also of "H". However, the above mentioned AND circuit 84 will be of "L" at the output end because the input end connected to the above mentioned W terminal will be of "L" and even if the input end connected to the output end of the above mentioned inverter 81 is of "H".

Thereby, the above mentioned switch 90 will be ON because the control end M connected to the output end of the above mentioned AND circuit 82 will be of "H". The above mentioned switches 86 and 88 will be OFF because the control ends K and L connected respectively to the above mentioned Q and R terminals will be of "L". Therefore, the voltage of the above mentioned variable resistance 91 at the intermediate point will be applied to the above mentioned frequency controlling circuit 89 at the input end.

The above mentioned OR circuit 80 will be of "H" at the output end because the input end connected to the above mentionend AND circuit 82 will be of "H" and even if the input end connected to the above mentioned P terminal is of "L". Therefore, the above mentioned switch 92 will be ON because the control end H connected to the output end of the above mentioned OR circuit will be of "H". Thereby, the output of the above mentioned sine wave generating circuit 95 will be input into the above mentioned amplifier 98, 90 degree phase shifter 96 and 270 degree phase shifter through the above mentioned switch 92.

The above mentioned OR circuit 85 will be of "H" at the output end because the input end connected to the output end of the above mentioned AND circuit 83 will be of "H" and even if the input end connected to the above mentioned Q terminal is of "L". Therefore, the above mentioned switch 93 will be ON because the control end I connected to the output end of the above mentioned OR circuit 87 will be of "H". Thereby, the output of the above mentioned 90 degree phase shifter 96 will be input into the above mentioned amplifier 99 through the above mentioned switch 93.

That is to say, when the above mentioned contact sensor 41 pasted to the lower part of the above mentioned insertable part 4 contacts such inspected part as a part within a body cavity, the output of the sine wave generating circuit 92 will be applied to the above mentioned USM 12 through the above mentioned amplifier 98, 90 degree phase shifter 96 and amplifier 99 and the above mentioned USM 2 will rotate at a speed set by the above mentioned variable resistance 91 so as to bend the above mentioned bendable part upward.

The essential parts of the above described operations of the above mentioned bending switch controlling circuit 21, contact pressure detecting circuit 26 and USM controlling circuit 22 are shown in Table 1. By the way, in the table, "UD" represents an operating direction of the above mentioned bendable part 8 by the above mentioned bending switch 16, each of "P" to "T" represents a logical value or potential of the bending switch controlling circuit, "FL" represents a state of the above mentioned F/L switch 42, "Contact" represents a detecting direction of the above mentioned contact pressure sensor- 40 or 41, each of "U" to "W" represents a logical value of the terminal of the contact pressure detecting circuit, each of 86, 88, 90, 92, 93 and 94 represents the state of each switch of the above mentioned USM controlling circuit 22, the zero potential and the state that the switch is OFF are blank in "S" and "T" and "X" represents that any state will do.

P. The V and W terminals are connected respectively to OR circuits 107 and 108 at the second input ends. The above mentioned AND circuit 101 is connected at the output end to the above mentioned OR circuit 106 at the first input end. The above mentioned AND circuit 102 is connected at the output end to a switch 104 at the control end N and to the above mentioned OR circuit 107 at the first input end. The above mentioned AND circuit 103 is connected at the output end to a switch 105 at the control end 0 and to the above mentioned OR

TABLE 1

| UD | P | Q | R | S | T | FL | 86 | 88 | 90 | 92 | 93 | 94 | Contact | U | V | W |
|---|---|---|---|---|---|---|---|---|---|---|---|---|---|---|---|---|
| Central | L | L | L | | | L | | | | | | | X | L | L | L |
| Central | L | L | L | | | F | | | | | | | None | L | L | L |
| Central | L | L | L | | | F | | | ON | ON | | ON | Upward | H | L | H |
| Central | L | L | L | | | F | | ON | ON | ON | ON | | Downward | H | H | L |
| Upward | H | H | L | v | | F | ON | | | ON | ON | | None | L | L | L |
| Upward | H | H | L | v | | F | ON | | | ON | ON | | X | H | X | X |
| Downward | H | L | H | | v | F | | ON | | ON | | ON | None | L | L | L |
| Downward | H | L | H | | v | F | | ON | | ON | | ON | X | H | X | X |

In the thus formed first embodiment, when the above mentioned F/L switch 42 is switched to be free (F) and the above mentioned bending switch 16 is not operated, the above mentioned tip part 7 will contact on the side part with such inspected part as a part within a body cavity under a predetermined pressure, the above mentioned bendable part 8 will be bent under a bending resistance and the above mentioned tip part 7 will be moved in the direction of reducing the bending resistance so that the fear of hurting the inspected part with the above mentioned tip part 7 may be eliminated. In the case of pulling the above mentioned insertable part 4 out of the inspected object, without operating the above mentioned bending switch 16, the above mentioned tip part 7 will be able to be pulled out smoothly following the form of the inspected object so that a safe diagnosis or inspection may be made. Also, by switching the above mentioned F/L switch 42 to be locked (L) or operating the lever of the bending switch, the above mentioned tip part 7 can be contacted with the inspected part by the judgment of the operator. In such case, the contact pressure (bending resistance) will be displayed in the above mentioned monitor 27 so that the operator may give an accurate judgment.

Figure 5:
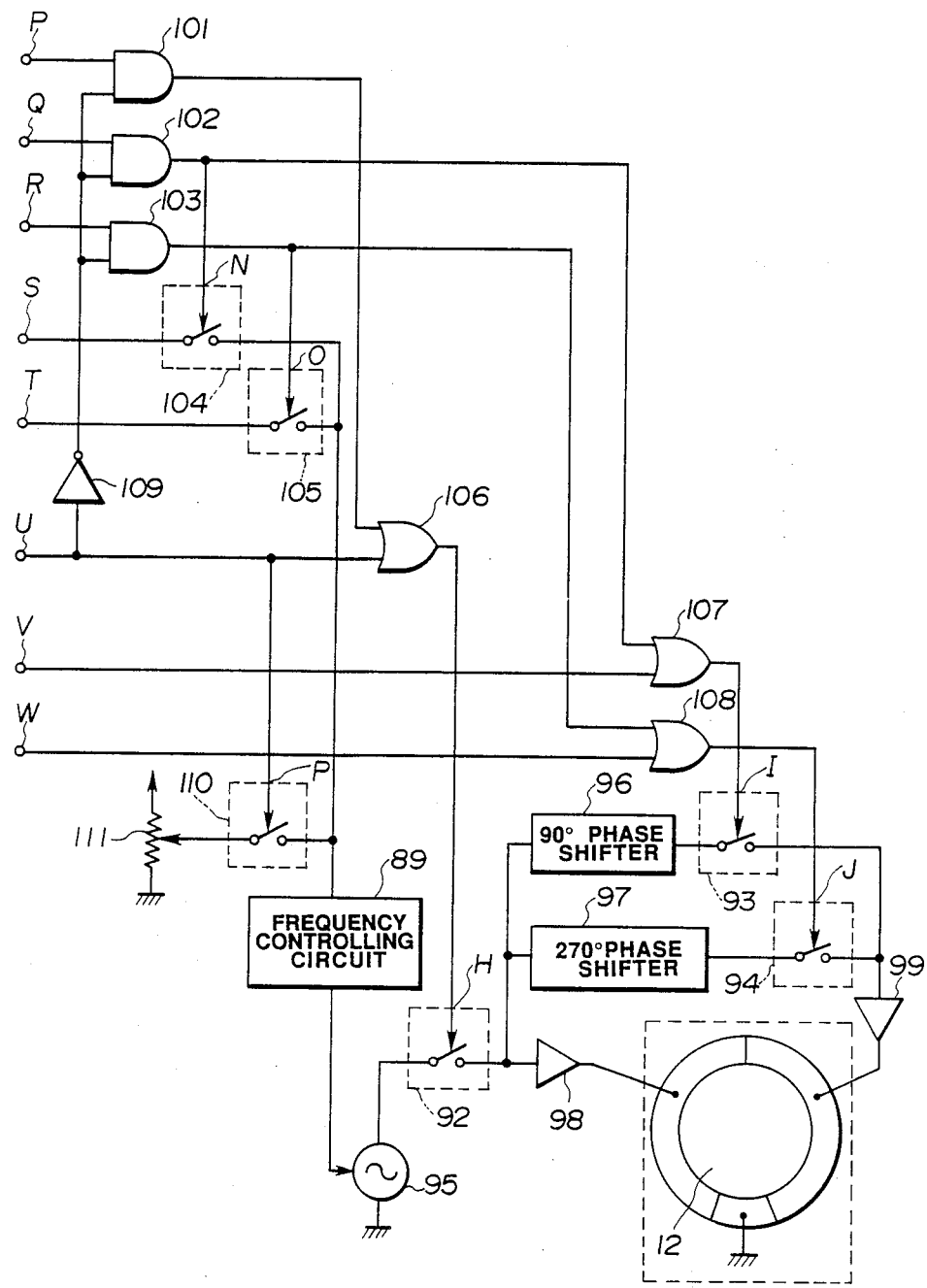
FIG. 5 relates to the second embodiment of the present invention.

In FIG. 5 is shown the second embodiment of the present invention. By the way, the formation of the bending switch controlling circuit is the same as in FIG. 2 of the first embodiment and shall not be described here.

In the block diagram showing the endoscope apparatus in this embodiment, the above mentioned F/L switch 42 shown in FIG. 1 of the first embodiment is removed and the formation of the contact pressure detecting circuiut is of the contact pressure detecting circuit shown in FIG. 3 of the first embodiment as the F/L switch is always ON.

FIG. 5 shows the formation of the USM controlling circuit 22 controlling the above mentioned USM 12 in the vertical direction. The above mentioned USM controlling circuit 23 controlling the USM 15 in the horizontal direction is the same as in the vertical direction and shall not be described here.

The P to R terminals are connected to AND circuits 101, 102 and 103 at the first input ends. The above mentioned U terminal is connected to the above mentioned AND circuits 101, 102 and 103 at the second input ends through an inverter 109, to an OR circuit 106 at the second input end and to a switch 110 at the control end circuit 108 at the first input end. The above mentioned OR circuit 106 is connected to a switch 92 at the control end H. The above mentioned OR circuit 107 is connected to a switch 93 at the control end I. The above mentioned OR circuit 108 is connected at the output end to a switch 94 at the control end J. A variable resistance 111 is connected at one end to an electric source, is earthed at the other end and is connected at the intermediate point to a frequency controlling circuit 89 through the above mentioned switch 110. The above mentioned frequency controlling circuit 89 is connected at the input end to the above mentioned S terminal through the above mentioned switch 104, to the above mentioned R terminal through the above mentioned switch 105 and to the above mentioned variable resistance 111 at the intermediate point through the above mentioned switch 110. The above mentioned frequency controlling circuit 89 is connected at the output end to a sine wave generating circuit 95 at the control input end. The above mentioned sine wave generating circuit 95 is connected at the output end to a 90 degree phase shifter 96, the above mentioned 270 degree phase shifter 97 and an amplifier 98 at the input ends through the above mentioned switch 92. An amplifier 99 is connected at the input end to the above mentioned 90 degree phase shifter 96 at the output end through the above mentioned switch 93 and to the above mentioned 270 degree phase shifter 97 at the output end through the above mentioned switch 94. The above mentioned amplifiers 98 and 99 are connected at the output ends to a USM 12.

The operation of the thus formed USM controlling circuit shall be explained.

When the above mentioned contact pressure sensor 40 pasted to the upper part of the above mentioned insertable part 4 contacts such part to be inspected as a part within a body cavity, the above mentioned U terminal will be of "H", the above mentioned V terminal will be of "L" and the above mentioned W terminal will be of "H". Therefore, the output of the above mentioned 109 will be of "L" because the input end connected to the above mentioned U terminal will be of "H". Therefore, the above mentioned AND circuit 101 will be of "L" at the output end because, even if the input end connected to the above mentioned P terminal is of "H" or "L", the input end connected to the output end of the above mentioned inverter terminal 109 will be of "L". Also, the above mentioned AND circuit 102 will be of "L" at the output end because, even if the input end connected to the above mentioned Q terminal is of "H" or "L", the input end connected to the output end of the above mentioned inverter 109 will be of "L". The above mentioned AND circuit 103 will be of "L" at the output end because, even if the input end connected to the above mentioned R terminal is of "H" or "L", the input end connected to the output end of the above mentioned inverter 109 will be of "L".

Also, the above mentioned OR circuit 106 will be of "H" at the output end because, even if the input end connected to the output end of the above mentioned AND circuit 101 is of "L", the input end connected to the above mentioned U terminal will be of "H". Thereby, the above mentioned switch 92 will be ON because the control end H connected to the output end of the above mentioned OR circuit will be of "H".

The above mentioned switch 104 will be OFF because the control end N connected to the output end of the above mentioned AND circuit 102 will be of "L". The above mentioned switch 105 will be OFF because the control end O connected to the output end of the above mentioned AND circuit 103 will be of "L". However, the above mentioned switch 110 will be ON because the control end P connected to the above mentioned U terminal will be of "H". Therefore, the voltage of the above mentioned variable resistance 111 at the intermediate point will be applied to the above mentioned frequency controlling circuit 89 at the input end.

The above mentioned OR circuit 108 will be of "H" at the output end because, even if the input end connected to the output end of the above mentioned AND circuit 103 is of "L", the input end connected to the above mentioned W terminal will be of "H". Therefore, the above mentioned switch 94 will be ON because the control end J connected to the above mentioned OR circuit 108 will be of "H".

However, the above mentioned OR circuit 107 will be of "L" at the output end because the input end connected to the output end of the above mentioned AND circuit 102 will be "L" and the input end connected to the above mentioned V terminal will be also of "L". Therefore, the above mentioned switch 93 will be OFF because the control end I connected to the above mentioned OR circuit 107 will be of "L".

That is to say, in this embodiment, the same as in the first embodiment, when the above mentioned contact pressure sensor 40 pasted to the upper part of the above mentioned insertable part 4 contacts such part to be inspected as a part within a body cavity, the output of the sine wave generating circuit 92 will be applied to the above mentioned USM 12 through the above mentioned amplifier 98, 270 degree phase shifter 97 and amplifier 99 and the above mentioned USM 12 will rotate at a speed set by the above mentioned variable resistance 111 so as to bend the above mentioned bendable part 8 downeard.

When the above mentioned U terminal is of "H", even if the above mentioned P to R terminals are of "H", the control of the above mentioned USM 12 will not be influenced. That is to say, the control of the contact pressure detecting circuit will be preferred to the control of the bending switch controlling circuit.

Also, when the above mentioned contact pressure sensor 41 pasted to the lower part of the above mentioned insertable part 4 contacts such part to be inspected as a part within a body cavity, the above mentioned U terminal will be of "H", the above mentioned V terminal will be of "H" and the above mentioned W terminal will be of "L". Therefore, the output of the above mentioned inverter 109 will be of "L" because the input end connected to the above mentioned U terminal will be of "H". Therefore, the above mentioned AND circuit 101 will be of "L" at the outpue end because, even if the input end connected to the above mentioned P terminal is of "H" or "L". the input end connected to the output end of the above mentioned inverter 109 will be of "L". The above mentioned AND circuit 102 will be of "L" at the outpue end because, even if the input end connected to the above mentioned Q terminal is of "H" or "L", the input end connected to the output end of the above mentioned inverter 109 will be of "L". The above mentioned AND circuit 103 will be of "L" at the outpue end because, even if the input end connected to the above mentioned R terminal is of "H" or "L", the input end connected to the output end of the above mentioned inverter 109 will be of "L".

The above mentioned OR circuit 106 will be of "H" at the output end because, even if the input end connected to the output end of the above mentioned AND circuit 101 is of "L", the input end connected to the above mentioned U terminal will be of "H". Thereby, the above mentioned switch 92 will be ON because the control end H connected to the output end of the above mentioned OR circuit 106 will be of "H".

Also, the above mentioned switch 104 will be OFF because the control end N connected to the output end of the above mentioned AND circuit 102 will be of "L". The above mentioned switch 105 will be OFF because the control end O connected to the output end of the above mentioned AND circuit 103 will be of "L". However, the above mentioned switch 110 will be ON because the control end P connected to the above mentioned U terminal will be of "H". Therefore, the voltage of the above mentioned variable resistance at the intermediate point will be applied to the above mentioned frequency controlling circuit 89 at the input end.

The above mentioned OR circuit 107 will be of "H" at the output end because, even if the input end connected to the output end of the above mentioned AND circuit 102 is of "L", the input end connected to the above mentioned V terminal will be of "H". Therefore, the above mentioned switch 93 will be ON because the control end I connected to the above mentioned OR circuit 107 will be of "H".

However, the above mentioned OR circuit 108 will be of "L" at the output end because the input end connected to the output end of the above mentioned AND circuit 103 will be of "L" and the input end connected to the above mentioned W terminal will be also of "L". Therefore, the above mentioned switch 94 will be OFF because the control end J connected to the above mentioned OR circuit 108 will be of "L".

Therefore, the same as in the first embodiment, when the above mentioned contact pressure sensor 41 pasted to the upper part of the above mentioned insertable part 4 contacts such part to be inspected as a part within a body cavity, the output of the above mentioned sine wave generating circuit 95 will be applied to the above mentioned USM 12 through the above mentioned amplifier 98, 90 degree phase shifter 96 and amplifier 99 and the above mentioned USM 12 will rotate at a speed set by the above mentioned variable resistance 111 so as to bend the above mentioned bendable part 8 upward.

When the above mentioned contact pressure sensor 40 pasted to the upper part of the above mentioned insertable part 4 and the above mentioned contact pressure sensor 41 pasted to the lower part are not in contact with such part to be inselected as a part within a body cavity, if the above mentioned lever 28 of the above mentioned bending switch 16 is inclined so that the above mentioned bendable part 8 may bend upward, the above mentioned P terminal will be of "H", the above mentioned Q terminal will be of "H", the above mentioned R terminal will be of "L", the above mentioned U to W terminals will be of "L" and the above mentioned S terminal will be of a voltage corresponding to the inclination of the above mentioned lever 28. Therefore, the above mentioned inverter 109 will be of "H" because the input end connected to the above mentioned U terminal will be of "L". Thereby, the above mentioned AND circuit 101 will be of "H" at the output end because the input end connected to the above mentioned P terminal will be of H" and the input end connected to the output end of the above mentioned inverter 109 will be also of "H". Also, the above mentioned AND circuit 102 will be of "H" at the output end because the input end connected to the above mentioned Q terminal will be of "H" and the input end connected to the output end of the above mentioned inverter 109 will be also of "H". The above mentioned AND circuit 103 will be of "L" at the output end because the input end connected to the above mentioned R terminal will be of "L" and even if the input end connected to the output end of the above mentioned inverter 109 is of "H".

Also, the above mentioned OR circuit 106 will be of "H" at the output end because the input end connected to the output end of the above mentioned AND circuit 101 will be of "H" and even if the input end connecated to the above mentioned U terminal is of "L". Thereby, the above mentioned switch 92 will be ON because the control end H connected to the output end of the above mentioned OR circuit 106 will be of "H".

The above mentioned switch 105 will be OFF because the control end 0 connected to the output end of the above mentioned AND circuit 103 will be of "L". The above mentioned switch 110 will be OFF because the control end P connected to the above mentioned U terminal will be "L". However, the above mentioned switch 104 will be ON because the the control end N connected to the output end of the above mentioned AND circuit 102 will be of "H". Therefore, the voltage of the above mentioned S terminal will be applied to the above mentioned frequency controlling circuit 89 at the input end.

The above mentioned OR circuit 107 will be of "H" at the output end because the input end connected to the output end of the above mentioned AND circuit 102 will be of "H" and even if the input end connected to the above mentioned V terminal is of "L". Therefore, the above mentioned switch 93 will be ON because the control end I connected to the output end of the above mentioned OR circuit 107 will be of "H".

However, the above mentioned OR circuuit 108 will be of "L" at the output end because the input end connected to the above mentioned AND circuit 103 will be of "L" and the input end connected to the above mentioned W terminal will be also of "1". Therefore, the above mentioned switch 94 will be OFF because the control end J connected to the output end of the above mentioned OR circuit 108 will be of "L".

That is to say, the same as in the first embodiment, when the above mentioned lever 28 of the above mentioned bending switch 16 is bent so that the above mentioned bendable part 8 may bend upward, the output of the sine wave generating circuit 92 will be applied to the above mentioned USM 112 through the above mentioned amplifier 98, 90 degree phase shifter 96 and amplifier 99 and the above mentioned USM 12 will rotate at a speed corresponding to the inclination of the above mentionend lever 28.

When the above mentioned lever 28 of the above mentioned bending switch 16 is inclined so that the above mentioned bendable part 8 may bend downward, the above mentioned P terminal will be of "H", the above mentioned Q terminal will be of "L", the above mentioned U to W terminals will be of "L" and the above mentioned T terminal will be of a voltage corresponding to the inclination of the above mentioned lever 28. Therefore, the above mentioned inverter 109 will be of "H" at the output end because the input end connected to the above mentioned U terminal will be of "L". Thereby, the above mentioned AND circuit 101 will be of "H" at the output end because the input end connected to the above mentioned P terminal will be of "H" and the input end connected to the output end of the above mentioned inverter 109 will be also of "H". The above mentioned AND circuit 102 will be of "L" at the output end because the input end connected to the above mentioned Q terminal will be of "L" and even if the input end connected to the output end of the above mentioned inverter 109 is of "H". The above mentioned AND circuit 103 will be of "H" at the output end because the input end connected to the above mentioned R terminal will be of "H" and the input end connected to the output end of the above mentioned inverter 109 will be also of "H".

Also, the above mentioned OR circuit 106 will be of "H" at the output end because the input end connected to the output end of the above mentioned AND circuit 101 will be of "H" and even if the input end connected to the above mentioned U terminal is of "L". Thereby, the above mentioned switch 92 will be ON because the control end H connected to the output end of the above mentioned OR circuit 106 will be of "H".

The above mentioned switch 104 will be OFF because the control end N connected to the output end of the above mentioned AND circuit 102 will be of "L". The above mentioned switch 110 will be OFF because the control end P connected to the above mentioned U terminal will be of "L". However, the above mentioned switch 105 will be ON because the control end O connected to the output end of the above mentioned AND circuit 103 will be of "H". Therefore, the voltage of the above mentioned T terminal will be applied to the above mentioned frequency controlling circuit 89 at the input end.

The above mentioned OR circuit 107 will be of "L" at the output end because the input end connected to the output end of the above mentioned AND circuit 102 will be of "L" and the input end connected to the above mentioned V terminal will be also of "L". Therefore, the above mentioned switch 93 will be, OFF because the control end I connected to the output end of the above mentioned OR circuit 107 will be of "L".

However, the above mentioned OR circuit 108 will be of "H" at the output end because the input end connected to the above mentioned AND circuit 103 will be of "H" and even if the input end connected to the above mentoned W terminal is of "L". Therefore, the above mentioned switch 94 will be ON because the control end J connected to the output end of the above mentioned OR circuit 108 will be of "H".

That is to say, the same as in the first embodiment, when the above mentioned lever 28 of the above mentioned bending switch 16 is inclined so that the above mentioned bendable part 8 may bend downward, the output of the sine wave generating circuit 92 will be applied to the above mentioned USM 12 through the above mentioned amplifier 98, 270 degree phase shifter and amplifier 99 and the above mentioned USM 12 will rotate at a speed corresponding to the inclination of the above mentioned lever 28 so as to bend the above mentioned bendable part 8 downward.

The essential parts of the above described operations of the above mentioned bending switch controlling circuit 21, contact pressure detecting circuit 26 and USM controlling circuit 22 are shown in Table 2. By the way, in the table, "UD" represents an operating direction of the above mentioned bendable part 8 by the above mentioned bending switch 16, "P" to "T" represent logical values or potentials of the terminals of the bending switch controlling circuit, "Contact" represents detecting directions of the above mentioned contact pressure sensors 40 and 41, "U" to "W" represent logical values of the terminals of the contact pressure detecting circuit, 104, 105, 110, 92, 93 and 94 represent the states of the respective switches of the above mentioned USM controlling circuit 22 and "S" and "T" represent by the blanks zero potential and OFF states of the switches.

power source, is earthed at the other end through a resistance 203 and is connected to a ring counter 210 at the control end x. A VCO (voltage controlled oscillator) 204 is connected at the output end through the above mentioned analogue switch 205 to the above mentioned ring counter which is a serial-in/parallel-out 4-bit right and left shift register at the clock end a and is connected to a monostable multivibrator (mentioned as a monomulti hereinafter) 206 at the input end. The above mentioned monomulti 206 is connected at the output end to a saw tooth generating circuit 207 at the input end. The above mentioned saw tooth generating circuit 207 is formed, for example, of resistances 207b, 207c and 207f, capacitors 207a and 207g, a diode 207d and a transistor 207e. A speed controlling volume 209 is earthed at one end, is connected at the other end to an electric power source and is connected at the intermediate point g to a comparator 208 at the irreversible input end. The above mentioned comparator 208 is connected at the irreversible input end with the above mentioned speed controlling volume 209 at the intermediate point g and is connected at the reversible input end with the above mentioned saw tooth generating circuit 207 at the output end. The above mentioned ring counter 210 is connected at the output ends b, c, d and e respectively to AND circuits 211, 212, 213 and 214 at the first input ends. The above mentioned comparator 208 is connected at the outpput end to the above mentioned AND circuits 211, 212, 213 and 214 at the second input ends. The above mentioned AND circuits 211, 212, 213 and 214 are connected at the output ends to a switching circuit 215 at the input ends. The above mentioned

TABLE 2

| UD | P | Q | R | S | T | 105 | 110 | 92 | 93 | 94 | Contact | U | V | W | 104 |
|---|---|---|---|---|---|---|---|---|---|---|---|---|---|---|---|
| Central | L | L | L | | | | | ON | ON | | None | L | L | L | |
| Central | L | L | L | | | | ON | ON | | ON | Upward | H | L | H | |
| Central | L | L | L | | | | ON | ON | ON | | Downward | H | H | L | |
| Upward | H | H | L | υ | | | | ON | ON | | None | L | L | L | ON |
| Upward | H | H | L | υ | | | ON | ON | | ON | Upward | H | L | H | |
| Downward | H | L | H | | υ | ON | | ON | | ON | None | L | L | L | |
| Downward | H | L | H | | υ | | ON | ON | ON | | Downward | H | H | L | |

In the thus formed second embodiment, there are effects that, even while the above mentioned bending switch 16 is being operated, the above mentioned tip part 7 will contact on the side part with such part to be inspected as a part within a body cavity under a predetermined pressure, the above mentioned bendable part 8 will be bent under a bending resistance, the above mentioned tip part 7 will be moved in the direction of reducing the bending resistance and there will be no fear of hurting the inspected part with the above mentioned tip part 7.

Figure 6:
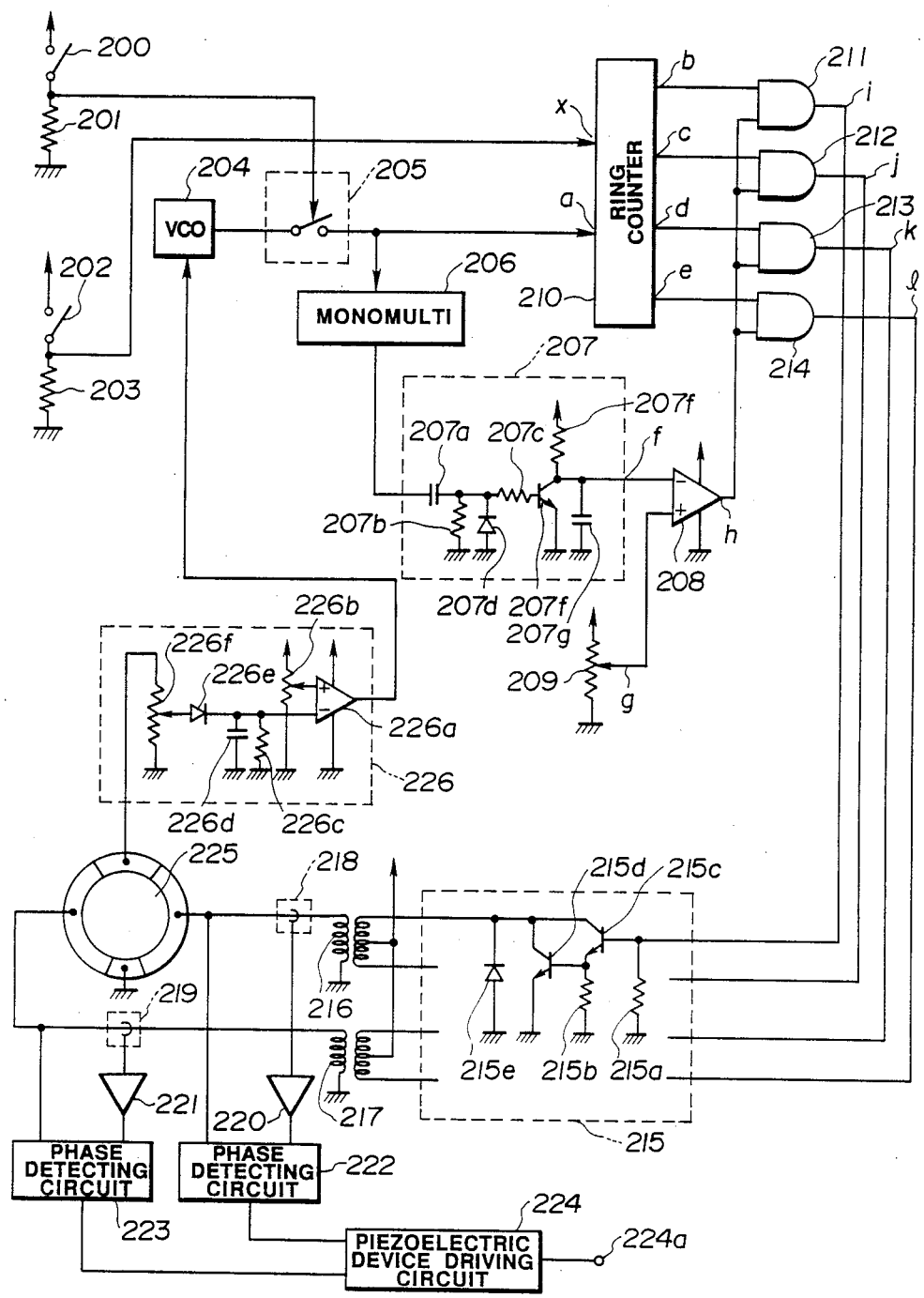
FIGS. 6 to 8 relate to the third embodiment of the present invention.
Figure 7:
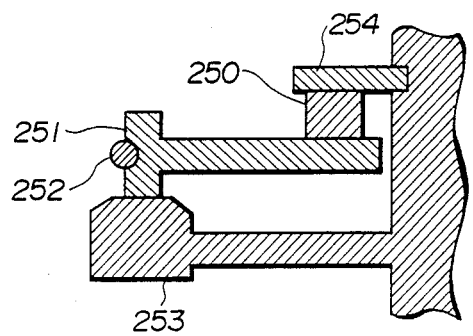

In FIGS. 6 to 8 is shown the third embodiment of the present invention.

FIG. 6 shows the formation of the above mentioned USM controlling circuit for controlling the USM in the vertical direction. The above mentioned USM controlling circuit for controlling the USM in the horizontal direction is the same as in the vertical direction and shall not be described here.

A bending ON/OFF switch (which shall be mentioned as a bending switch hereinafter) 200 is connected at one end with an electric power source, is earthed at the other end through a resistance 201 and is connected to an analogue switch 205 at the control end. A bending direction switch (mentioned as a direction switch hereinafter) 202 is connected at one end with an electric switching circuit 215 is formed of four Darlington circuits (only one formation is illustrated) each formed, for example, of resistances 215a and 215b, transistors 215c and 215d and a diode 215e. The above mentioned switching circuit 215 is push-pull connected at the output end to transistors 216 and 217 on the primary sides. The above mentioned transistors 216 and 217 are connected at the intermediate points to an electric power source. The above mentioned transistors 216 and 217 on the secondary sides are earthed at one end and are connected at the other end to a USM 225 through current probes 218 and 219 and are connected to phase detecting circuits 222 and 223 at the first input ends. The above mentioned current probes 218 and 219 are connected at the output ends to amplifiers 220 and 221 at the input ends. The above mentioned amplifiers 220 and 221 are connected at the output ends to the above mentioned phase detecting circuits 222 and 223 at the second input ends. The above mentioned phase detecting circuits 222 and 223 are connected at the output ends to a piezoelectric device driving circuit 224 at the first and second input ends. The above mentioned piezoelectric device driving circuit 224 is connected at the output end 224a to a piezoelectric device 250 shown in FIG. 7. A feedback circuit 226 is connected at the input end to the above mentioned USM 225 and is connected at the output end to the above mentioned VCO 204 at the input end. The above mentioned feedback circuit 226 is formed, for example, of variable resistances 226f and 226b, a resistance 226c, capacitor 226d, dioide 226e and comparator 226a.

FIG. 7 is a sectioned view of an essential part of the above mentioned USM 225. A rotor 251 is pressed by the above mentioned piezoelectric device 250 into contact with a stator 253. A wire 252 is fixed on the periphery of the above mentioned rotor 251. The above mmentioned piezoelectric device 250 is fixed by an E-ring 254 which is engaged with the stator 253.

The operation of the thus formed above mentioned USM controlling circuit shall be explained.

When the above mentioned bending switch 200 is ON, an electric current will flow through the above mentioned resistance 201 which will be of "H" at the point in contact with the above mentioned analogue switch 205 at the control end. Therefore, the above mentioned analogue switch 205 will be ON. Thereby, an output signal of a waveform shown, for example, in FIG. 8(a) of the above mentioned VCO 204 will be input into the above mentioned ring counter 210 at the clock terminal a through the above mentioned analogue switch 205. The same output signal of the above mentioned VCO 204 will be input also into the above mentioned monomulti 206 at the input end.

Figure 8A:
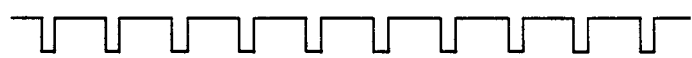
Figure 8B:
Figure 8C:
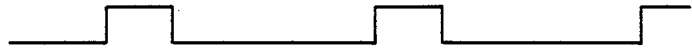
Figure 8D:
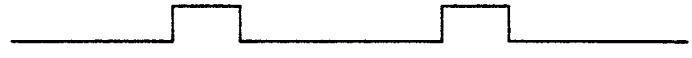
Figure 8E:
Figure 8F:
Figure 8G:
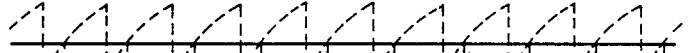
Figure 8H:
Figure 8I:
Figure 8J:
Figure 8K:
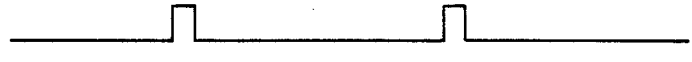
Figure 8L:

At the same time, when the above mentioned direction switch 202 is ON, an electric current will flow through the above mentioned resistance 203 which will be of "H" at the point in contact with the above mentioned ring counter 210 at the control end x. Thereby, in the above mentioned ring counter 210, as the control end x will be of "H", as shown in FIGS. 8(a) to (e), at the time point when the input signal at the clock end a falls from "H" to "L", "H" will be output at the output ends b to d sequentially in the order of b, c, d and e. Also, the above mentioned monomulti 206 will control the above mentioned saw tooth generating circuit 207 with the output signal of the above mentioned VCO 204 shown in FIG. 8(a) and the above mentioned saw tooth generating circuit 207 will output the saw tooth signal shown in FIG. 8(f). Thereby, as shown in FIG. 8(g), the above mentioned comparator 208 will compare the output signal of the above mentioned saw tooth generating circuit 207 connected at the reversible input end and the voltage at the intermediate point g of the above mentioned speed controlling volume connected at the irreversible input end with each other and, as shown in FIG. 8(h), will output a signal which will be of "H" for the period when the output signal of the above mentioned saw tooth generating circuit 207 is lower than the voltage of the above mentioned speed controlling volume 209.

Also, as shown in FIGS. 8(i) to (l). the above mentioned AND circuits 211, 212, 213 and 214 will be of "H" at the output ends when the input end connected to the above mentioned ring counter 210 is of "H" and the input end connected to the above mentionend comparator 208 is also of "H". That is to say, a PWM (pulse width modulating) circuit is formed of the above mentioned monomulti 206, saw tooth generating circuit 207, comparator 208 and AND circuits 211, 212, 213 and 214.

Thereby, the above mentioned switching circuit 215 will feed sine waves and cosine waves, for example, of 100 V rms to the above mentioned USM 225 through the above mentioned transistors 216 and 217 and the above mentioned stator 253 of the above mentioned USM 225 will rotate in the direction of bending the bendable part upward at a speed corresponding to the period of "H" of the output pulses of the above mentioned AND circuits 211, 212, 213 and 214. By the way, in order to efficiently drive the above mentioned USM 225, the above mentioned VCO 204 is made by the control of the above mentioned feedback circuit 226 to output a signal of a frequency somewhat higher than the resonance frequency of the above mentioned USM 225.

When the above mentioned direction switch 202 is OFF, no current will flow through the above mentioned resistance 203 and the above mentioned ring counter 210 will be of "L" at the control end x. Thereby, in the above mentioned ring counter 210, as the control end x will be of "L", "H" will be output at the output ends b to d sequentially in the order of e, d, c and b. By the way, the above mentioned AND circuits 211, 212, 213 and 214, switching circuit 215 and transistors 216 and 217 will operate the same as in the case of bending the bendable part upward. However, the shift of "H" of the ring counter at the output ends will be reverse to the upward case and therefore the above mentioned stator of the above mentioned USM 225 will rotate in the direction of bending the bendable part downward at a speed corresponding to the period of "H" of the output pulses of the above mentioned AND circuits 211, 212, 213 and 214.

Now, in case the above mentioned USM 225 is in a non-loaded state, that is, there is no bending resistance, the electric power fed to the above mentioned USM 225 will be of a phase difference of 90 degrees between the voltage and current. However, the larger the load, the smaller the phase difference between the voltage and current.

Therefore, in this embodiment, the voltages fed from the above mentioned transisters 216 and 217 on the secondary sides are input into the above mentioned phase difference detecting circuits 222 and 223 and the currents fed to the above mentioned USM 225 are detected by the above mentioned current probes 218 and 219 and are input into the above mentioned phase detecting circuit 222 and 223 through the above mentioned amplifiers 220 and 221.

Thereby, the above mentioned phase difference detecting circuits 222 and 223 will judge the phase difference between the voltage and current. If the phase difference is, for example, below 5 degrees, they will judge that the above mentioned USM 225 will be overloaded, that is, that the bending resistance will be very large and will output signals to the above mentioned piezoelectric device driving circuit 224.

The above mentioned piezoelectric device driving circuit 224 will drive the above mentioned piezoelectric device 250 in the extending direction in case the signals from the above mentioned phase detecting circuits 222 and 223 are not input but will drive the above mentioned piezoelectric device 250 in the contracting direction in case the signals from the above mentioned phase detecting circuits 222 and 223 are input.

That is to say, in case the above mentioned USM 225 is in a non-loaded state of no bending resistance, the above mentioned piezoelectric device 250 will press the above mentioned rotor 251 into contact with the above mentioned stator 253 and the above mentioned rotor 251 will be operatively connected with the above mentioned stator 253 and will push and pull the above mentioned wire 252 but, in case the above mentioned USM 225 is in an overloaded state of a very large bending resistance, the above mentioned piezoelectric device 250 will disengage the above mentioned rotor 251 and stator 253 with each other and the above mentioned wire 252 will become free.

By the way, by being provided either with the above mentioned current probe 218, amplifier 220 and phase detecting circuit 222 or with the above mentionend current probe 219, amplifier 221 and phase detecting circuit 223, the same operation can be obtained.

Further, the means for releasing the pressed contact (energizing force) of the rotor and stator of the USM may be made, for example, of a form memorizing alloy.

This embodiment has also the same effects as of the above described second embodiment.

Figure 9:
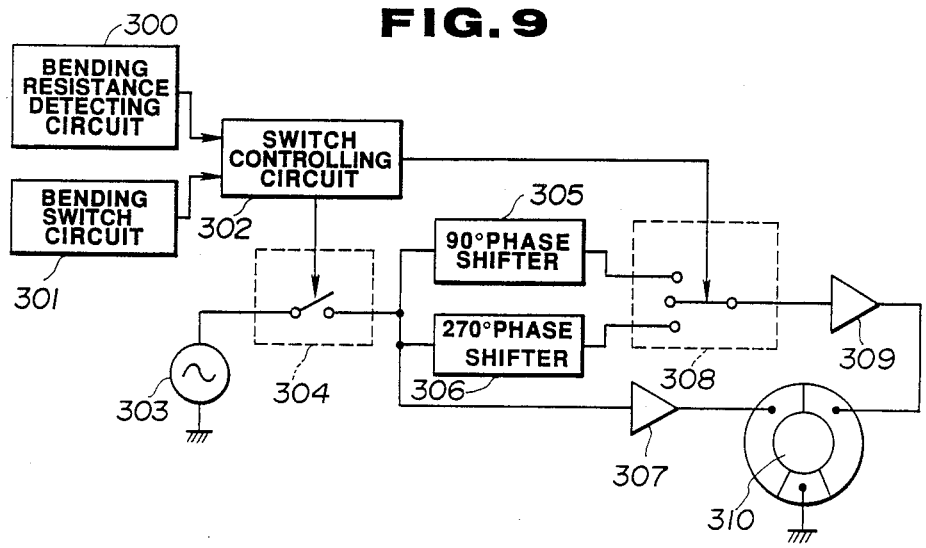
FIG. 9 relates to the fourth embodiment of the present invention.

In FIG. 9 is shown the fourth embodiment of the present invention. By the way, the above mentioned USM controlling circuit in the vertical direction is shown and the above mentioned USM controlling circuit in the horizontal direction is of the same formation and shall not be described here.

A switch controlling circuit 302 is connected at the input end with a bending resistance detecting circuit 300 and bending switch circuit 301 and is connected at the output ends with a switch 304 at the control end and a switch 308 at the control end. A sine wave generating circuit 303 is connected at the output end with a 90 degree phase shifter 305, 270 degree phase shifter 306 and amplifier 307 at the inpput ends through the above mentioned switch 304. The above mentionend 90 degree phase shifter 305 and 270 degree phase shifter 306 are connected at the output ends to an amplifier 309 at the input end through the above mentioned switch 308. The above mentioned amplifiers 307 and 309 are connected at the output ends to a USM 310.

The operation of the thus formed USM controlling circuit shall be explained.

When the bending switch is operated, the above mentioned bending switch circuit 301 will output a signal corresponding to the bending direction to the above mentioned switch controlling circuit 302 which will switch ON the above mentioned switch 304 even if the bending directiion is upward or downward. Thereby, the output of the above mentioned sine wave generating circuit 303 will be input into the above mentioned 90 degree phase shifter 305, 270 degree phase shifter 306 and amplifier 307 at the input ends through the above mentioned switch 304. The above mentioned switch controlling circuit 302 will control the above mentioned switch 308 to connect the above mentioned amplifier 309 with the above mentioned 90 degree phase shifter 305 if the output of the above mentioned bending switch circuit 301 is an upward bending signal but will control the above mentioned switch 308 to connect the above mentioned amplifier 309 with the above mentioned 270 degree phase shifter 306 if the output of the above mentioned bending switch circuit 301 is a downward bending signal.

Therefore, either one of the output of the above mentioned amplifier 307 and the output of the above mentioned 90 degree phase shifter 305 or 270 degree phase shifter through the above mentioned switch 308 will be applied to the above mentioned USM 310. Thereby, the above mentioned USM 310 will rotate in the direction of bending the bendable part upward if the output of the above mentionend amplifier 307 and the output of the above mentioned 90 degree phase shifter 305 are applied but will rotate in the direction of bending the bendable part downward if the output of the above mentioned amplifier 307 and the output of the above mentioned 270 degree phase shifter 306 are applied.

However, when the above mentioned bending resistance detecting circuit 300 detects a bending resistance, the above mentioned bending resistance detecting circuit 300 will output a signal to the above mentioned switch controlling circuit 302. Thereby, the above mentioned switch controlling circuit 302 will control the above mentioned switch 308 to be neutral, that is, to open the above mentioned amplifier 309 at the input end.

Therefore, only the signal of the above mentioned sine wave generating circuit 303 through the above mentioned switch 304 and amplifier 307 will be applied to the above mentioned USM 310. Thereby, only a standing wave will be generated in the above mentioned USM 310. As a result, the holding torque of the above mentioned USM 310 will greatly reduce.

That is to say, when the holding torque of the above mentioned USM 310 reduces, the bendable part held by the above mentioned USM 310 will become free.

In case the bending switch is not operated, that is, in case the above mentioned switch 304 is OFF and the above mentioned switch 308 is neutral, when the above mentioned bending resistance detecting circuit 300 detects a bending resistance, the above mentioned bending resistance detecting circuit 300 will output a signal to the above mentioned switch controlling circuit 302. Thereby, the above mentioned switch controlling circuit 302 will control the above mentioned switch 304 to be ON.

Therefore, only the signal of the above mentioned sine wave generating circuit 303 through the above mentioned switch 304 and amplifier 307 will be applied to the above mentioned USM 310. Thereby, a standing wave will be generated in the above mentioned USM 310. As a result, the holding torque of the above mentioned USM 310 will greatly reduce.

That is to say, when the holding torque of the above mentioned USM 310 reduces, the bendable part held by the above mentioned USM 310 will become free.

The effects of this embodiment are also the same as the effects of the second to fourth embodiments.

Figure 10:
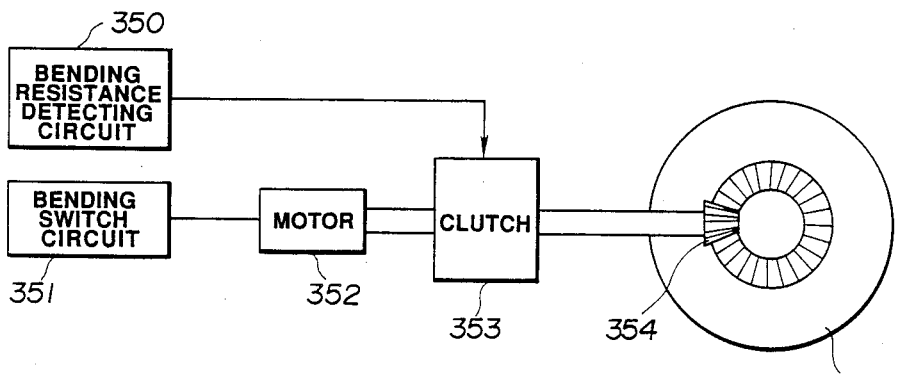
FIG. 10 relates to the fifth embodiment of the present invention.

In FIG. 10 is shown the fifth embodiment of the present invention. By the way, a bending motor controlling circuit in the vertical direction is shown. A bending motor controlling circuit in the horizontal direction is the same as in the vertical direction and shall not be described here.

The bending motor controlling circuit is formed of a bending resistance detecting circuit 350, bending switch circuit 351, motor 352 which is, for example, an electromagnetic motor, clutch 353, gear 354 and pulley 355.

The operation of the thus formed bending motor controlling circuit shall be explained.

The above mentioned motor 352 will be stopped and normally and reversely rotated by a control signal of the above mentioned bending switch circuit 351. The torque of the above mentioned motor 351 will be transmitted to the above mentioned gear 354 through the above mentioned clutch 353 and will rotate the above mentioned pulley 355.

However, when the above mentioned bending resistance detecting circuit 350 detects a bending resistance, a signal will be output to the above mentioned clutch 353. Thereby, the above mentioned clutch 353 will stop the transmission of the torque of the motor 351 to the above mentioned gear 354. Therefore, the above mentioned gear 354 and pulley 355 will become free.

That is to say, the bendable part held by the above mentioned motor 352 will become free.

The effects of this embodiment are also the same as the effects of the second to fourth embodiments.

Figure 11:
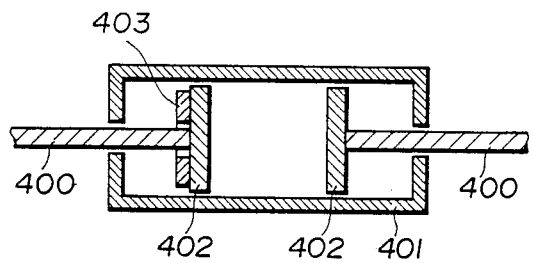
FIG. 11 is a sectioned view of a means for detecting a bending resistance.

By the way, the means for detecting a bending resistance is not limited to the one shown in the first to fifth embodiments but may be a pressure sensor 403 pasted to at least one of removal preventing stoppers 402 provided at the ends of bending wires 400 within a relaxation removing mechanism 401 provided in the intermediate part of the bending wires as shown, for example, in FIG. 11.

Figure 12:
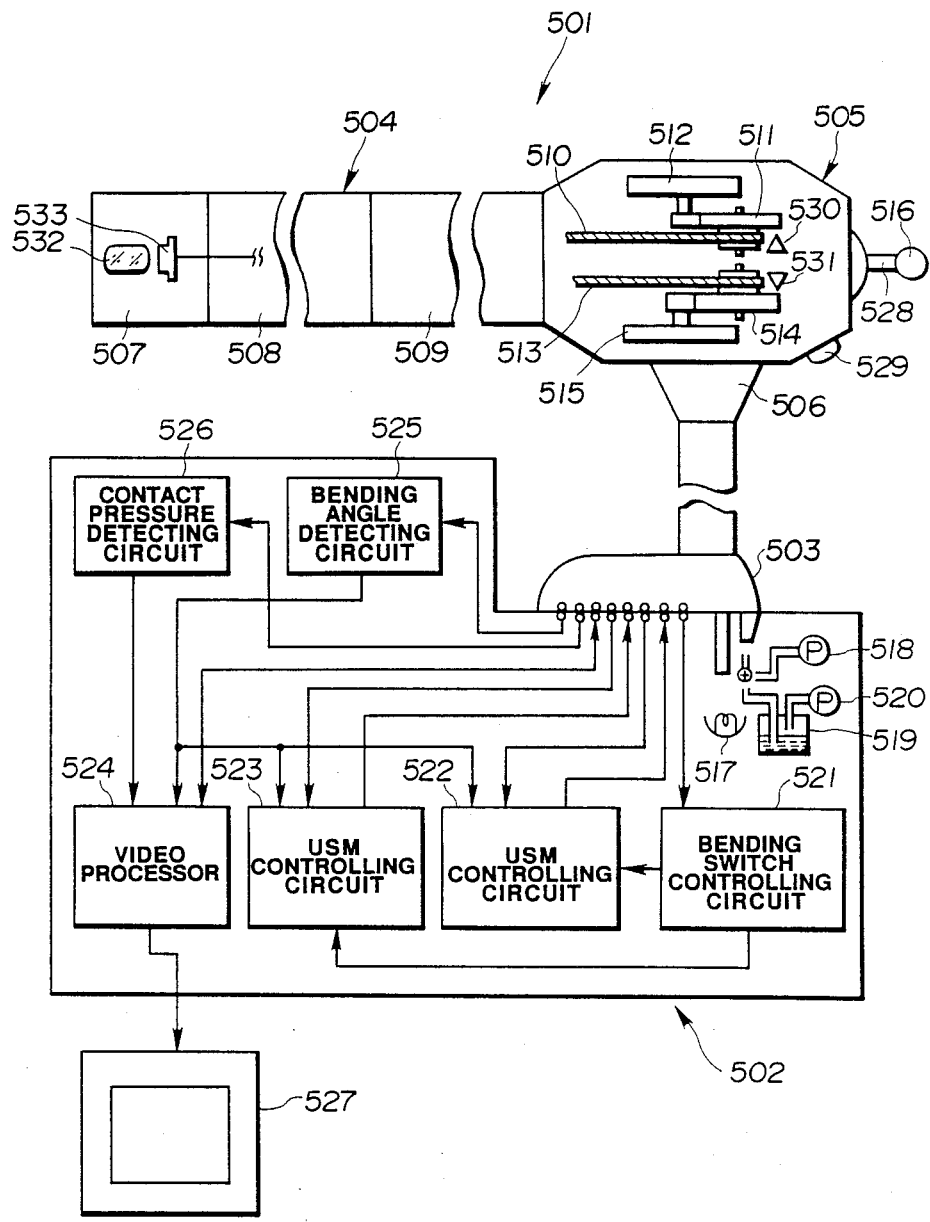
Figure 13:
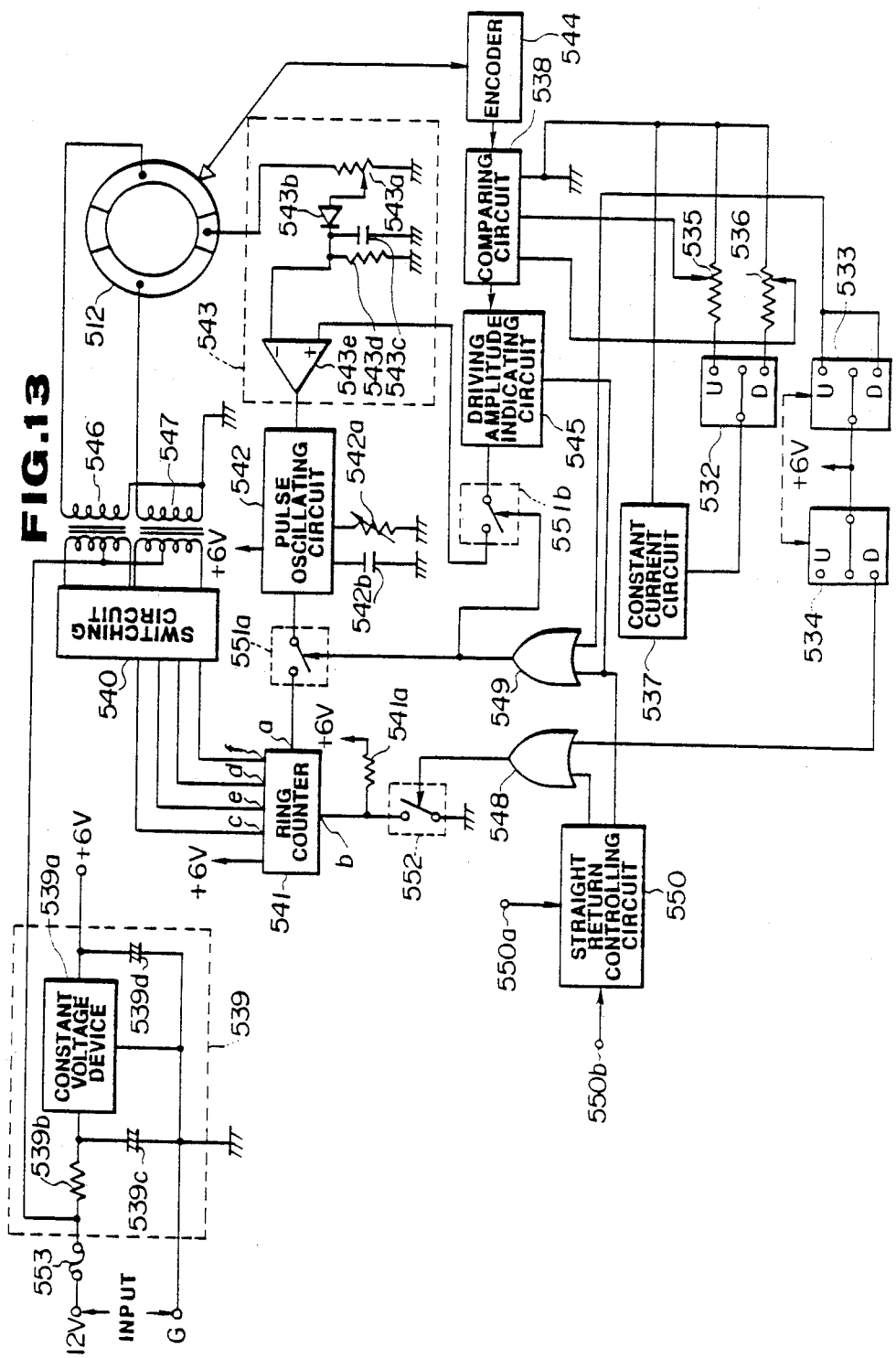

In FIGS. 12 to 14 is shown the sixth embodiment of the present invention.

As shown in FIG. 12, an endoscope apparatus comprises an endoscope 501 formed to be elongate so as to be able to be inserted, for example, into a body cavity, a universal control apparatus (mentioned as a UCA hereinafter) 502 to which a universal cord 506 of the above mentioned endoscope 501 is connected by a connector 503 and a monitor 527 in which such imaged object as a part within a body cavity is displayed by an output signal of a video processor 524 provided within the above mentioned UCA 502.

The above mentioned endoscope 501 comprises, for example, an elongate flexible insertable part 504, a thick holding part 505 connected to the above mentioned insertable part 504 at the rear end, a flexible universal cable extended sidewise of the above mentioned holding part 505 and a connector 503 provided at the end of the above mentioned universal cable 506. The above mentioned insertable part 504 comprises a rigid tip forming part in which an imaging device for imaging an object to be imaged is arranged, a bendable part 508 bendable vertically/horizontally and connected to the above mentioned tip forming part 507 at the rear end and a flexible tube part 509 connected to the above mentioned bendable part 508 at the rear end.

An objective lens 532 is provided in the above mentioned tip forming part 507. A solid state imaging device 533 is arranged in the image forming position of the above mentioned objective lens 532. A signal line not illustrated provided within the endoscope 501 is connected to the above mentioned solid state imaging device 533 and is connected to a video processor 524 provided within the UCA 502 through the connector 503. Further, a contact pressure sensor not illustrated detecting the contact pressure when the above mentioned bendable part 508 is bent and the above mentioned tip forming part 507 contacts a body cavity interior or the like is arranged in the above mentioned tip forming part 507. A signal line not illustrated provided within the endoscope 501 is connected to the above mentioned contact pressure sennsor and is connected to a contact pressure detecting circuit 526 provided within the UCA 502 through the connector 503.

Such oscillating wave motor (mentioned as a USM hereinafter) 512 as a motor driven, for example, by an ultrasonic driving signal for pulling a bending wire 510 in the vertical direction through a reduction gear 511 and a USM 515 for pulling a bending wire 513 in the horizontal direction through a reduction gear 514 are provided within the above mentioned holding part 505. Further, rotation angle sensors 530 and 531 formed of photoreflectors or the like are provided within the above mentioned holding part 505. A signal line not illustrated provided within the universal cable 506 is connected to the above mentioned rotation angle sensors 530 and 531 and is connected to a bending angle detecting circuit 525 provided within the UCA 502 through the connector 503. A bending switch 516 for controlling the bending direction of the bendable part 508, a switch 529 for making the bendable part 508, for example, of a substantially straight bending angle and an air/water feeding button, sucking button, $CO_2$ gas feeding button, forceps raising mechanism, video processor controlling freezing and releasing switches and VTR starting switch not illustrated are provided on the sheath of the above mentioned holding part 505. A signal line not illustrated provided within the universal cable 506 is connected to the above mentioned bending switch 516 and is connected to a bending switch controlling circuit 521 provided within the UCA 502 through the connector 503. Signal lines not illustrated provided within the universal cable 506 are connected to the above mentioned switch 529 and are to be connected to the USM controlling circuits 522 and 523 provided within the UCA 502 through the connector 503.

Also, within the above mentioned endoscope 501 are provided a light guuide fiber, air/water feeding tube and treating instrument channel.

The above mentioned UCA 502 may be provided with a lamp 517 feeding an illuminating light to the above mentioned light guide fiber, an air feeding pump 518 feeding air to the above mentioned air/water feeding tube, a water feeding pump 520 for feeding water to the above mentioned air/water feeding tube, a water feeding tank storing, for example, water which is a fluid for feeding water, a bending switch controlling circuit 521 for controlling the above mentioned bonding switch 516, USM controlling circuits 522 and 5232 for controlling the above mentioned USM 512 and 515, a video processor 524 for converting the imaging signal of the above mentioned solid state imaging device 533, processing various signals and outputting them as video signals to the above mentioned monitor 527, a bending angle detecting circuit 525 detecting the bending angle of the above mentioned bendable part 508 and a contact pressure detecting circuit 526 processing the signal of the above mentioned contact pressure sensor. By the way, the UCA 502 may be of respectively separately formed apparatus as electrically and physically connected.

As described above, the above mentioned bending switch controlling circuit 521 is connected at the input end with the bending switch 516 and at the output ends with the USM controlling circuits 522 and 523.

As described above, the above mentioned bending angle detecting circuit 525 is connected at the input end with the rotation angle sensors 530 and 531 and at the output end with the USM controlling circuits 522 and 523 and video processor 524.

As described above, the above mentioned contact pressure detecting circuit 526 is connected at the input end with a contact pressure sensor not illustrated and at the output end with the video processor 524.

The above mentioned USM controlling circuit 522 is connected at the output end with the above mentioned USM 512 by a signal line not illustrated provided within the above mentioned universal cable 506 through the connector 503. The above mentioned USM controlling circuit 523 is connected at the output end with the above mentioned USM 515 by a signal line not illustrated provided within the above mentioned universal cable 506 through the above mentioned connector 503.

Now, the above mentioned bending switch 516 is of a joy stick type form and comprises a switch controlling the bending direction of the above mentioned bendable part 508 by inclining the lever 528, for example, vertically/horizontally and a variable resistance varying in the resistance value in response to the inclination of the lever 528. The above mentioned bending direction controlling switch comprises a switch of upward and downward bending directions and a switch of rightward and leftward bending directions. The above mentioned switch of upward and downward directions and switch of rightward and leftward directions can operate simultaneously. The above mentioned bending switch 516 is so made that the above mentioned lever 528 may be returned to the neutral position by such energizing force as of a spring.

The conncrete circuit formation of the above mentioned USM controlling circuit 522 controlling the above mentioned USM 512 is shown in FIG. 13. The above mentioned USM controlling circuit 523 controlling the above mentioned USM 515 is of the same formation and operation as of the above mentioned USM controlling circuit and therefore shall not be described here. By the way, the case that the bending indicating direction is upward shall be represented by "U" and the case that it is downward shall be represented by "D". In the USM controlling circuit 523, there shall be re-read "upward" as "rightward", "downward" as "leftward", U as R, D as L, the USM 512 as the USM 515, the reduction gear 511 as the reduction gear 514 and the bending wire 510 as the bending wire 513.

The above mentioned bending switch 516 can be equevalently represented by switches 532, 533 and 534 and variable resistances 535 and 536. The above mentioned switch 532 is connected at the transfer end (mentioned as a T end hereinafter) to a constant current circuit 537 at one end, at the U end to the variable resistance 535 at one end and at the D end to the variable resistance 536 at one end. The above mentioned constant current circuit 537 is earthed at the other end. The above mentioned variable resistance 535 is earthed at the other end and is connected at the intermediate point to a comparing circuit 538 at the U speed setting input end. The above mentioned variable resistance 536 is earthed at the other end and is connected at the intermediate point to the comparing circuit 538 at the D speed setting input end. The above mentioned comparing circuit 538 is earthed at the earthing end. The above mentioned switch 533 is connected at the T end to a power source circuit 539 at the output end (+6V) and is connected at the U and D ends to an OR circuit 549 at the first input end. The above mentioned switches 532, 533 and 534 will not be connected at the T ends to the U and D ends in case the lever 528 of the above mentioned bending switch 516 is in the neutral position. The above mentioned switches 532, 533 and 534 will be connected at the T ends simultaneously to the U or D end.

An encoder 544 for detecting the rotation speed of the above mentioned USM 512 is arranged in the above mentioned USM 512 and is connected at the output end to the above mentioned comparing circuit 538 at the speed detecting input end. Also, the above mentioned USM 512 is connected at one end to a feedback circuit 543 at the first input end.

The above mentioned comparing circuit 538 is connected at the output end to a driving amplitude indicating circuit 545 at the indication input end. The above mentioned driving amplitude indicating circuit 545 is connected at the output end to the above mentioned feedback circuit 543 at the second input end through a switch 551b.

The above mentioned feedback circuit 543 is earthed at the first input end through a variable resistance 543a. The above mentioned variable resistance 543a is connected at the intermediate point to a diode 543b at the anode. The above mentioned diode 543b is connected at the cathode to an operating amplifier 543e at the reversible input end and is connected to a capacitor 543c and resistance 543d respectively at one end. The above mentioned capacitor 543c and resistance 543d are earthed at the other ends. The above mentioned feedback circuit 543 is connected at the second input end to the above mentioned operating amplifier 543e at the irreversible input end.

The above mentioned feedback circuit 543 is connected at output end, that the operating amplifier 543e is connected at the output end to a pulse oscillating circuit 542 at the control input end. The above mentioned pulse oscillating circuit 542 is connected at the output end to a ring counter 541 at the clock end a through a switch 551a. The above mentioned pulse oscillating circuit 542 is connected at the power source end to the above mentioned power source circuit at the output end (+6V). The capacitor 542b and variable resistance 542a connected to the above mentioned pulse oscillating circuit 542 are earthed.

The above mentioned ring counter 541 is a serial in/out 4-bit right and left shift register, is connected at the shifting direction controlling end b to the power source circuit 539 at the output end (+6V) through a resistance 541a and is earthed through a switch 552. The above mentioned ring counter 541 is connected at the output ends c to f to a switching circuit 540 at the respective input ends and is connected at the power source end to the above mentioned power source circuit 539 at the output end (+6V).

The above mentioned switching circuit 540 is formed of Darlington-connected transistors, for example, of four circuits or the like and is connected at the output end to a transformer 546 at both ends on the primary side and to a transformer 547 at both ends on the primary side.

The above mentioned transformers 546 and 547 are connected at the intermediate points on the primary sides to the above mentioned power source circuit 539 at the output end (+12V) and are connected each at one end on the secondary side to the above mentioned USM 412 at the electrodes and are earthed at the other ends on the secondary sides.

The above mentioned switches 551a and 551b are connected at the control ends to the above mentioned OR circuit 549 at the output end. The above mentioned OR circuit 549 is connected at the first input end to the above mentioned switch 533 at the U and D ends as described above and is connected at the second input end to a later described straight return controlling circuit 550 at the control output end.

The above mentioned switch 552 is connected at the control end to the above mentioned OR circuit 548 at the output end. The above mentioned OR circuit 548 is connected at the first input end to the above mentioned switch 534 at the D end as described above and is connected at the second input end to a later described straight return controlling circuit 550 at the D bending controlling output end.

The above mentioned straight return controlling circuit 550 has an input end connected to a terminal 550a and an input end connected to a terminal 550b. The above mentioned terminal 550a is connected to the above mentioned switch 529 and the above mentioned terminal 550b is connected to the above mentioned bending angle detecting circuit 525. The above mentioned straight return controlling circuit 550 is connected at the D bending controlling output end to the above mentioned OR circuit 548 at the second input end as described above and is connected at the control output end to the above mentioned driving amplitude indicating circuit 545 at the straight return controlling end and to the OR circuit 549 at the second input end as described above.

The above mentioned power source circuit 539 is connected at the input end to a power source (+12V) through a fuse 553. Further, the above mentioned power source circuit 539 is connected at the input end to a constant voltage device 539a at the input end through the output end (+12V) and a resistance 539b and is earthed through an electrolytic capacitor 539c. The above mentioned constant voltage device 539a is earthed at the output end through an electrolytic capacitor 539d, is connected to the output end (+6) and is earthed at the earthing end.

The operation of the thus formed endoscope apparatus shall be explained.

A light source of the lamp 517 provided within the UCA 502 will be led through a light guide not illustrated and will be radiated to a part to be inspected or the like from the exit end surface of the above mentioned light guide arranged in the tip forming part 507 of the endoscope 501. The image of the object to be imaged radiated by this light source will be formed on the imaging surface of the solid state imaging device 533 by the objective lens 532.

The above mentioned solid state imaging device 533 will be fed with a driving signal from the video processor 524. The image of the object formed on the imaging surface will be photoelectrically converted by this driving signal so as to be an imaging signal which will be input into the video processor 524 provided within the UCA 502 by an imaging signal line not illustrated.

The above mentioned video processor 524 will convert the above mentioned imaging signal to a video signal, will at the same time synthesize the bending angle by the bending angle detecting circuit 525 and the contact pressure by the contact pressure detecting circuit 526 into a video signal which will be output to the monitor 527.

That is to say, the image of the imaged object, bending angle and contact pressure will be displayed in the monitor 527.

In the case of bending the bendable part 508 upward, the lever 528 of the bending switch 516 will be operated in a predetermined direction.

Thereby, the T end and U end of the switch 532 will be connected with each other, an electric current. for example, of 1 mA will flow to the variable resistance 535 from the constant current circuit 537, a voltage (mentioned as a speed setting voltage hereinafter) corresponding to the inclination of the lever 528 will be produced at the center of the above mentioned variable resistance 535 and this speed setting voltage will be applied to the comparing circuit 538 at the U speed setting input end.

The encoder 544 will make an F/V conversion of converting the number of revolutions of the USM 512 to a voltage proportional to the number of revolutions. The speed voltage which is a voltage of this converted number of revolutions will be applied to the above mentioned comparing circuit 538 at the speed detecting input end.

The above mentioned comparing circuit 538 will compare the above described speed setting voltage and speed voltage with each other and will output such control signal as will elevate the speed to the driving amplitude indicating circuit 545 in case the above mentioned speed voltage is lower than the above mentioned speed setting voltage but will output such control signal as will reduce the speed to the above mentioned driving amplitude indicating circuit 545 in case the above mentioned speed voltage is higher than the above mentioned speed setting voltage.

At the same time, the T end and U end of the switch 533 will be connected with each other, the output (+6V) of the power source circuit 539 will be applied to the OR circuit 549 at the first input end, the above mentioned OR circuit 549 will be of the logical signal "H" at the output end and the switches 551a and 551b will be ON.

The above mentioned driving amplitude indicating circuit 545 will outut a driving amplitude indicating signal to the feedback circuit 543 through the switch 551b by the control signal input at the indicating input end from the above mentioned comparing circuit 538.

The above mentioned feedback circuit 543 will output a frequency controlling signal to the pulse oscillating circuit 542 from the driving amplitude indicating signal of the above mentioned driving amplitude indicating circuit 545 and the feedback signal from the above mentioned USM 512.

The above mentioned pulse oscillating circuit 542 will oscillate a frequency four times as high as the starting frequency in case the USM 512 is stationary, will be controlled by the above mentioned frequency controlling signal when it is input and will oscillate a frequency four times as high as the driving frequency. The clock signal of the frequency four times as high as the starting frequency or driving frequency will be input into the ring counter 541 at the clock end a through the above mentioned switch 551a.

The D end and T end of the switch 534 will not be connected with each other and the OR circuit 548 will be of the logical signal "L" at the first input end. Further, the straight return controlling circuit 550 will be of the logical signal "L" at the bending controlling output end because the switch 529 will not be pushed. Thereby, the OR circuit 548 will be of the logical signal "L" at the second input end. That is to say, the OR circuit 548 will be of the logical signal "L" at the output end and the switch 552 will be OFF.

Therefore, in the above mentioned ring counter 541, as the switch 552 will be OFF, that is, will be of the logical signal "H" at the shifting direction controlling end b, the logical signals at the output ends c to f will be switched to be "H" sequentially, for example, in the order of the output ends f, e, d and c and these logical signals will be applied respectively to the switching circuit 540.

In the above mentioned switching circuit 540, the transformers 546 and 547 will be earthed at both ends on the primary sides, for example, sequentially by the logical signal of the above described ring counter 541.

Thereby, a sine wave voltage, for example, of 100 V rms will be produced in the above mentioned transformers 546 and 547 on the secndary sides and will be fed as a driving voltage to the above mentioned USM 512.

In this driving voltage, the phase angle of the voltage fed to the other electrode will be delayed or advanced by 90 degrees with respect to the phase angle of the voltage fed to one electrode by the ring counter 541.

The above mentioned USM 512 will be rotated by the above mentioned driving voltage and the driving force of the USM 512 will be transmitted to the reduction gear 511 which will pull the bending wire 510 and will bend the bendable part 508 upward.

In the case of bending the bendable part 508 downward, the lever 528 of the bending switch 516 will be operated in a predetermined direction.

Thereby, the T end and D end of the switch 532 will be connected with each other and an electric current, for example, of 1 mA will flow from the constant current circuit 537 to the variable resistance 536 and a speed setting voltage corresponding to the inclination of the lever 528 will be produced in the above mentioned variable resistance 536 at the intermediate point and will be applied to the comparing circuit 538 at the D speed setting input end.

At the same time, the T end and D end of the switch 533 will be connected with each other, the output (+6V) of the power source circuit 539 will be apppplied to the OR circuit 549 at the first input end, the OR circuit 549 will be of the logical signal "H" at the output end and the switches 551a and 551b will be ON.

Further, the T end and D end of the switch 534 will be connected with each other, the output (+6V) of the power source circuit 539 will be applied to the OR circuit 548 at the first input end, the OR circuit 548 will be of the logical signal "H" at the output end and the switch 552 will be ON.

Thereby, in the above mentioned ring counter 541, as the switch 552 will be ON, that is, will be of the logical signal "L" at the shifting direction controlling end b, the logical signals at the output ends e to f will be switched to be "H" sequentially, for example, in the order of c, d, e and f and these logical signals will be applied respectively to the switching circuit 540.

The above mentioned USM 512 will be rotated by the driving voltage as described above and the driving force of the USM 512 will be transmitted to the above mentioned reduction gear 511. The above mentioned gear 511 will pull the above mentioned bending wire 510 and will bend the above mentioned bendable part 508 downward.

The operations of the other formations are the same as in the case of bending the bendable part 508 upward and therefore shall not be described here.

Here, in case the above mentioned insertable part 504 is inserted, for example, into the large intestine and, as shown in FIG. 14(A), the tip side of the insertable part reaches the spleen bending part 562 which is a junction of the descending colon region 561 and horzontal colon region 563, the operator will push down the switch 529 while pushing in the insertable part 504.

The above mentioned straight return controlling circuit 550 will detect the pushing down of the switch 529 with the terminal 550a and will make the logical signal at the controlling output end "H". Futher, the above mentioned straight return controlling circuit 550 will obtain the bending direction of the above mentioned bendable part 508 from the bending angle detecting circuit 525 with the terminal 550b. If this bending direction is upward, the above mentioned straight return controlling circuit 550 will make the logical signals at the control output end and D bending controlling output end "H". Thereby, the logical signals of the OR circuits 548 and 549 at the second input ends and of the driving amplitude indicating circuit 545 at the straight return controlling end will be "H". Therefore, the logical signal of the above mentioned OR circuit 548 will be "H" at the output end, the switch 552 will be ON as described above, the logical signal of the above mentioned OR circuit 549 at the output end will be "H" and the switches 551a and 551b will be CN as described above. At the same time, the above mentioned driving amplitude indicating circuit 545 will output such driving amplitude indicating signal that the amplitude of the driving voltage will be maximum by the logical signal at the straight return controlling end to the feedback circuit 543 through the switch 551b. The above mentioned feedback circuit 543 will output a frequency controlling signal to the pulse oscillating circuit 542 as described above. The pulse oscillating circuit 542 will output a clock signal at the clock end a of the ring counter through the switch 551a as described above. As the switch 552 will be ON, the ring counter 541 will output to the switching circuit 540 a logical signal so as to bend the above mentioned bendable part 508 downward as described above.

Also, the above mentioned straight return controlling circuit 550 will make the logical signal at the controlling output end "H" if the bending direction of the above mentioned bendable part 508 obtained from the above mentioned bending angle detecting circuit 525 by the terminal 550b is downward.

The operations of the OR circuit 549 and driving amplitude indicating circuit 545 are the same as in the above described case that the bending direction of the bendable part 508 is upward, the switch 552 will be OFF and therefore a logical signal will be output so as to bend the above mentioned bendable part 508 upward as described above.

That is to say, when the switch 529 is pushed down, the above mentioned bendable part 508 will quickly bend downward or upward to be substantially straight with the bending angle zero as shown in FIG. 14(B). Therefore, the insertion will become easy. In case the bending state of the above mentioned bendable part 508 can not be caught, if the above mentioned switch 529 is pushed down, the above mentioned bendable part 508 will be able to be made substantially straight and there will be an effect that the operatability will improve.

In FIG. 15 is shown the seventh embodiment of the present inention.

FIG. 15 is an explanatory view of the tip part of an endoscoe as inserted in a spleen bending part. By the way, the endoscope apparatus is less the switch 529 of the above described sixth embodiment shown in FIGS. 12 and 13, the terminal 550a of the USM controlling circuits 522 and 523 is connected to a later described contact pressure sensor and the same formations shall bear the same reference numerals and shall not be explained here.

As shown in FIG. 15, the insertable part 504 of the endoscope 501 in this embodiment comprises a tip forming part 507, a bendable part 508 connected to the above mentioned tip forming part 507 at the rear end and a flexible tube part 509 connected to the above mentioned bendable part 508 at the rear end.

A contact pressure sensor 566 is pasted to the peripheral surface in the substantial center in the lengthwise direction of the above mentioned bendable part 508. A signal line not illustrated is connected to the above mentioned contact pressure sensor 566 and is connected to the straight return controlling circuit 550 at the terminal 550.

In such formation, in case the above mentioned insertable part 504 is inserted, for example, into the large intestine and, as shown in FIG. 15, the tip side of the above mentioned insertable part 504 reaches a spleen bending part 562 which is a junction of the descending colon region 561 and horizontal colon region 563, when the operator pushes in the insertable part 504, the above mentioned contact pressure sensor 566 will contact the body cavity wall. When the contact pressure of the above mentioned contact pressure sensor 566 becomes a predetermined pressure, the above mentioned straight return controlling circuit 550 will control the above mentioned bendable part 508 so as to be substantially straight the same as in the sixth embodiment.

That is to say, there is an effect that the above mentioned bendable part 508 will become straight and will be able to be easily passed through the spleen bending part 562.

The other formations, operations and effects are the same as in the sixth embodiment.

By the way, in the sixth and seventh embodiments, the bendable part 508 may be made to bend in a predetermined direction instead of being made to be substantially straight and may be made capable of setting the predetermined direction.

Figure 16:
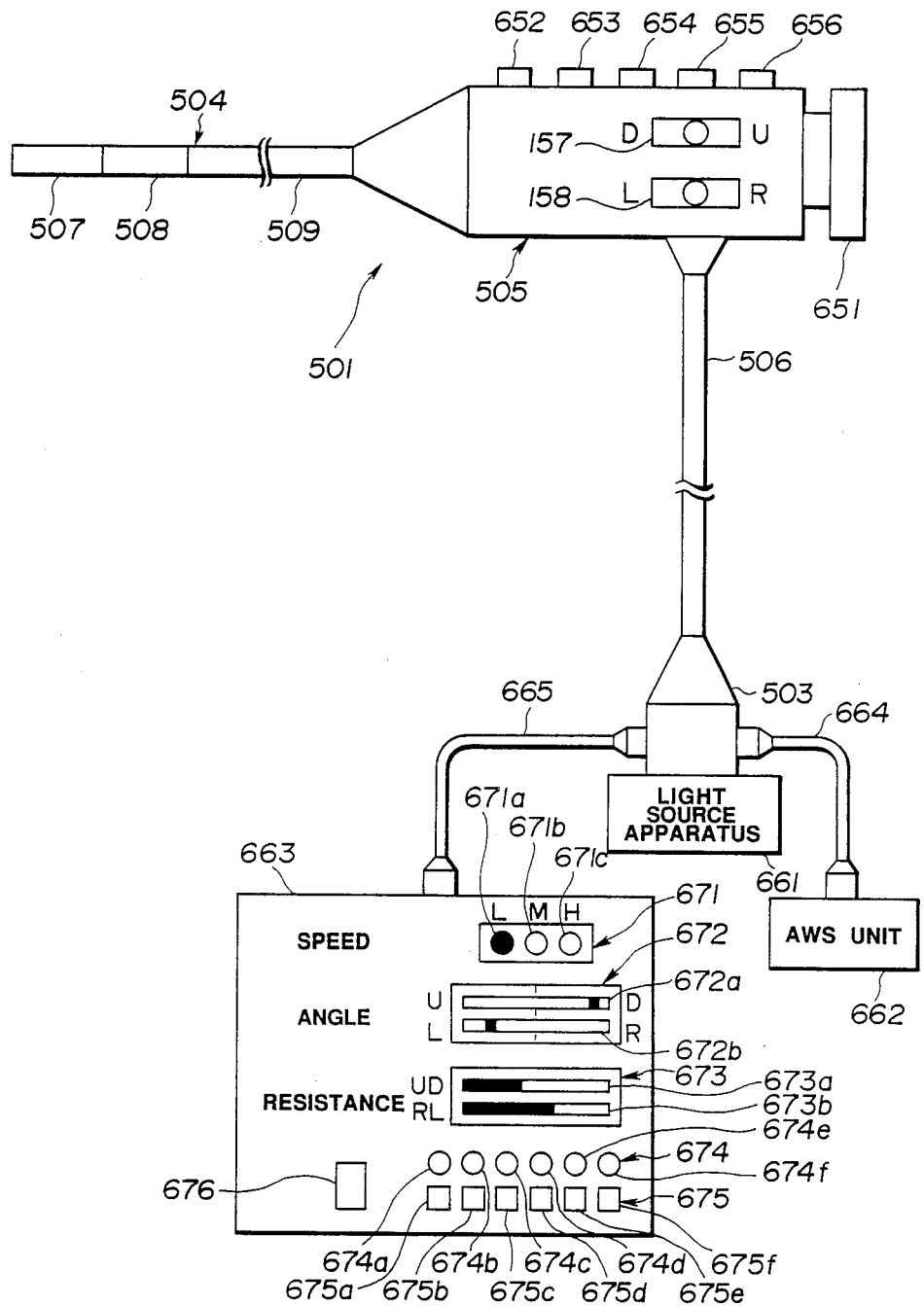
FIGS. 16 and 17 relate to the eighth embodiment of the present invention.
Figure 17:
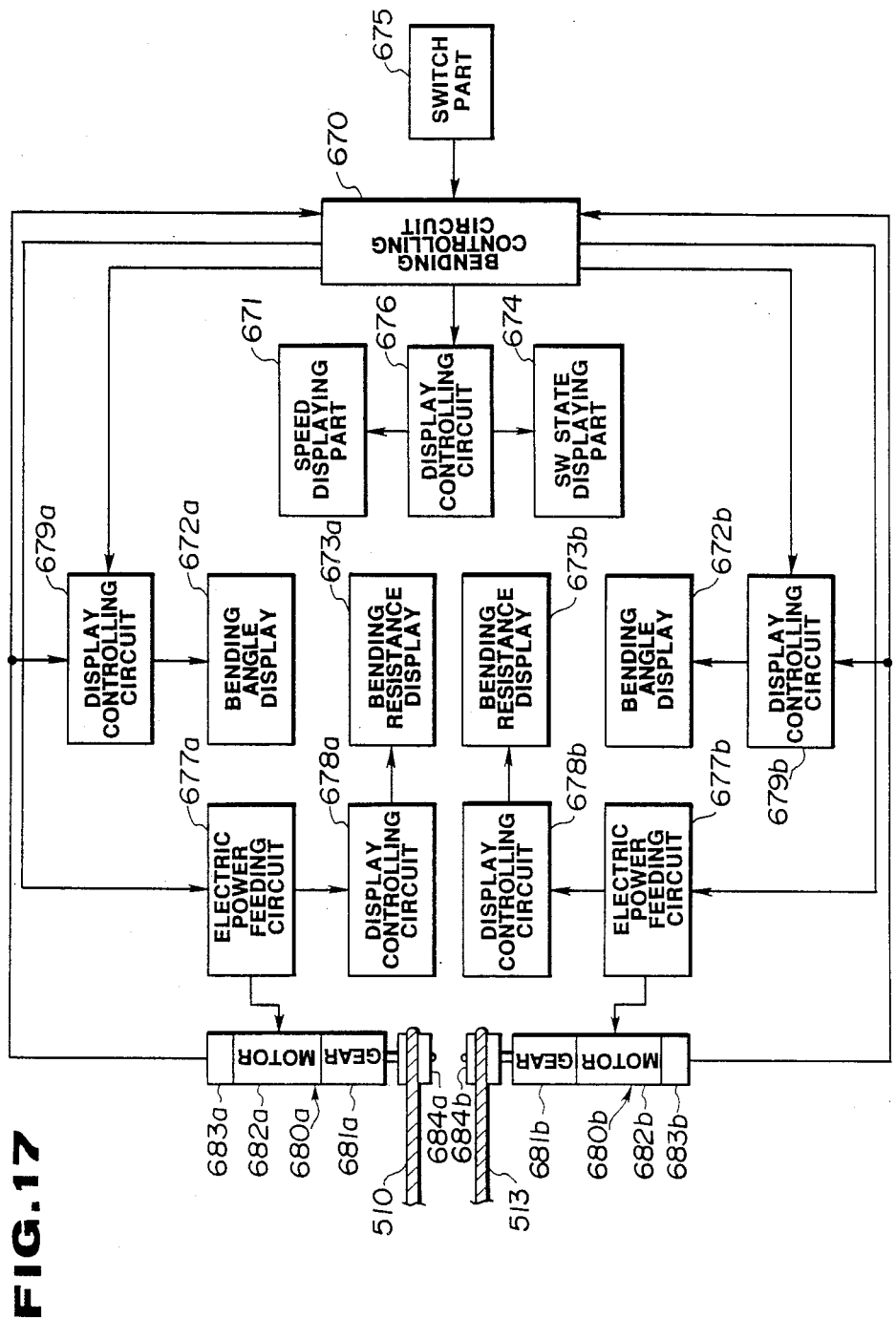

In FIGS. 16 and 17 is shown the eighth embodiment of the present invention.

By the way, the same components as in the sixth and seventh embodiments shall bear the same reference numerals and shall not be described here.

As shown in FIG. 16, the endoscope apparatus of this embodiment comprises an endoscope 501 which is a fiber scope, a light source apparatus 661 feeding a light source to the above mentioned endoscope 501, an AWS unit 662 controlling later described feeding and sucking air and water of the above mentioned endoscope 501 and a bending controlling apparatus 663 controlling a later described bending driving motor provided within the above mentioned endoscope 501.

The above mentioned endoscope 501 comprises an elongate insertable part 504, a thick operating part 505 connected to the above mentioned insertable part 504 at the rear end, an eyepiece part 651 connected to the above mentioned operating part 505 and for observing a part to be inspected or the like, for example, with a naked eye, a universal cord 506 extended sidewise out of the above mentioned operating part 505 and a connector 503 provided on the above mentioned universal cord 506 at the end.

The above mentioned insertable part 504 comprises a tip forming part 507, bendable part 508 and flexible tube par 509.

The above mentioned operating part 505 is provided with an air feeding switch 652 feeding air to a part to be inspected or the like by the above mentioned endoscope 501, a water feeding switch 653 feeding water to a part to be inspected or the like by the above mentioned endoscope 501, a sucking switch 654 sucking a fluid from the inspected part or the like by the above mentioned endoscope 501, a bending speed setting switch 655 setting the bending speed of the above mentioned bendable part 508, a functional switch 656 for performing on the hand base side, for example, one function of a switch setting various functions and provided in a later described bending controlling apparatus 663, a bending switch 657 is a neutral type momentary switch controlling the bending in the vertical direction of the above mentioned bendable part 508 and a bending switch 658 which is a neutral type momentary switch controlling the bending in the horizontal direction of the above mentioned bendable part 508.

The above mentioned connector 503 is removably connected to the above mentioned light source apparatus 503 and has relay cords 664 and 665 connected, for example, removably on the side.

The above mentioned relay cord 664 connects the above mentioned endoscope 501 and AWS unit 662 with each other. The above mentioned relay cord 665 connects the above mentioned endoscope 501 and bending controlling apparatus 663 with each other.

The above mentioned AWS unit 662 is provided with respective air feeding, water feeding and sucking pumps not illustrated and control valves not illustrated corresponding respectively to the above mentioned pumps.

The above mentioned AWS unit 662 is to be connected with the above mentioned air feeding switch 652, water feeding switch 653 and sucking switch 654 provided in the above mentioned operating part 505 of the above mentioned endoscope 501.

The above mentioned air feeding switch 652, water feeding switch 653 and sucking switch 654 control the pumps and control valves not illustrated of the above mentioned AWS unit 662 to operate the air feeding, water feeding and sucking functions.

The housing (sheath) of the above mentioned bending controlling apparatus 663 is provided with a speed displaying part 671 displaying the bending speed of the above mentioned bendable part 508, a bending angle displaying part 672 displaying the bending angle, a bending resistance displaying part 673 displaying the bending resistance of the above mentioned bendable part 508 from the driving power to a later described motor, a switch part 675 setting various functions driving the above mentioned bendable part 508, a power source switch 676 and a switch state displaying part (mentioned as an SW state displaying part hereinafter) 674 displaying the state of the above mentioned switch part 675.

The above mentioned speed displaying part 671 comprises a display 671a showing that the above mentioned bendable part 508 is in the state of bending at a low speed (L), a display 671b showing that the above mentioned bendable part 508 is in the state of bending at an ordinary speed (M) and a display 671c showing that the above mentioned bendable part 508 is in the state of bending at a high speed (H). The above mentioned displays 671a to 671c are, for example, of LED's.

Whenever the bending speed setting switch 655 of the above mentioned endoscope 501 is pushed down, the driving power (voltage/current) to a later described bending driving part will vary, the bending speed of the above mentioned bendable part 508 will be sequentially repeatedly switched, for example, to the low speed (L), ordinary speed (M) and high speed (H) and these states will be displayed in the displays 671a to 671c of the above mentioned displaying part 671.

The above mentioned bending angle displaying part 672 comprises a bending angle display 672a displaying the bending angle in the vertical direction of the above mentioned bendable part 508 and a bending angle display 672b displaying the bending angle in the horizontal direction. The above mentioned bending angle displays 672a and 672b are formed, for example, of multi-rows of LED's so that the bending angle may be displayed by ligting one of the above mentioned LED's.

The above mentioned bending resistance display 673 comprises a bending resistance display 673a displaying the bending resistance sustained by the above mentioned tip forming part 507 in the vertical direction and a bending resistance display 673b displaying the bending resistance sustained by the above mentioned tip forming part 507 in the horizontal direction. The above mentioned bending resistance displays 673a and 673b are formed, for example, of multi-rows of LED's so that the bending resistance may be displayed by lighting in the form of bars a plurallity of the above mentioned LED's.

The above mentioned switch part 675 comprises a free-engaging switch 675a freeing the above mentioned bendable part 508, a fine vibrating switch 675b fine vibrating the above mentioned bendable part 508, a mode switching switch 675c switching the mode of the fine vibration of the above mentioned bendable part 508, for example, to be in the UD direction and RL direction, a straight balancing switch 675 making the present state of the above mentioned bendable part 508 straight and making the above mentioned bending controlling apparatus 663 recognize it, a kind setting switch 675e setting the kind of the endoscope and a straight return switch 675f making the above mentioned bendable part 508 substantially straight.

In case the above mentioned bending switches 657 and 658 are not being operated, whenever the above mentioned free-engaging switch 675a is pushed down, a free state that a later described bending driving part can freely rotate and an engaged state that it is difficult to rotate will be switched to each other. In case a direct current motor is used, for example, for the above mentioned bending driving part, the driving power applying end of the above mentioned direct current motor will be opened when in the free state but will be shorted when in the engaged state.

Whenever the above mentioned fine vibrating switch 675b is pushed down, it will repeat to be ON-OFF and, in case it is ON, the above mentioned bendable part 508 will bend, for exammple, resectively by 10 degrees, for example, in the vertical/horizontal directions from the bending direction at that time, that is, will fine vibrate.

Whenever the above mentioned mode switching switch 675c is pushed down, the above described fine vibrating direction will be switched to be in the vertical direction and horizontal direction.

The above mentioned straight balance switch 675d makes the present bending angle of the above mentioned bendable part straight and makes the above mentioned bending controlling apparatus 663 recognize it. Usually, in case the endoscope is replaced or the like, the operator will confirm by sight the straight state and will operate the above mentioned straight balance switch 675d but, in case the above mentioned insertable part 504 is inserted into a complicatedly bent part, so that the inserting direction of the above mentioned insertable part 508 may not be missed, the bending state of the above mentioneed bendable part 508 then will be able to be memorized.

Whenever the above mentioned kind setting switch 675e is pushed down, the maximum value of the driving power adapted to the endoscope connected to the above mentioned bending controlling apparatus 663 will be set.

When the above mentioned straight return switch 675f is pushed down, the above mentioned bendable part 508 will be bent to be in the substantially straight state set by the above mentioned straight balance switch 675d or in a predetermined bending direction.

The above mentioned SW state displaying part 674 comprises a display 674a lighting in case the above mentioned free-engagine switch 675a is, for example, in the free state, a display 674b lighting in case the above mentioned fine vibrating switch 675b is, for example, ON, a display 674c lighting in case the above mentioned mode switching switch 675c selects, for example, a rotating motion, a display 674d lighting in case the above mentioned straight balance switch 675d is, for example, pushed down, a display 674e lighting in case the above mentioned kind setting switch 675e is, for example, pushed down and a display 674f lighting in case the above mentioned straight return switch 675f is, for example, pushed down. The above-mentioned displays 674a to 674f are, for example, of LED's.

As described above, the functional switch 656 provided on the operating part 505 of the above mentioned endoscope 501 is to function parallelly with one of the switches of the above mentioned switch part 675.

As shown in FIG. 17, the electric formation of the above mentioned endoscope apparatus comprises a bending wire 510 bending the above mentioned bendable part 508 in the vertical direction, a pulley 684a on which the above mentioned bending wire 510 is wound, a gear 681a formed of a plurality of the above mentioned pulleys 684a as pivoted, a motor 682a which is, for example, a direct current motor rotating the above mentioned pulley 684a through the above mentioned gear 681a, an encoder 683a detecting the rotating direction and speed of the above mentioned motor 682a, a bending wire 513 bending the above mentioned bendable part 508 in the horizontal direction, a pulley 684b on which the above mentioned bending wire 513 is wound, a gear 681 formed of a plurality of the above mentioned pulleys 684b as pivoted, a motor 682b which is, for example, a direct current motor rotating the above mentioned pulley 684b through the above mentioned gear 681b, an encoder 683b detecting the rotating direction and speed of the above mentioned motor 682b, the above mentioned switch part 675, a bending controlling circuit 670 controlling the bending by the signals from the above mentioned switch part 675 and encoders 683a and 683b, the above mentioned speed displaying part 671, the above mentioned SW state displaing part 674, a display controlling circuit 676 controlling the displaying of the above mentioned speed displaying part 671 and SW state displaying part 674 by the signal from the above mentioned bending controlling circuit 670, the above mentioned bending angle displays 672a and 672b, a display controlling circuit 679a controlling the above mentioned bending angle display 672a by the signals from the above mentioned bendinnng controlling circuit 670 and encoder 683a, a display controlling circuit 679b controlling the above mentioned bernding angle display 672b by the signals from the above mentioned bending controlling circuit 670 and encoder 683b, a power feeding circuit 677a feeding a driving power to the above mentioned motor 682a by the controlling signal of the above mentioned bending controlling circuit 670, a power feeding circuit 677b feeding a driving power to the above mentioned motor 682b by the controlling signal of the above mentioned bending controlling circuit 670, the above mentioned bending resistance display 673a, a display controlling circuit 678a detecting the bending resistance sustained in the vertical direction by the above mentioned bendable part 508 from the power fed to the above mentioned motor 682a by the above mentioned power feeding circuuit 677a and controlling the above mentioned bending resistance display 673a, the above mentioned bending resistance display 673a and a display controlling circuit 678b detecting the bending resistance sustained in the vertical direction by the above mentioned bendable part 508 from the power fed to the above mentioned motor 682b by the above mentioned power feeding circuuit 677b and controlling the above mentioned bending resistance display 673b. A vertical direction bending driving part 680a is formed of the above mentioned gear 681a, motor 682a and encoder 683a. A horizontal direction bending driving part 680b is formed of the above mentioned gear 681b, motor 682b and encoder 683b.

The above mentioned bending driving parts 680a and 680b are provided, for example, within the above mentioned operating part 505.

The above mentioned bending controlling circuit 670 is connected at the input end with the above mentioned switch part 675 and encoders 683a and 683b and is connected at the output end with the above mentioned display controlling circuit 676 at the input end, the above mentioned power feeding circuits 677a and 677b at the input ends and the above mentioned display controlling circuits 679a and 679b at the first input ends.

The above mentioned encoder 683a is connected to the above mentioned display controlling circuit 679a at the second input end. The above mentioned encoder 683b is connected to the above mentioned display controlling circuit 679b at the second input end.

The above mentioned display controlling circuit 679a is connected at the output end to the above mentioned bending angle display 672a. The above mentioned display controlling circuit 679b is connected at the output end to the above mentioned bending angle display 672.

The above mentioned power feeding circuit 677a is connected at the driving output end to the above mentioned motor 682a and is connected at the power output end to the above mentioned display controlling circuit 678a at the input end. The above mentioned power feeding circuit 677b is connected at the driving output end to the above mentioned motor 682b and is connected at the power output end to the above mentioned display controlling circuit 678b at the input end.

The above mentioned display controlling circuit 678a is connected at the output end to the above mentioned bending resistance display 673a. The above mentioned display controlling circuit 678b is connected at the output end to the above mentioned bending resistance display 673b.

The operation of the thus formed endoscope apparatus shall be explained.

When the bending controlling circuit 670 detects that the straight return switch 675f is pushed dwon from the switch part 675, it will compare the vertical and horizontal bending angles of the bendable part 508 detected by the encoders 683a and 683b with. for example, the substantially straight predetermined bending angle set by the straight balance switch 675 and will output a controlling signal to the above mentioned power feeding circuits 677a and 677b so that the above mentioned bendable part 508 may be of the above described predetermined bending angle.

Thereby, the motors 682a and 682b will rotate with the driving power fed from the above mentioned power feeding circuits 677a and 677b and this rotation will be transmitted to the pulleys 684a and 684b through the gears 681a and 681b.

Therefore, the above mentioned pulleys 684a and 684b will rotate, the bending wires 510 and 513 wound respectively on the above mentioned pulleys 684a and 684b will be pulled and the above mentioned bendable part 508 will bend so as to be of a predetermined angle which is, for example, substantially straight.

By the way, even in case the function of the above mentioned straight retuen switch 675f is allotted to the functional switch 656 provided on the operating part 504, when the above mentioned functional switch 656 is pushed down, it will operate the same.

That is to say, the tendable part 508 can be made to be of a predetermined bending angle set in advance by the straight balance switch 675d. In case the the above mentioned insertable part 504 is inserted, for example, into a complicatedly bent part, the present bending direction of the above mentioned bendable part 508 will be memorized by the above mentioned straight balance switch 675d and then, even when it is bent in the respective directions, by the straight return switch 675f, the inserting direction of the above mentioned insertable part 504 will not be missed, the subsequent insertion will be able to be made and there will be an effect that the inserting operatability will improve.

The other formations, operations and effects are the same as in the above described sixth and seventh embodiments.

Figure 18:
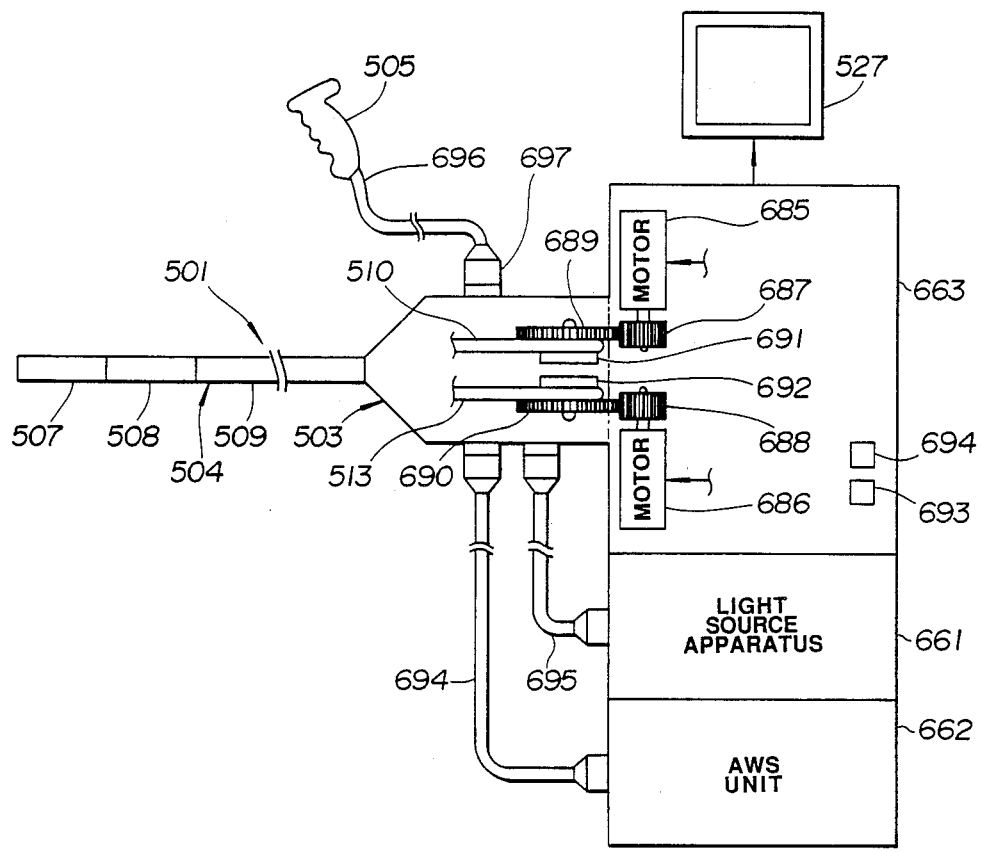
FIG. 18 relates to the ninth embodiment of the present invention.

In FIG. 18 is shown the ninth embodiment of the present invention.

By the way, the same components as in the sixth to eighth embodiments shall bear the same reference numerals and shall not be described here.

As shown in FIG. 18, the endoscope apparatus of this embodiment comprises an endoscope 501 formed of an insertable part 504 and a thick connector 503 connected to the above mentione insertable part 504 at the rear end, a bending controlling apparatus 663 having a built-in video processor to which the connector 503 of the above mentioned endoscope 501 is removably connected, a light source apparatus 661, an AWS unit 662 and a monitor 527.

The above mentioned bending controlling apparatus 663 is provided internally with a video processor not illustrated, a bending controlling circuit not illustrated, a motor 685 bending and driving a bendable part 508 in the vertical direction, a gear 687 pivoted to the driving shaft of the above mentioned motor 685, a motor 686 bending and driving the above mentioned bendable part 508 in the horizontal direction and a gear 688 pivoted to the driving shaft of the above mentioned motor 685.

The housing (sheath) of the above mentioned bending controlling apparatus 663 is provided with a bending direction memorizing switch 693 memorizing the bending direction of the above mentioned bendable part 508, a bending direction return switch 694 returning the above mentioned bendable part 508 in the bending direction memorized by the above mentioned bending direction memorizing switch 693, a switch part not illustrated and an SW state displaying part not illustrated.

The above mentioned connector 503 is provided internally with a gear 689 engaged with the above mentioned gear 687, a pulley 691 arranged on the above mentioned gear 689, a gear 690 engaged with the above mentioned gear 688 and a pulley 592 arranged on the above mentioned gear 690. A bending wire 510 is wound on the above mentioned pulley 691. A bending wire 513 is wound on the above mentioned pulley 692.

To the above mentioned connector 503 are removably connected a light guide cable 695 connected to the above mentioned light source apparatus 661 at one end, a relay cable 664 connected to the above mentioned AWS unit at one end and a later described connector 697.

The above mentioned light guide cable 695 is removably connected at the other end to the above mentioned light source apparatus 661. The above mentioned relay cable 664 is removably connected at the other end to the above mentioned AWS unit 662.

A calble 696 is extended from the operating part 505 and is provided at the end with the above mentioned connector 697.

The above mentioned operating part 505 is provided with an air feeding switch, water feeding switch, sucking switch, bending speed setting switch, functional switch and bending switch not illustrated.

The operation of the thus formed endoscope apparatus shall be explained.

When the above mentioned bending direction memorizing switch 693 is pushed down, the present bending direction of the bendable part 508 will be memorized in a bending controlling circuit not illustrated.

Here, in case the above mentioned bendable part 508 is bent vertically/horizontally in order to confirm the inserting direction, for example, of the insertable part 504 and is then to be returned in the bending direction as before the above mentioned bendable part was bent horizontally/vertically as described above, a bending direction returning switch 694 will be pushed down.

The above mentioned bending controlling circuit not illustrated will control and drive the motors 685 and 686 to rotate to return the above mentioned bendable part 508 as described above.

Thereby, the gears 687 and 688 pivoted to the driving shafts of the above mentioned motors 685 and 686 will be operatively connected with the rotations of the above mentioned motors 685 and 686 and the gears 689 and 690 engaged respectively with the above mentioned gears 687 and 688 will rotate.

By the rotation of the above mentioned gears 689 and 690, the pulleys 691 and 692 arranged respectively on the above mentioned gears 689 and 690 will be operatively connected to pull the bending wires 510 and 513.

Therefore, the above mentioned bendable part 508 will return in the bending direction memorized in the above mentioned bending direction memorizing switch 693.

That is to say, the straight balance switch and straight return switch can be used as limited to the function of making the bendable part 508 substantially straight, a predetermined bending angle can be set by the bending direction memorizing switch 693 and bending direction return switch 694 and there is an effect that the operatability is improved by memorizing the bending direction respecrtively independently.

The other formations, operations and effects are the same as in the sixth to eighth embodiments.

Figure 19:
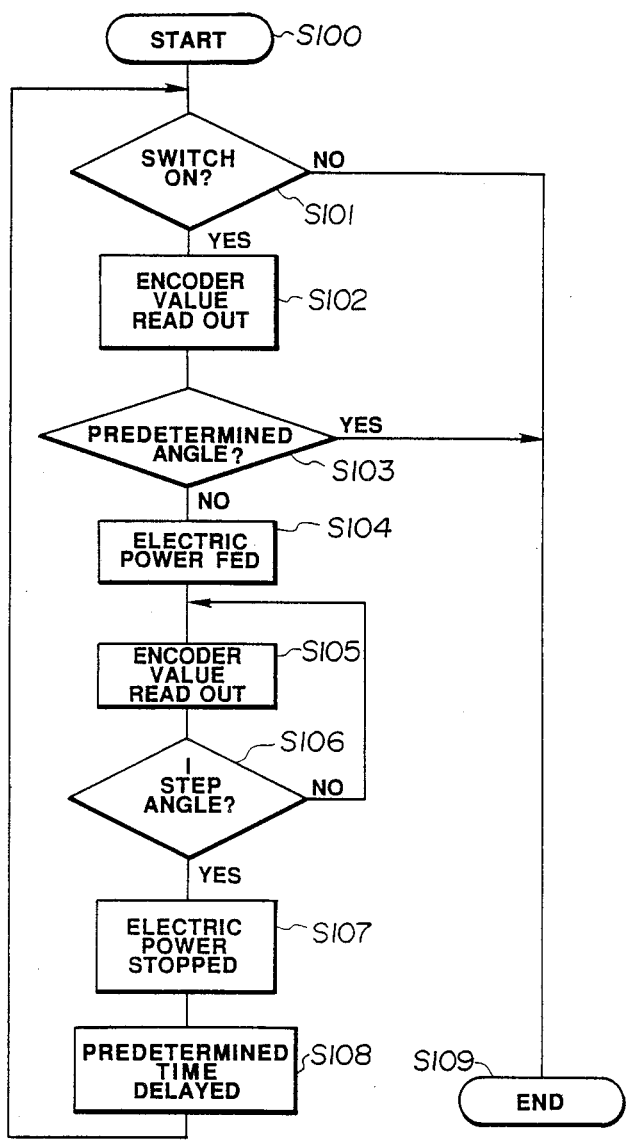
FIG. 19 relates to the tenth embodiment of the present invention.

In FIG. 19 is shown the tenth embodiment of the present invention.

FIG. 19 is an explanatory view of a bending controlling method.

By the way, the endoscope apparatus is the same as in the sixth to ninth embodiments and only the controlling method shall be explained.

As shown in FIG. 19, in this embodiment, in the case of bending the bendable part in a predetermined bending direction, it will not be bent in the predetermined bending direction in a moment but will be gradually bent.

In this embodiment, beginning at the step (mentioned as S hereinafer)100, it is judged at S101 whether the straight return switch or bending direction return switch (generally mentioned as a return switch hereinafter) is pushed down or not.

In case it is judged by the above mentioned S101 that the return switch is not pushed down (NO), the process of this embodiment will end at S109 but, in case it is judged that the return switch is pushed (YES), the value of the bending angle by the encoder will be read out at S102.

Then, it is judged at S103 whether the value of the bending angle read out is a predetermined bending angle or not.

In case it is judged at S103 that it is the predetermined bending angle (YES), the process of this embodiment will end at the above mentioned S109 but, in case it is judged that it is not the predetermined bending angle (NO). a driving power will be fed to the bending motor at S104.

Then, at S105, the value of the bending angle by the encoder is read out.

Then, at S106, it is judged whether the value of the read out bending angle has reached the bending angle of the gradually bending 1 step or not.

In case it is judged by the above mentioned S106 that it is not the bending angle of 1 step (NO), the process from S105 will be repeated and the bending of the bendable part will be continued.

In case it is judged that it is the bending angle of 1 step (YES), the feed of the driving power fed at the above mentioned S104 will be stopped, the process will be interrupted for a predetermined time by S108 and the process from the above mentioned S101 will be repeated to gradually reach the predetermined bending angle.

The above described bending angle of 1 step is set to be below the width of the predetermined bending angle.

By the way, in case the power feed is made momentarily at the above mentioned S104 and it is judged that the judgment by S106 is not of the bending angle of 1 step (NO), the process from S104 will be repeated and further S107 may be omitted so as to approach the bending angle of 1 step.

That is to say, in the case of making the bendable part, for example, a substantially straight predetermined bending angle, by gradually bending it, the predetermined bending angle will be able to be made while confirming the state of the inspected object. There is an effect that, in case the safety is required, it will be able to be secured.

The other formations, operations and effects are the same as in the sixth to ninth embodiments.

Figure 20:
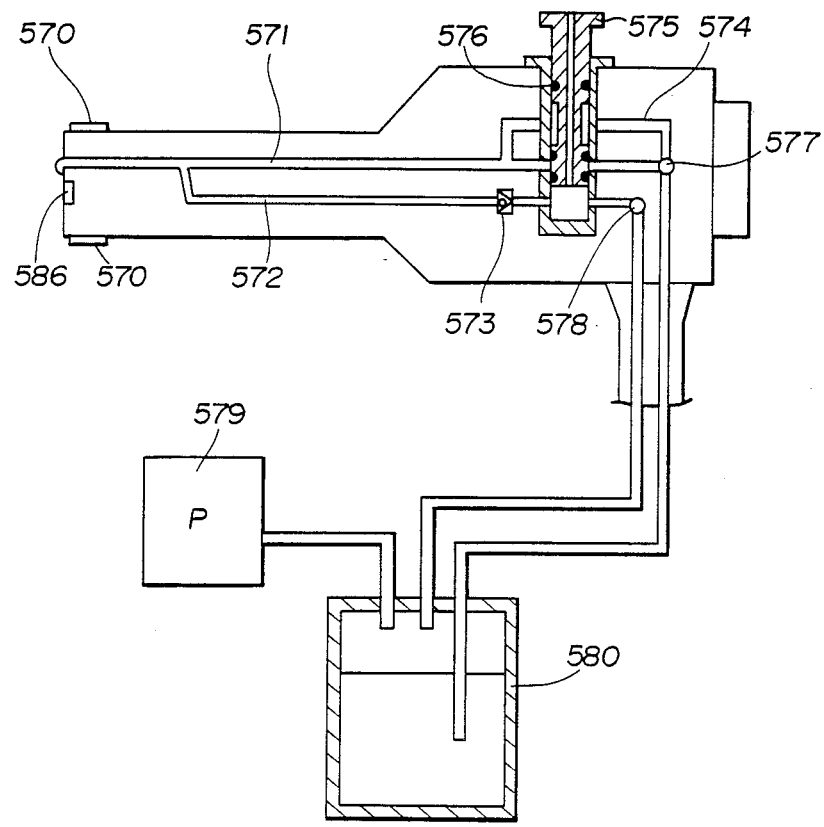
FIGS. 20 to 30 relate to means for notifying the operator of the state of an endoscope apparatus.
Figure 21:
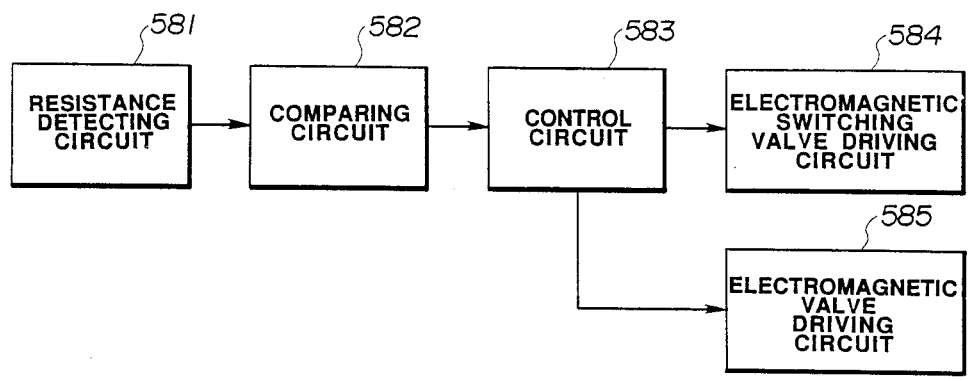

Now, in case the bendable part of the endoscope is bent and the tip forming part strongly contacts such part to be inspected as the body cavity wall, the operator had better be made to recognize that state. Therefore, as shown in FIGS. 20 and 21, a contact pressure sensor 570 is arranged in the above mentioned tip forming part so that the contact pressure detected by the above mentioed contact pressure sensor 570 may be detected as a bending resistance by a resistance detecting circuit 581. In case the detected signal from the resistance detecting circuit 581 is compared with the predetermined value in a comparing circuit 582 and this compared result is judged to exceed the predetermined value, a control signal will be output to a control circuit 583. Thereby, the above mentioned control circuit 583 will output a control signal to an electromagnetic switching valve driving circuit 584 and electromagnetic valve driving circuit 585, the electromagnetic switching valve driving circuit 584 will drive an electromagnetic switching valve 577 to be switched to the side of a water feeding bypass 574 and the electromagnetic valve driving circuit 585 will close an electromagnetic valve 578. Such fluid as, for example, water introduced into a water feeding tank 580 by air fed from an air feeding source 579 will be pressurized and will be jetted to an observing window 586 from a water feeding pipe line 571 through the above mentioned electromagnetic switching valve 577 and water feeding bypass 574.

Thereby, while observing the inspected object, the operator can recognize that the above described bending resistance is large. By the way, the reference numeral 572 represents an air feeding pipe line for feeding air, 573 represents a check valve for preventing the back flow of the feed water from the air feeding pipe line 572, 575 represents an air and water feeding valve for ordinarily feeding air/water by the operator and 576 represents an O-ring for air-tightening the above mentioned air and water feeding valve 575.

By the way, the water feeding bipass 574 may be arranged up to the tip forming part so as to jet water on the lengthwise front surface of the tip forming part.

Figure 22:
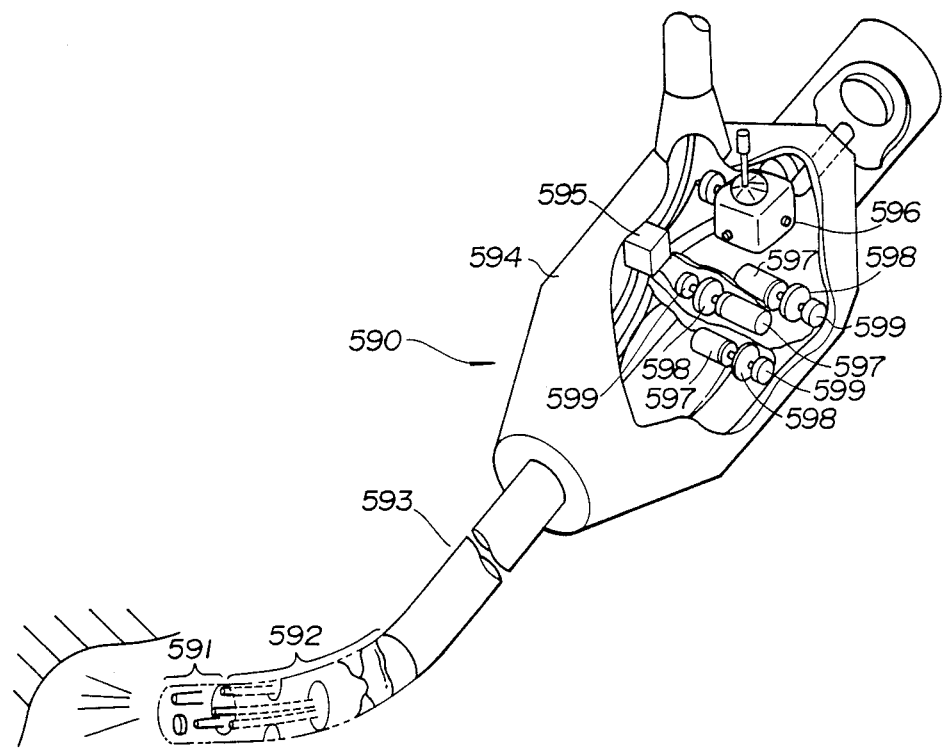
Figure 23:
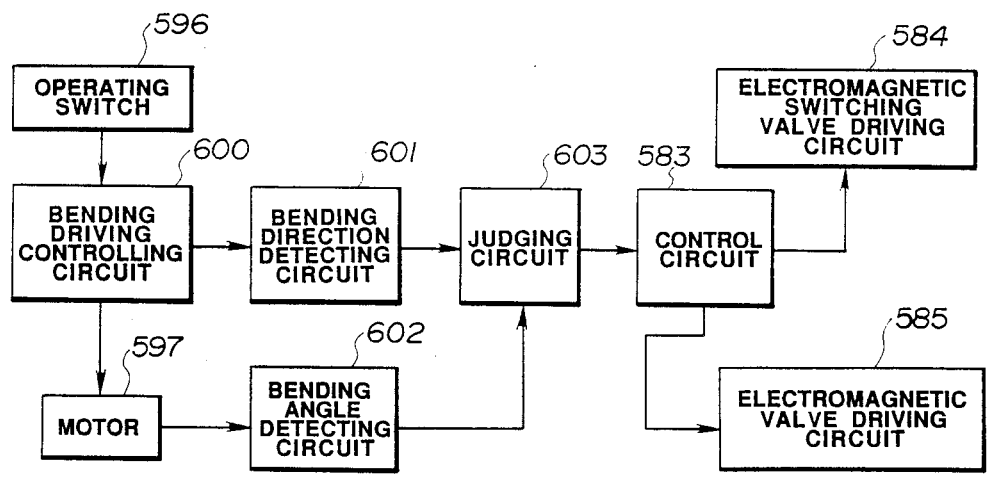

Also, as shown in FIGS. 22 and 23, the above described recognizing means may be used in the endoscope using a motor so that the operator may recognize that the motor mis-operates. More particularly, when an operating switch 596 provided in an operating part 594 is operated, a driving controlling circuit 600 provided in a driving controlling part 595 will control the driving of the motor 597 and will output to the bending direction detecting circuit 601 a signal showing the bending direction. The above mentioned motor 597 is provided with a pulley 598 for bending a bendable part 592 and the above mentioned pulley 598 is provided with a potentiometer 599. A potentiosignal from the above mentioned potentiometer 599 will be input as a bending angle signal into a bending angle detecting circuit 602. The above mentioned bending direction detecting circuit 601 and bending angle detecting circuit 602 will output the input signals as comparable signals to a judging circuit 603. In the above mentioned judging circuit 603, the above described signals of the above mentioned bending direction detecting circuit 601 and bending angle detecting circuit 602 will be judged and, in case the bending direction is different from the operator's recognition, that is, in case the motor 597 mis-operates, a control signal may be output to the above described control circuit 583 and such fluid as, for example, water may be jetted to the above described observing window.

Figure 24:
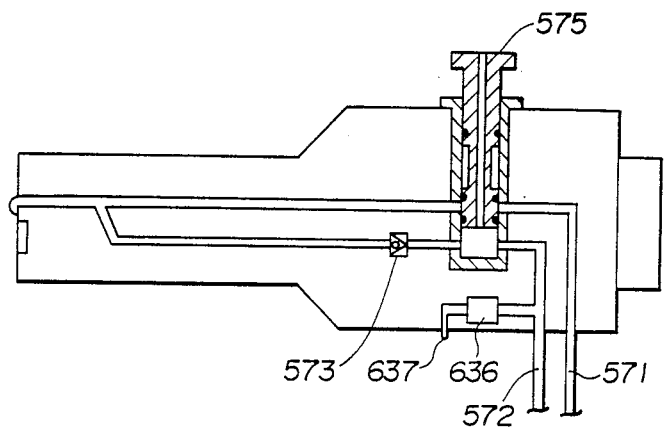
Figure 26:
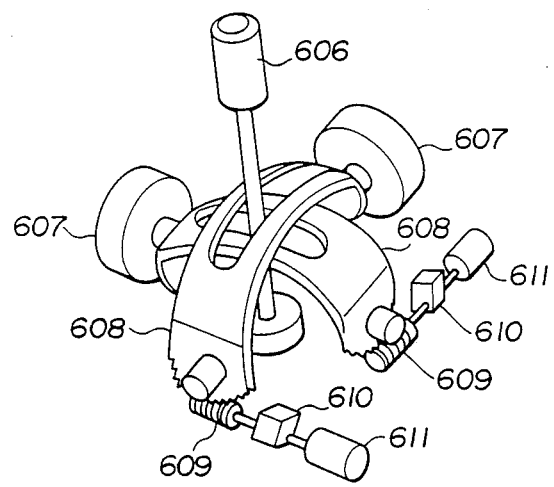
Figure 25:
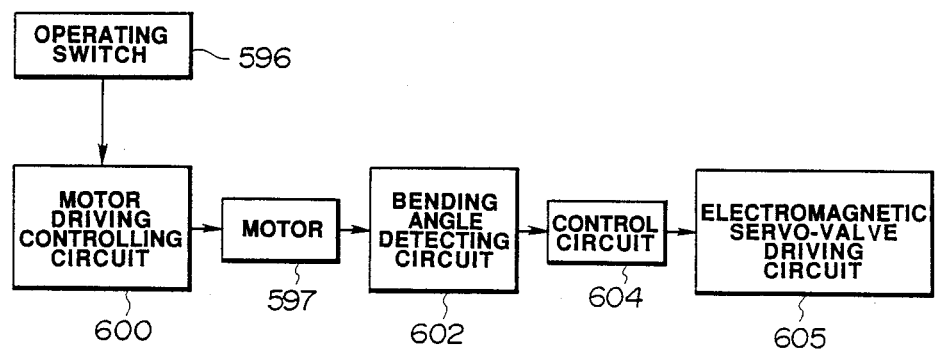

In the endoscope using the motor, the operator can not easily find the bending angle of the bendable part. Therefore, as shown in FIGS. 24 and 25, the motor driving controlling circuit 600 is controlled with an operating switch 596, the motor 597 is driven by the above mentioned motor driving controlling circuit 600, the bending angle by the above described potentiometer is detected by the bending angle detecting circuit 602 and a control circuit 604 controls an electromagnetic servo valve driving circuit 605 with a signal from the above mentioned bending angle detecting circuit 602. The above mentioned electromagnetic servo valve driving circuit 605 controls the opening of an electromagnetic servo valve 636 so as to vary in response to the bending angle so that air fed from an air feeding source not illustrated by the opening of the above mentioned electromagnetic servo valve 636 may be jetted out of a jetting port 637 provided in the operating part through an air feeding pipe line 572 and the operator may recognize the bending angle. By the way, the reference numeral 573 represents a check valve preventing the back flow of water fed from the air feeding pipe line 572 and 575 represents an air and water feeding valve for the operator to ordinarily feed air/water.

Figure 27:
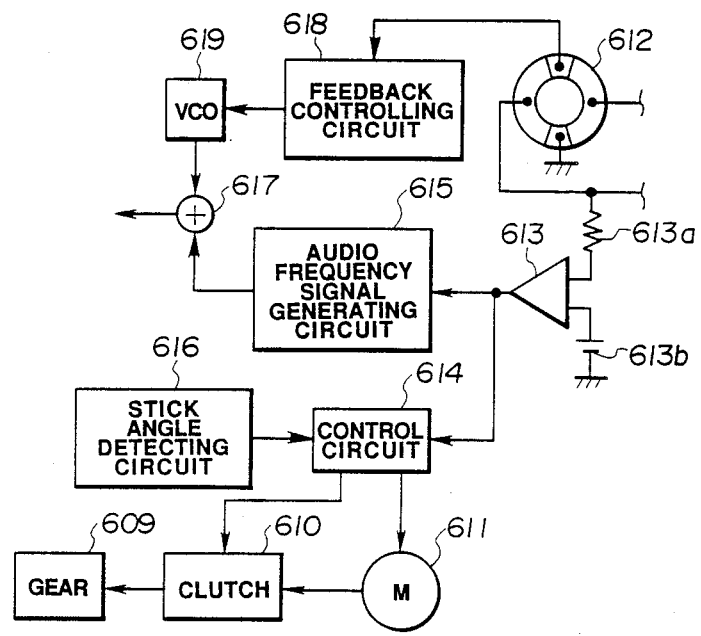

In an endoscope using a USM as a motor, when the bending resistance is large, an over-current will flow through the USM. As shown in FIGS. 15 and 27, this over-current is detected by a resistance 613a connected to a detector 613 at one input end and is compared with the current of a comparable voltage source 613b connected to the above mentioned detector 613 at the other input end and, in case a predetermined current value is exceeded, the above mentioned detector 613 will output a detecting signal to an audio frequency signal generating circuit 615 and control circuit 614. By this detecting signal, the audio fequency signal generating circuit 615 will output to an adder 617 at one end an audible signal, for example, of 1.5 KH$_2$ which is a signal of a frequency in an audible range. The above mentioned adder 617 is connected at the other end to a VCO (voltage controlled oscillator) 617 driving controlling the rotation of a USM 612 at the output end. The above mentioned adder 617 will superimpose the audible signal from the audio frequency signal generating circuit 615 on the driving power from the VCO 619 and will feed it to the piezoelectric body of the USM 612. Thereby, an alarming sound will be issued from the piezoelectric body of the above mentioned USM 612. The above mentioned control circuit 614 will drive a motor 611 and will control a clutch 610 to be connected with the motor 611. Therefore, the driving force of the motor 611 will rotate a gear 609 throgh the clutch 610. A joy stick return member 608 will be operatively connected with the rotation of the above mentioned gear 609 and a joy stick 606 which is an opeating switch will be returned to a neutral position. The position of the joy stick 606 will be detected by a joy stick angle detecting circuit 616 from the output signal of a potentiometer 607 arranged on the above mentioned joy stick return member 608 and will be output to the above mentioned control circuit 614. By the way, the above mentioned VCO 619 will be controlled by a feedback controlling circuit 618 detecting a feedback signal from the USM 612 at one end.

Figure 28:
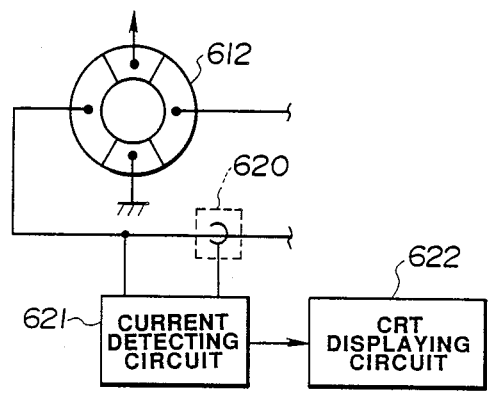

Also, as described above, in the endoscope using the USM as a motor, when the bending resistance is large, an over-current will flow through the USM. As shown in FIG. 28, this over-current will be detected by a current detecting circuit 621 from a current probe 620 provided on a driving signal line on one side connected to the electrode of the USM 612 and the above mentioned driving signal line and this detected result will be displayed in a monitor not illustrated by a CRT displaying circuit 622.

Figure 29:
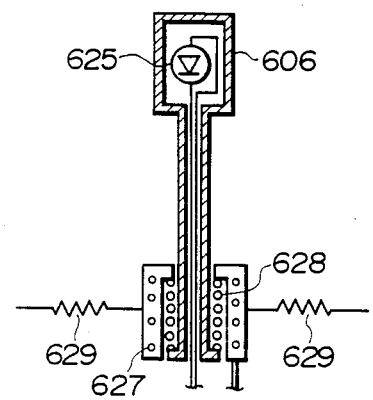
Figure 30:
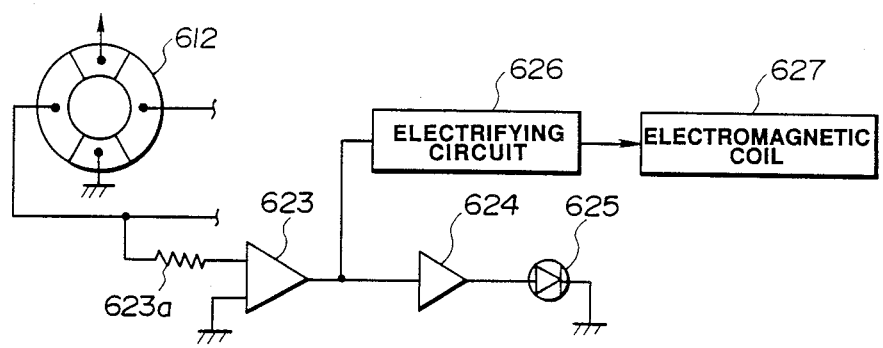

Also, as described above, in the endoscope using the USM as a motor, when the bending resistance is large, an over-current will flow through the USM. As shown in FIGS. 29 and 30, a detecting circuit 623 is connected at one input end through a resistance 623a to the driving signal line on one side connected to the electrode of the USM 612 and is earthed at the other input end. The above mentioned detecting circuit 623 will detect the over-current of the USM 612 and will outut it to an LED driver 624 and electrifying circuit 626. Thereby, an LED driver 624 will light an LED 625 provided within the joy stick 606 and the electrifying circuit 626 will drive an electromagnetic coil 627. By the above mentioned electromagnetic coil 627, the above mentioned joy stic 606 will be lifted upward and, as described above, the LED 624 will be lighted. Therefore, the operator can recognize that the bending resistance has increased. By the way, in an ordinary case, the above mentioned joy stick 606 will be pushed downward by a coil spring 628 and the above mentioned electromagnetic coil 627 will be held in a fixed position by springs 629.

In FIGS. 31 to 35 is shown the 11th emboddiment of the present invention.

Figure 32:
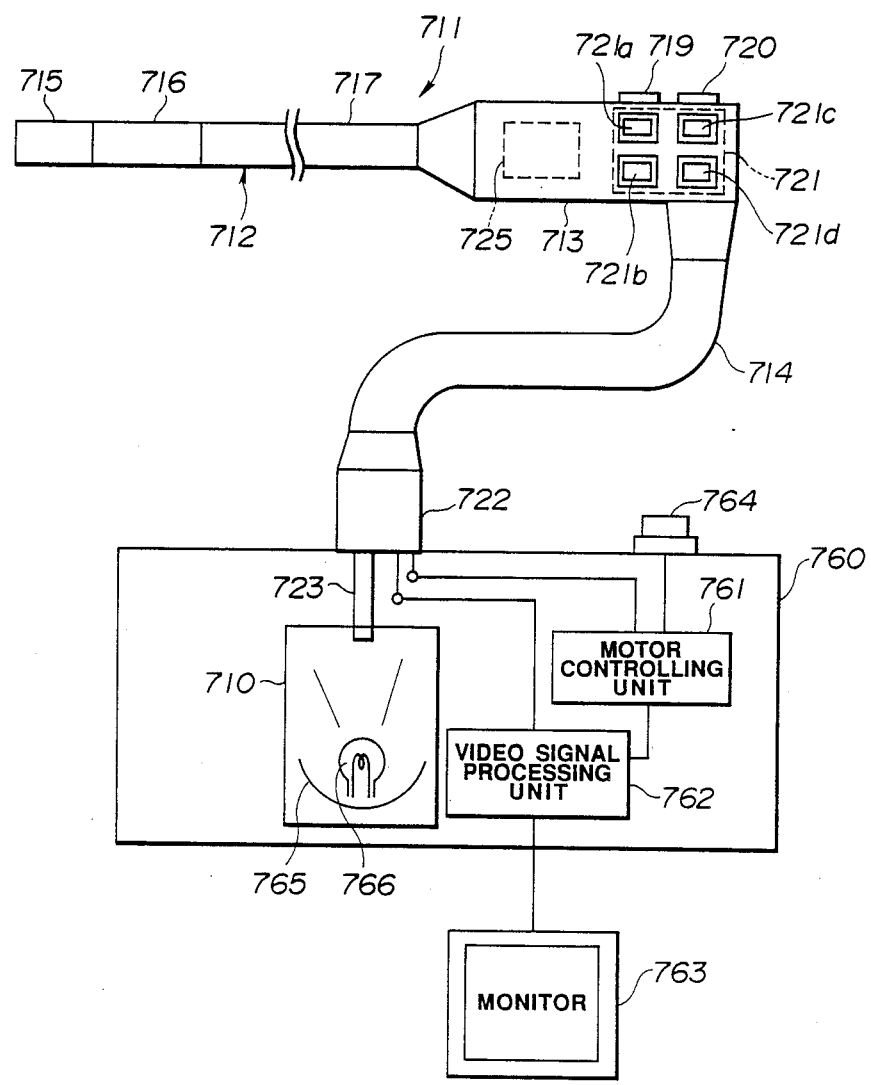

As shown in FIG. 32, the electronic endoscope apparatus comprises an endoscope 711 formed to be elongate so as to be insertable, for example, into a body cavity, a video processor apparatus 760 provided internally with a light source unit to which a universal cord 714 of the above mentioned endoscope 711 is to be connected by a connector 722 and a monitor 763 displaying such inspected object as a part within a body cavity by an output signal of the video processor apparatus 760.

The above mentioned endoscope 711 comprises an elogate insertable part 712, a thick operating part 713 connected to this insertable part at the rear end, a universal cord 714 extended sidewise out of this operating part 713 and a connector 22 provided on this universal cord 714 at the end. The above mentioned insertable part 712 comprises a tip forming part 715 in which an imaging device or the like imaging an object to be imaged is arranged, a vertically/horizontally bendable part 716 connected to this tip forming part 715 at the rear end and a flexible tube part 717 connected to this bendable part 716 at the rear end. The above mentioned operating part 713 is internally provided with a case 725 in which a later described bending operating apparatus for bending and driving the above mentioned bendable part is arranged and is provided with an air and water feeding switch 719, sucking switch 720 and switch part 721. The switch part 721 is provided with an upward bending switch 721a, downward bending switch 721b, leftward bending switch 721c and rightward bending switch 721d for indicating the bending directions of the bendable part 716.

The above mentioned video processor apparatus 760 is provided with the above described light source unit 710 formed of a reflector 765 and illuminating bulb 766 for feeding an illuminating light to a light guide 723 projecting out of the above mentioned connector 722, a video signal processing unit 762 for converting and variously processing the imaging signal from the imaging device arranged in the above mentioned tip forming part and outputting it as a video signal to the above mentioned monitor 763, a later described motor controlling unit 762 for controlling the above mentioned bending operating apparatus part 729 arranged in the above mentioned operating part 713 and a free switch 764 for freeing the above mentioned bendable part 716 arranged in the sheath of the above mentioned video processor apparatus.

Figure 33:
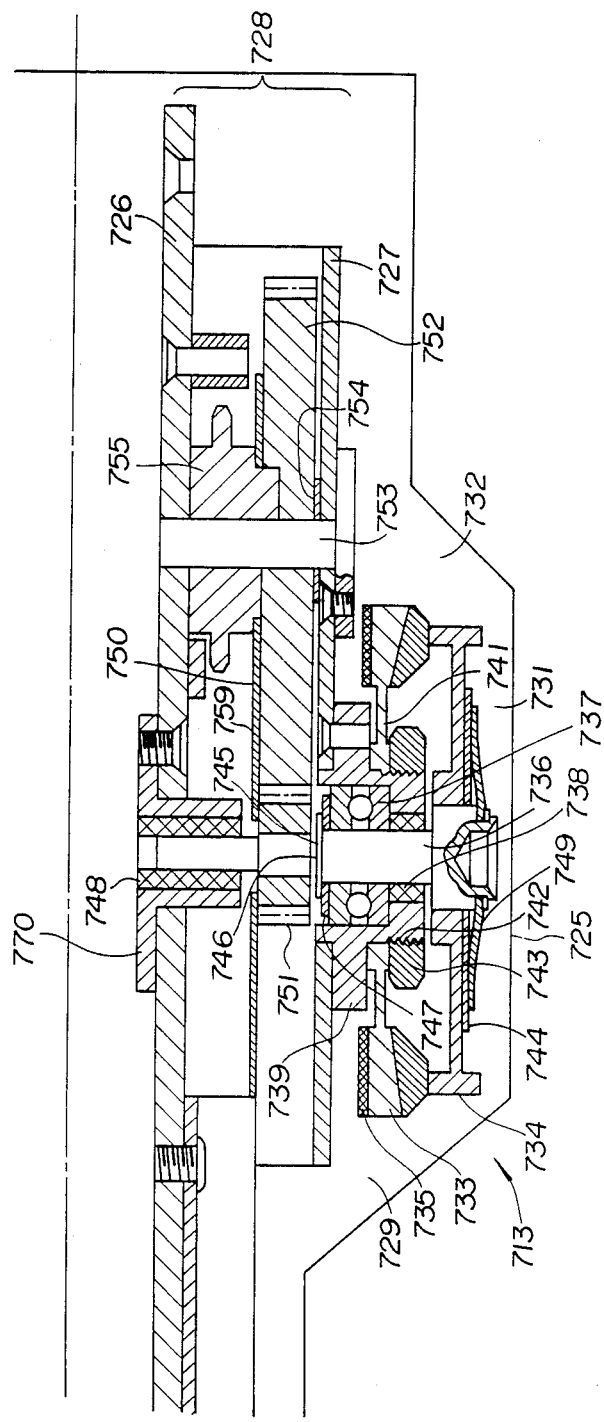

As shown in FIG. 33, frames (only one frame is illustrated as a frame 728) of two sets each consisting of a main frame 726 and sub-frame 727 forming the space at a fixed spacing are arranged symmetrically on the right and left within the above mentioned case 725 provided within the above mentioned operating part 713. A bending operating apparatus part 729 for the vertical bending operation is assembled with this on frame 729 and a bending operating apparatus part (not illustrated) for the horizontal bending operation is assembled with the other frame.

As these bending operating apparatus parts for the vertical/horizontal bending operations are of the same formation, one bending operating apparatus part 729 for the vertical bending operation shall be explained. An oscillating wave motor unit 731 driven, for example, by ultrasonic waves is incorporated in the sub-frame 727 supported by the above mentioned main frame 726. The oscillating wave motor 732 in this oscillating wave motor unit 731 consists of a substantially disc-like stator 733 and a rotor 734 in close contact with the surface opposed to the case 725 side on the periphery of this stator 733 and a piezoelectric body 735 is bonded and fixed to the surface on the periphery of the stator 733 positioned on the side opposite the rotor 734. The rotor 734 is fitted and fixed to a rotary shaft 736 at the tip. The rotary shaft 736 is borne in the intermediate parts by a thrust bearing 737 and first radial ball bearing 738 which are housed and supported within the same first bearing box 739. This first bearing box 739 is jointed and secured to the above mentioned sub-frame 727 by screws 741. The above mentioned stator 733 is fitted to the first bearing box 739 on the outer periphery and is fastened and fixed with a nut 743 screwed to a scew 742 formed on the outer periphery of the above mentioned first bearing box 739. That is to say, the stator 733 is fixed and can not rotate.

The above mentioned thrust bearing 737 is fixed in a predetermined position on the peripheral surface of the rotary shaft 736 by a snap ring 745 supported by a washer 747 fitted in a groove 746 formed on the peripheral surface of the rotary shaft 736. This rotary shaft 736 is supported on the inner end side by a second radial bearing 748 held in a second bearing box 770 fitted to the main frame 726.

On the other hand, a dish spring 749 is fitted by calking to the thus supported rotary shaft 736 at the outer end. The above mentioned rotor 734 is strongly energized by this dish spring so as to be pushed against the stator 733. A rubber sheet 744 for protecting the rotor 734 from being hurt and for preventing the rotor 734 and rotary shaft 736 from slipping is provided between the rotor 734 and dish spring 739.

A driving gear 751 for such transmitting gear mechanism as, for example, a transmitting gear train 750 as positioned intermediately between the first radial bearing 738 and second radial bearing 748 is secured by such means as shrink fitting to the rotary shaft 736 of this oscillating wave motor unit 731. This driving gear 751 meshes with a driven gear 752 rotatably supported on a shaft 753 provided between the main frame 726 and sub-frame 727. A washer 754 made, for example, of a resin is inserted between this driven gear 752 and sub-frame 727 so that the rotation of the driven gear may be smooth. A sprocket 755 as a pulling operation rotor is supported between the driven gear 752 and main frame 726 so as to be freely rotatable with respect to the shaft 753 and is connected with the driven gear 752 by engagement or, for example, by screws not illustrated so as to integrally rotate.

Figure 34:
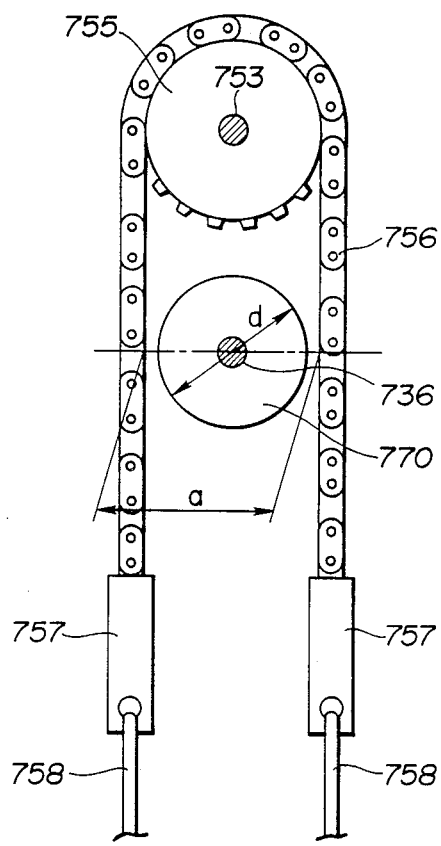

Further, as shown in FIG. 34, a chain 756 is wound on this sprocket 755 and bending operation wires 758 are connected to this chain 756 at the respective ends through connecting pieces 757. This chain 756 and bending operation wires 758 form pulling members. The respective bending operation wires 758 are connected to the bendable part 716 at the tip or to the tip forming part 715 at the rear end through the insertable part 712. As described later, when the sprocket 755 rotates, the bending operation wires 758 will be pushed or pulled in response to the rotating direction to bend the bendable part 716 of the insertable part 712. By the way, as shown in FIG. 33, between the transmitting gear train 750 and chain 756 side, a partition plate 759 is set to prevent them from contacting with each other.

On the other hand, as shown in FIG. 34, the rotary shaft 736 and sprocket 755 are arranged as displaced in the lengthwise direction from each other. The width a between the chains 756 corresponding to the outside diameter of the sprocket 755 is larger than the outside diameter d of the second bearing box 770 positioned within this width a. Therefore, the second bearing box 770 is arranged with a space between the chains 756 so that the second bearing box 770 may not contact the chain 756.

Figure 31:
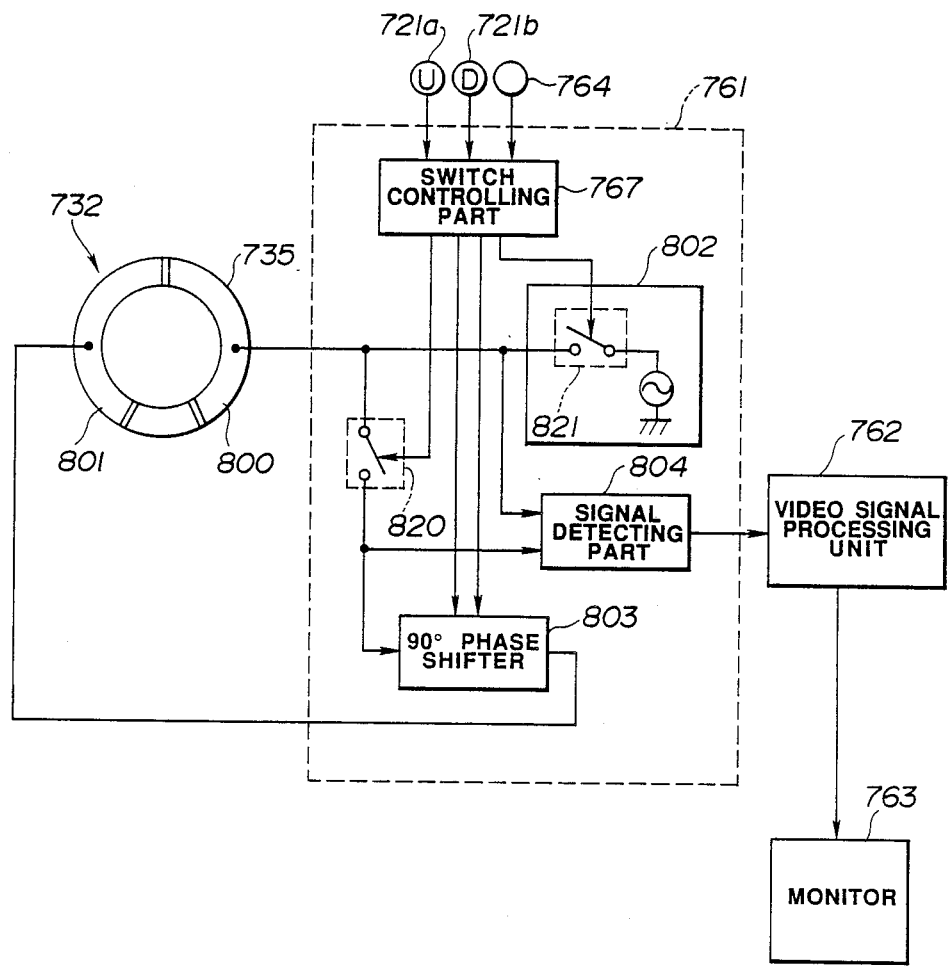
FIGS. 31 to 35 relate to the 11th embodiment of the present invention.

The formation of a circuit of detecting and reporting the bending and driving state in the vertical direction of the endoscope insertable part is shown in FIG. 31. By the way, the formation of a circuit of detecting and reporting the bending and driving state in the horizontal direction is the same and therefore shall not be described here.

As shown in FIG. 31, the above mentioned motor controlling unit 761 comprises a switch controlling part to which the above mentioned upward bending switch 721a, downward bending switch 721b and free switch 764 are connected at the input end, a power source 802 for feeding a driving power to an oscillating wave motor 732, a signal detecting part 804 for detecting the above mentioned driving power and a 90 degree phase shifter 803 for controlling the phase of the driving power on one side fed to the oscillating wave motor. The above mentioned power source 802 is provided with a switch 821 for switching the driving power ON/OFF. The power source through this switch 821 is connected to an electrode 800 provided in a piezoelectric body 735 of the oscillating wave motor 732 and to the signal detecting part 804 at the first input end. Further, the power source through the above mentioned switch 821 is connected to the signal detecting part 804 at the second input end through a switching switch 820 controlling the rotating state and free state of the above mentioned oscillating wave motor 732 and to the 90 degree phase shifter 803 at the input end. The above mentioned signal detecting part 804 is connected at the outut end to the above described video signal processing unit 762 at the input end. The above mentioned video signal processing unit 762 is connected at the output end to a monitor 763 at the input end. The above mentioned 90 degree phase shifter 803 is connected at the output end to an electrode 801 provided in the piezoelectric body 735 of the oscillating wave motor 732. The above mentioned switch controlling part 767 is connected at the power source controlling output end to the above mentioned switch 821 at the control end. The above mentioned switch controlling part 767 is connected at the driving controlling output end to the switching switch 820 at the control end. The above mentioned switch controlling part 767 is connected at the upward controlling output end to the above mentioned 90 degree phase shifter 803 at the upward controlling end. The above mentioned switch controlling part 767 is connected at the downward controlling output end to the above mentioned 90 degree phase shifter 803 at the downsard controlling end.

Figure 35:
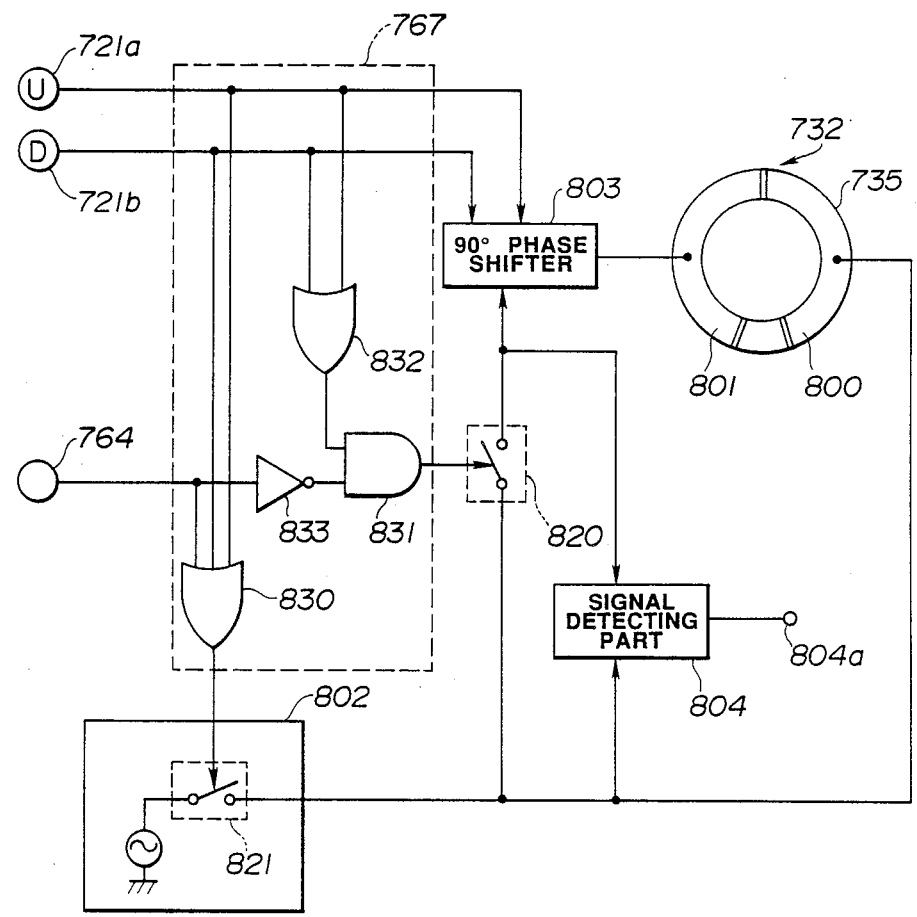

The formation of a bending driving circuit for vertically bending the endoscope bendable part 716 is shown in FIG. 35. By the way, the horizontally bending driving circuuit is of the same formation and therefore shall not be described here.

A switch 721a outputting a logical signal for upward bending the above mentioned bendable part 716 is connected at the output end to an OR circuit 830 at the first input end, an OR circuit 832 at the first input end and the 90 degree phase shifter 803 at the upward controlling end. A switch 721b outputting a logical signal for downward bending the above mentioned bendable part 716 is connected at the output end to the OR circuit 830 at the second input end, the OR circuit 832 at the second input end and the 90 degree phase shifter 803 at the downward controlling end. A switch 764 outputting a logical signal for freeing the above mentioned bendable part 716 is connected at the output end to an inverter 833, to the OR circuit 830 at the third input end and to a circuit not illustrated for controlling a horizontal oscillating wave motor. The above mentioned OR circuuit 830 is connected at the output end to the above described switch 821 at the control end. The above mentioned OR circuit 832 is connected at the output end to an AND circuit 831 at the first input end. The above mentioned inverter 833 is connected at the output end to the AND circuit at the second input end. The above mentioned AND circuit 831 is connected at the output end to a switch 820 at the control end. The other connections are the same as in the above described FIG. 31 and shall not be described here.

The operation of the thus formed electronic endoscope apparatus shall be explained. By the way, the case of vertically bending controlling the bendable part 716 shall be described but the operation of the circuit and the like in the case of horizontally bending controlling the bendable part is the same as in this explanation and shall not be described here.

As shown in FIG. 32, the light of the illuminating bulb 766 will be reflected by the reflector 765 so as to be a light source, will be radiated to the light guide 723 on the entrance end surface, will be led through the above mentioned light guide 723 and will be radiated to an object to be imaged not illustrated from the exit end surface of the above mentioned light guide 723 arranged in the tip forming part 715 of the endoscope 711. The image of the above mentioned object illuminated by this light source will be formed on the photoelectrically converting surface of an imaging device arranged in the above mentioed tip forming part 715 so as to be a photoelectrically converted signal which will be input into the video signal processing unit 762 by the signal line and will become a video signal to be displayed in the monitor 763.

In case the free switch 764 is not pushed, the output of the free switch 764 shown in FIG. 35 will be a logical signal "L". Thereby, the output of the inverter 833 will be a logical signal "H" and will be applied to the AND circuit 831 at the second input end. Therefore, the logical signal output by the AND circuit 831 will depend on the output signal of the OR circuit 832 connected at the first input end and the switch 820 will be controlled by the above mentioned output signal. That is to say, when the upward bending switch 721a or downward bending switch 721b is pushed, the switching switch 820 will be ON.

Therefore, when the upward bending switch 721a is pushed and the output of the above mentioned upward bending switch 721a becomes a logical signal "H", the output of the OR circuit 830 will become a logical signal "H" and the output of the OR circuit 832 will become also a logical signal "H". By the above mentioned OR circuit 830, the switch 821 will be ON and a driving voltage V o Sin ( $\omega$ t ) will be applied to the electrode 800 from the power source 802. At the same time, as described above, the output of the AND circuit 831 will become a logical signal "H" and the switching switch 820 will be ON. Therefore, the above mentioned driving voltage V o Sin ( $\omega$ t ) will be applied to the 90 degree phase shifter 803 and signal detecting part 804. Thereby, with the logical signal "H" which is the output of the above mentione upward bending switch 721a input at the upward bending controlling end, the 90 degree phase shifter 803 will advance the phase of the above mentioned driving voltage V o Sin ( $\omega$ t ) by 90 degrees so as to be of a driving voltage V o Sin ( $\omega$ t $+\pi/2$ which will be applied to the electrode 801. That is to say, the driving voltage V o Sin ( $\omega$ t ) will be applied to the electrode 800 of the piezoelectric body 735 pasted to the stator 733 of the oscillating wave motor 732, the driving voltage V o Sin ( $\omega$ t $+\pi/2$ ) will be applied to the electrode 801 of the above mentioned piezoelectric body 735 and a proceeding wave will be produced in the above mentioned stator 733. Thereby, the rotor 734 will rotate in a predetermined direction, the rotary shaft 736 fixed to the above mentioned rotor 734 and the driving gear 751 fixed to the above mentioned rotary shaft 736 will be operatively connected with each other and the sprocket 755 connected to the above mentioned driven gear 752 will rotate. Thereby, the chain 756 wound on the sprocket 755 will move in response, one of the bending wires 758 connected to the chain 756 at the ends through the connecting pieces 757 will be payed out to be pushed and the other wire will be pulled in. Therefore, the bendable part 716 of the insertable part 712 will bend to direct the tip part 715 upward.

Also, when the downward bending switch 721b is pushed and the output of the above mentioned downward bending switch 721b becomes a logical signal "H", the output of the OR circuit 830 will become a logical signal "H" and the output of the OR circuit 832 will also become a logical signal "H". Thereby, the same as in the case of bending the bendable part 716 upward, the driving voltage V o Sin ( $\omega$ t ) will be applied to the electrode 800 from the power source 802.

At the same time, the above mentioned driving voltage V o Sin ( $\omega$ t ) will be applied to the 90 degree phase shifter 803 and signal detecting part 804. Thereby, with the logical signal "H" which is the output of the above mentioned downward bending switch 721b input at the downward bending controlling end, the 90 degree phase shifter 803 will delay the phase of the above mentioned driving voltage V o Sin ( $\omega$ t ) by 90 degrees so as to be a driving voltage V o Sin ( $\omega$ t $-\pi/2$ ) which will be applied to the electrode 801. That is to say, the driving voltage V o Sin ($\omega$ t) will be applied to the electrode 800 of the piezoelectric body 735 pasted to the stator 733 of the oscillating wave motor 732, the driving voltage V o Sin ( $\omega$ t $-\pi/2$ ) will be applied to the electrode 801 of the above mentioned piezoelectric body 735 and a proceeding wave will be produced in the above mentioned stator 733. Thereby, the rotor 734 will rotate in the direction reverse to the case of bending the bendable part 716 upward. As described above, the chain 756 wound on the driven sprocket 755 will move in response, one of the bending wires 758 connected to the chain 756 at the ends through the connecting pieces 757 will be payed out to be pushed and the other will be pulled in. Therefore, the bendable part 716 of the insertable part 712 will bend so as to direct the tip part 715 downward.

With the driving voltage V o Sin ($\omega$ t) applied at the first input end and second input end, the signal detecting part 804 will detect that a proceeding wave has been produced in the oscillating wave motor 732 and will output a detecting signal to the video signal processing unit 762 shown in FIG. 31 through the output end 804. In the above mentioned video signal processing unit 762, such image signal as characters displaying that a proceeding wave has been produced in the oscillating wave motor 732, that is, that the bendable part is bending operating will be synthesized, for example, with a video signal, will be output and will be displayed in the monitor 763.

Here, when the free switch 64 is pushed and the output of the above mentioned free switch 764 becomes a logical signal "H", the output of the inverter 833 will become a logical signal "L" and will be applied to the AND circuit 831 at the second input end. Thereby, the output signal of the AND circuit 831 will become a logical signal "L" even if the output of the OR circuit 832 connected at the first input end is a logical signal "H". That is to say, even if the upward bending switch 721a and downward bending switch 721b are pushed, the switching switch 820 will not be ON. Therefore, no driving voltage will be applied to the 90 degree phase shifter 803 and signal detecting part 804. However, as the output of the free switch 764 connected at the third input end is a logical signal "H", the output of the OR circuit 830 will be a logical signal "H", the switch 821 will be ON and the driving voltage V o Sin ($\omega$ t) will be applied to the electrode 800 from the power source. That is to say, the driving voltage V o Sin ($\omega$ t) will be applied to the electrode 800 of the piezoelectric body 735 pasted to the stator 733 of the oscillating wave motor 732, no driving voltage will be applied to the electrode 801 of the above mentioned piezoelectric body 735 and a standing wave will be produced in the above mentioned stator 733. Thereby, the rotor 734 will become free and the bendable part 716 of the insertable part 712 will be freely bent by the external force applied to the tip part 715.

Also, with the driving voltage V o Sin (ω t) applied at the first input end and the non-signal state at the second input end, the signal detecting part 804 will detect that a standing wave has been produced in the oscillating wave motor 732 and will output a detecting signal to the video signal processing unit 762 shown in FIG. 31 through the output end 804a. In the above mentioned video signal processing unit 762, such image signal as characters displaying that a standing wave has been produced in the oscillating wave motor 732, that is, that the bendable part is free will be synthesized, for example, with a video signal, will be output and will be displayed in the monitor 763.

Further, in case the upward bending switch 721a, downward bending switch 721b and free switch 764 are not pushed, that is, when the switch 821 and switching switch 820 are OFF, no driving voltage will be applied to the electrodes 800 and 801 of the piezoelectric body 735 pasted to the stator 733 of the oscillating wave motor 732. Thereby, the rotor 734 will be locked so as not to easily rotate and the bendable part 716 of the insertable part 712 will not be easily bent even by an external force applied to the tip part 715.

By the above described operation, the signal detecting part 804 will always monitor the driving voltage fed to the oscillating wave motor 732 and will display in the monitor 763 that a proceeding wave or standing wave is produced in the stator 733 of the above mentioned oscillating wave motor 732, that is, a rotating state or free state so as to be recognized by the operator.

Figure 36:
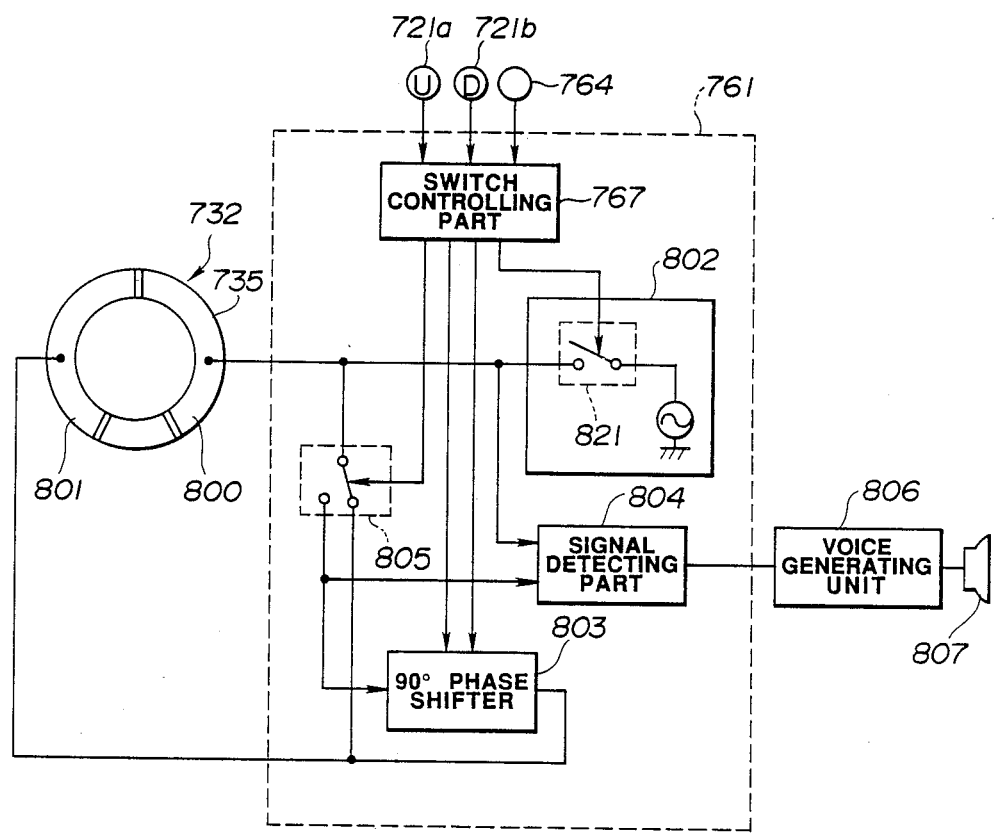
FIG. 36 relates to the 12th embodiment of the present invention.

In FIG. 36 is shown the 12th embodiment of the present invention.

FIG. 36 is a block diagram showing the formation of a circuit for detecting and reporting the state of driving an endoscope bendable part in the vertical direction. The formation of a circuit for detecting and reporting the bending driving state in the horizontal direction is also the same and shall not be described here. The formation of the endoscope apparatus is the same as in FIG. 32 of the 11th embodiment. The same components as in the 11th embodiment shall bear the same reference numerals and shall not be explained here.

As shown in FIG. 36, the above mentioned motor controlling unit 761 comprises a switch controlling part 767 connected at the input end with the above mentioned upward bending switch 721a, downward bending switch 721b and free switch 764, a power source 802 for feeding a driving power to the oscillating wave motor 732, a signal detecting part 804 for detecting the above mentioned driving power and a 90 degree phase shifter 803 for controlling the phase of the driving power on one side fed to the oscillating wave motor. The above mentioned power source 802 is provided with a switch 821 for switching the driving power ON/OFF. The power source through this switch 821 is connected to an electrode 800 provided in the piezoelectric body 735 of the oscillating wave motor 732 and to the signal detecting part 804 at the first input end. Further, the power source through the above mentioned switch 821 is connected to the signal detecting part 804 at the second input end and to the 90 degree phase shifter 803 at the input end through the ON contact of a switching switch 805 controlling the rotating state and free state of the oscillating wave motor. The above mentioned signal detecting part 804 is connected at the output end to a voice generating unit 806 at the input end. The voice generating unit 806 is connected at the output end to a speaker 807. The above mentioned 90 degree phase shifter 803 at the output end and the above mentioned switch 805 at the OFF contact are connected to an electrode 801 provided in the piezoelectric body 735 of the oscillating wave motor 732. The above mentioned switch 821 is connected at the control end with the above mentioned switch controlling part 767 at the power source controlling output end. The switching switch 805 is connected at the control end with the above mentioned switch controlling part 767 at the driving controlling output end. The above mentioned 90 degree phase shifter 803 is connected at the upward controlling end with the above mentioned switch controlling part 767 at the upward controlling output end. The above mentioned 90 degree phase shifter 803 is connected at the downward controlling end with the above mentioned switch controlling part 767 at the upward controlling output end.

The operation of the circuit for detecting and reporting the driving state of the endoscope bendable part in the vertical direction shall be explained.

The same as in the 11th embodiment, when the upward bending switch 721 is pushed, the switch controlling part 767 will control the switches 821 and 805 to be ON. Further, the switch controlling circuit 767 will control the above mentioned 90 degree phase shifter 803 to advance the phase by 90 degrees the same as in the 11th embodimet in the driving voltage applied to the 90 degree phase shifter 803 and to apply it to the electrode 801.

Also, the same as in the 11th embodiment, when the downward bending switch 721b is pushed, the switch controlling part 767 will control the switches 821 and 805 to be ON. Further, the switch controlling circuit 767 will control the above mentioned 90 degree phase shifter 803 to delay the phase by 90 degrees the same as in the 11th embodiment in the driving voltage applied to the 90 degree phase shifter and apply it to the electrode 801.

Here, when the free switch 764 is pushed, the same as in the 11th embodiment, the switch controlling part 767 will control the switch 821 to be ON and the switching switch 805 to be OFF. Thereby, the driving voltage V o Sin ( ω t) through the switch 821 of the power source 802 will be applied to the electrode 800 and also to the electrode 801 through the OFF contact of the switch 805. Thereby, a standing wave will be produced in the stator 733 and the oscillating wave motor 732 will become free the same as in the 11th embodiment. When the same driving voltage is given to the electrodes 800 and 801, the standing wave produced in the stator 733 will become larger than in the 11th embodiment and the bendable part 716 will freely move in response to the smaller external force applied to the tip part 715 of the insertable part 712.

The signal detecting part 804 will detect that the driving voltage is fed to the piezoelectric body 735 so that a standing wave may be produced in the stator 733 the same as in the 11th embodiment and will output the above mentioned detecting signal to the voice generating unit 806. Thereby, the voice generating unit 806 will report with a voice through the speaker 807 that a standng wave is produced in the oscillating wave motor 732, that is, that the bendable part 716 is free.

In this embodiment, even if the operator does not always monitor the monitor, by being notified with a voice, he will be able to recognize that the bendable part 716 is free.

Figure 37:
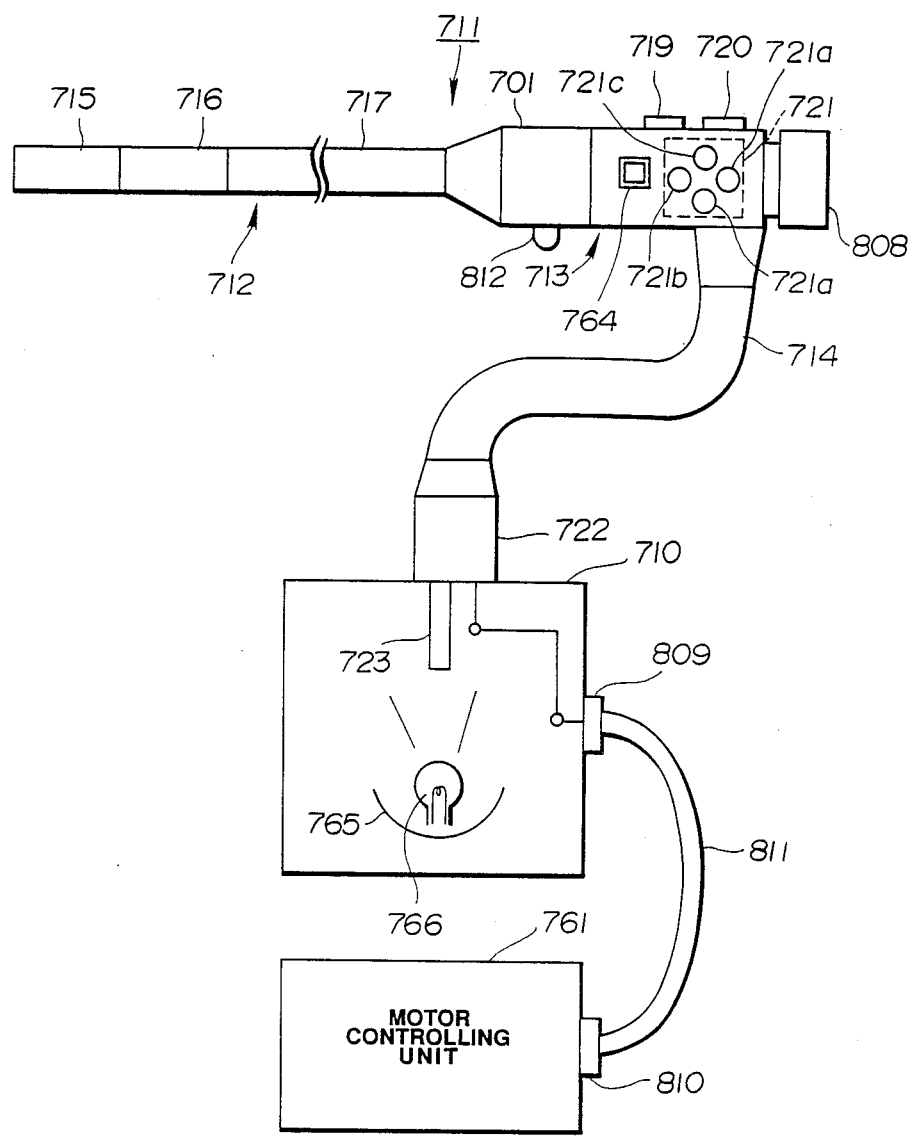
FIGS. 37 and 38 relate to the 13th embodiment of the present invention.
Figure 38:
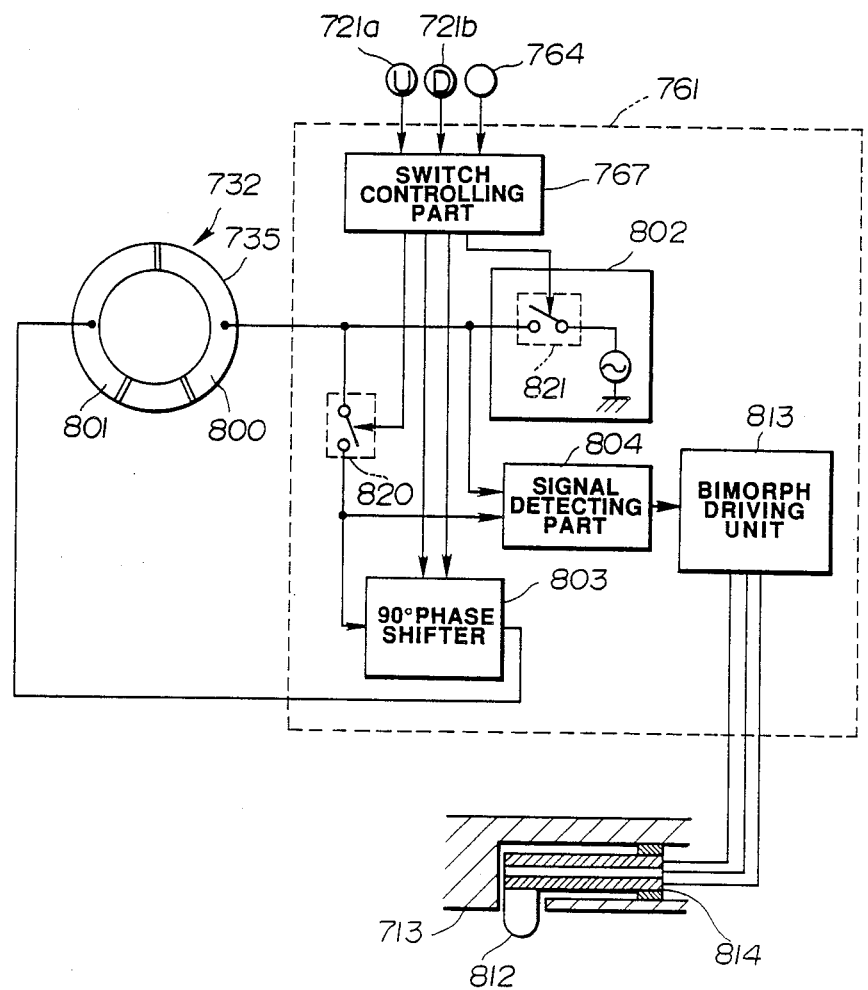

In FIGS. 37 and 38 is shown the 13th embodiment of the present invention.

FIG. 38 is a block diagram showing the formation of a circuit for detecting and reporting the driving state of the endoscope bendable part in the vertical direction. The formation of the circuit for detecting and reporting the bending driving state in the horizontal state is the same and shall not be described here. The same components as in the 11th embodiment shall bear the same reference numerals and shall not be described here.

As shown in FIG. 37, in this embodiment, the present invention is applied to an endoscope 711 using an image guide fiber bundle. The above mentioned endoscope 711 is provided in a tip forming part 715 with an objective lens not illustrated. The entrance end surface of the image guide fiber bundle provided within an insertable part 712 and operating part 713 is arranged in the image forming position of this objective lens. An eyepiece part 808 is provided at the rear end of the operating part 713. The exit end surface of the above mentioned image guide fiber bundle is arranged as opposed to an eyepiece not illustrated provided in the eyepiece part 808 so that the image of such object to be imaged as a body cavity interior may be observed with a naked eye or the like through the eyepiece.

Also, the above mentioned operating part 713 is provided with the free switch 764 provided in the light source apparatus 760 in the 11th embodiment and is further internally provided with a bimorph 814 for having the operator recognize that a standing wave is produced in a later described oscillating wave motor. An oscillator 812 fitted to the oscillating part of this bimorph 814 projects out of the sheath of the operating part 713.

A light source unit 710 feeding a light source to the above mentioned endoscope 711 and a motor controlling unit 761 driving and controlling the oscillating wave motor provided within the operating part are connected with each other through a cable 811 provided at the ends with connectors 809 and 810 and are to be connected with the endoscope 711 through a connector 722 of the endoscope 711 connected to a light source unit 710.

In this embodiment, the control of the oscillating wave motor 732 and the means for detecting that a standing wave is produced in the oscillating wave motor are the same as in the 11th embodiment. The driving voltage applied to the electrodes 800 and 801 provided in the piezoelectric body 735 of the oscillating wave motor 732 is detected by the signal detecting part 804 and the bimorph driving unit 813 is controlled by this detected signal. In case a standing wave is produced in the oscillating wave motor, that is, in case the bendable part 716 is free, the bimorph driving unit 813 will oscillate and drive the bimorph 814 so that the oscillator 812 may oscillate and, by this oscillation, the operator may recognize that the bendable part is free.

In this embodiment, by being notified by the oscillation that the bendable part 716 is free, the operator can recognize it by the body feel.

By the way, in the 11th to 13th embodiments, the means of detecting the driving voltage applied to the oscillating wave motor has been explained but a means of detecting the driving current flowing into the oscillating wave motor may be used.

Further, the notifying means may be of a combination of the 11th to 13th embodiments. For example, such displaying means as an LED may be provided in the operating part.

Also, in the endoscope having an eyepiece part, such displaying means as, for example, an LED may be provided within the above mentioned eyepiece part and a signal detecting part may be provided in the operating part.

Further, this embodiment can be adapted not only to a proceeding wave type oscillating wave motor but also to a composite oscillator type oscillating wave motor.

For example, for a combination of a DC motor and electromagnetic clutch, the control signal of the electromagnetic clutch or the like may be made an input signal of the signal detecting part.

Figure 39:
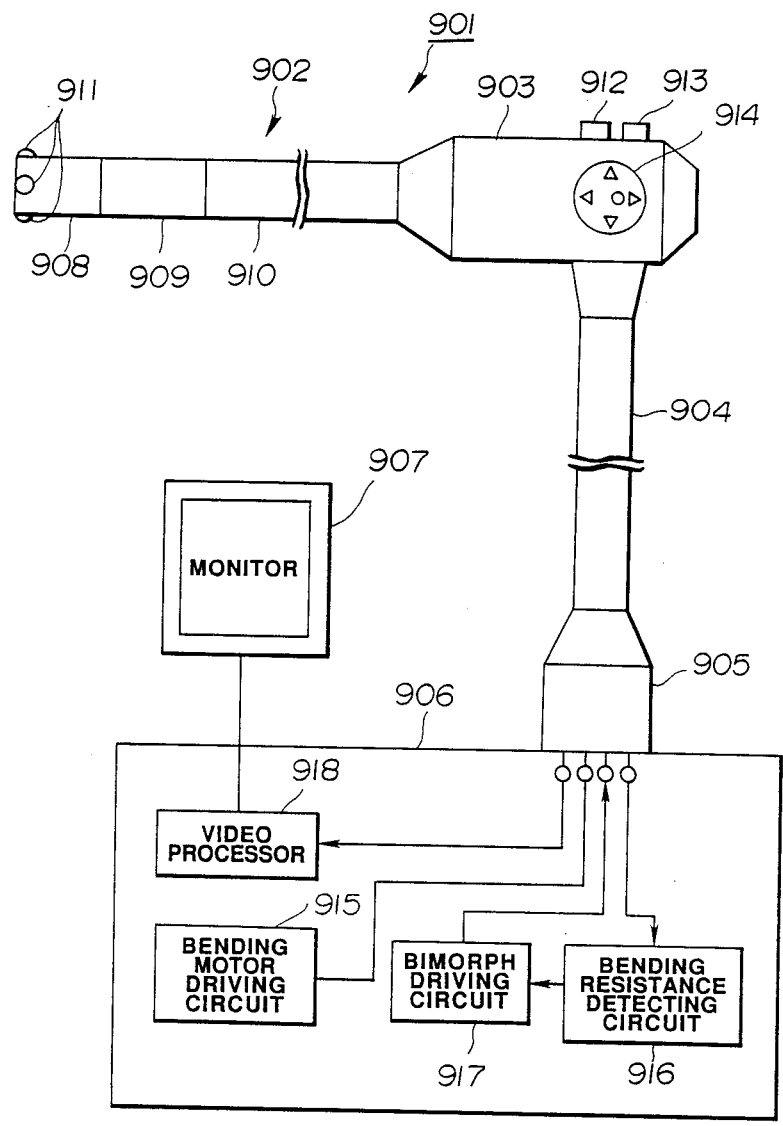
FIGS. 39 and 40 relate to the 14th embodiment of the present invention.
Figure 40:
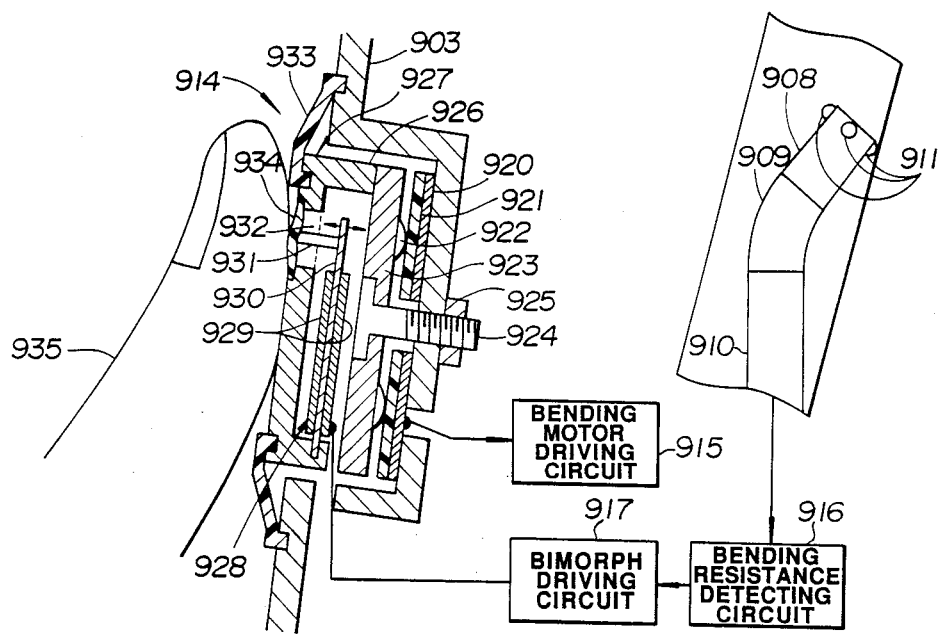

In FIGS. 39 and 40 is shown the 14th embodiment of the present invention.

As shown in FIG. 39, the electronic endoscope apparatus comprises an endoscope 901 formed to be elongate so as to be insertable, for example, into a body cavity, a light source apparatus 906 provided with a later described video processor 918 and connected with a universal cord 904 of the above mentioned endoscope 901 by a connector 905 and a monitor 907 displaying such object to be imaged as a part within a body cavity by an output signal of the above mentioned video processor 918.

The above mentioned endoscope 901 comprises an elongate insertable part 902, a thick operating part 903 connected to this insertable part at the rear end, a universal cord 904 extended sidewise out of this operating part 904 and a connector 905 provided at the end of this universal cord 904. The above mentioned insertable part 902 comprises a tip forming part 908 provided with a pressure detecting device 911 for detecting the contact pressure, the exit end surface of a light guide not illustrated and an imaging device for imaging an object to be imaged, a vertically/horizontally bendable part 909 connected to this tip forming part 908 at the rear end and a flexible tube part 910 connected to this bendable part 909 at the rear end.

The above mentioned operating part 903 is provided internally with a motor not illustrated for bending and driving the bendable part 909, an air and water feeding switch 912, a sucking switch 913 and a bending switch outputting a control signal for controlling the above mentioned motor and internally provided with a later described bimorph.

The above mentioned light guide is provided within the insertable part 902, operating part 903 and universal cord 904 and projects on the entrance end surface out of the connector 905.

The above mentioned light source apparatus 906 is provided with a light source unit not illustrated for feeding an illuminating light to the light guide not illustrated provided within the above mentioned endoscope 901 and projecting out of the connector 905, a bending motor driving circuit 915 driving the above mentioned motor by the control signal of the above mentioned bending switch, a bending resistance detecting circuit 916 processing the pressure signal from the above mentioned pressure detecting device 911, a bimorph driving circuit 917 driving a bimorph provided within the above mentioned bending switch 914 and a video processor 918 converting and variously processing the imaging signal from the imaging device arranged in the above mentioned tip forming part 908 and outputting it as a video signal to the above mentioned monitor 907.

In the above mentioned bending switch 914, as shown in FIG. 40, a substantially circular recess is formed in the operating part 903, a substrate 920 in which comb-like electrodes are formed at intervals of 90 degrees on the same periphery is fixed as by bonding to the bottom of the above mentioned recess, such conductive member as, for example, a conductive rubber 921 is arranged on this substrate 920 and a later described pad 927 above this conductive rubber 921 is fixed to the operating part by such force as will not make the above mentioned conductive rubber 921 conductive with a fixing bolt 924 and nut 925 arranged on the above mentioned pad 927.

The above mentioned pad 927 is formed of a substantially disc-like lower pad 923 positioned on the above mentioned recess side and an upper pad 926 positioned on the sheath side of the above mentioned operating part 903, The above described fixing bolt 924 is arranged substantially in the center of the above mentioned lower pad 923. Further, projections 922 are provided at intervals of 90 degrees in the positions on the above described comb-like electrodes on the above mentioned conductive rubber 921 side.

The above mentioned upper pad 926 has a space between it and the above mentioned lower pad 927. A hole 932 is made in the part positioned on the sheath side of the above mentioned operating part of the above mentioned upper pad 926 and is sealed with a rubber cover 934 on the sheath side of the above mentioned operating part 903. Further, a later described bimorph 928 embedded at one end is arranged in the above described space between the upper pad 926 and lower pad 923.

In the above mentioned bimorph 928, piezoelectric bodies 929 are pasted to both surfaces of a substantially plate-like elastic plate 930 which is embedded at one end in the above mentioned pad 926 and has at the other end a pin 931 erected so as to pass through the above mentioned hole 932 so that the above mentioned bimorph 928 may oscillate at the other end as shown by the arrow with one end embedded in the above mentioned pad 926 as a fulcrum.

The upper pad 926 of the above mentioned pad 927 and the sheath of the above mentioned operating part 903 are bridged with each other by a rubber cover 933.

The bending switch 914 and operating part 903 are made water-tight by the above mentioned rubber covers 933 and 934.

The operation of the thus formed electronic endoscope apparatus shall be explained.

In the electronic endoscope apparatus, as shown in FIG. 39, when the endoscope 901 is connected to the light source apparatus 906 by the connector 905, the light source unit not illustrated and the entrance end surface of the light guide not illustrated will be opposed to each other and the bending motor driving circuit 915, bending resistance detecting circuit 916, bimorph driving circuit 917 and video processor 918 will be connected with the endoscope 901.

Further, when a power source is input into the light source apparatus 906, an illuminating light from the above mentioned light source unit will be fed to the above mentioned light guide on the entrance end surface, will be led through the above mentioned light guide and will be radiated to a part within a body cavity or the like from the exit end surface of the tip part 908. The image of the object irradiated with this illuminating light will be formed on the photoelectric converting surface of the solid state imaging device not illustrated by the objective lens not illustrated arranged in the tip part 908, will become a photoelectrically converted signal and will be input into the video processor 918, will be converted to a video signal and variously processed by the above mentioned video processor 918 and will be displayed in the above mentioned monitor 907.

In the case of operating the bendable part 909 to be bent, as shown in FIG. 40, when the upper pad 926 of the bending switch 914 is pushed in a predetermined direction with the face of a finger 935, the projections 922 arranged on the lower pad 923 will press the conductive rubber 921. Thereby, the conductive rubber 921 will vary in the resistance value in response to this pressing and the variation of this resistance value will be transmitted to the bending motor driving circuit 915 through the comb-like electrode formed on the substrate 920. The bending motor driving circuit 915 will judge the bending direction of the bendable part 909 by the comb-like electrode whose resistance value has varied and the driving speed by the resistance value and will drive the bending motor not illustrated. By the operation of this bending motor, the bendable part 909 will bend in the predetermined direction and the tip part 908 will be directed in the predetermined direction.

Here, in case the tip part 908 contacts such part to be inspected as the body cavity wall, the pressure detecting device 911 will output to the bending resistance detecting circuit 916 the above mentioned contact pressure as an electric signal of the resistance value variation or electromotive force. In case this electric signal is judged to be an electric signal higher than the predetermined contact pressure, for example, the contact pressure set freely by the operator, the bending resistance detecting circuit 916 will output a control signal to the bimorph driving circuit 917. By this control signal, the bimorph driving circuit 917 will output a driving signal to the bimorph 928. By this driving signal, the bimorph 928 will oscillate with one end embedded in the upper pad 926 as a fulcrum and the pin 931 will move in response to the above mentioned oscillation and will sting the face of the finger 935 of the operator through the rubber cover 934.

By the above described operation, the tip part 908 of the endoscope 901 will contact such part to be inspected as the body cavity wall. There is an effect that, in case the contact pressure becomes higher than the predetermined value, the operator will be able to recognize the above mentioned state by the bending switch 914.

Figure 41:
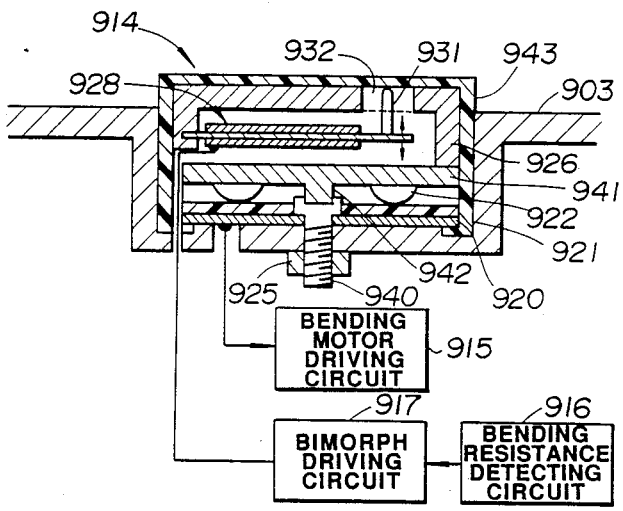
FIG. 41 relates to the 15th embodiment of the present invention.

In FIG. 41 is shown the 15th embodiment of the present invention.

By the way, the electronic endoscope apparatus in this embodiment is the same as in the 14th embodiment. The same components as in the 14th embodiment shall bear the same reference numerals and shall not be explained here.

As shown in FIG. 41, a lower pad 941 of a bending switch 914 in this embodiment is formed to be substantially disc-like and projections 922 are provided on the above described conductive rubber 921 side of the above mentioned lower pad 941. Further, in this lower pad 941, a bar-like projection 942 is formed substantially in the center so as to project on the surface in the same direction as of the above mentioned projection 922. By varying the diameter and length of this bar-like projection 942, the stroke (inclination when pushed down) of the bending switch 914 can be varied. A fixing bolt 940 is formed to have a recess so as to engage in the upper part with the above mentionend bar-like projection 942 and is arranged substantially in the center of a substrate 920.

Further, a rubber cover 943 is applied to cover the above described upper pad 926, lower pad 941, conductive rubber 921 and substrate 920 and is formed to be turned at the end on the side opposite the conductive rubber on the outer periphery of the substrate 920.

The thus formed bending switch 914 is fixed in the recess of the above described operating part 903 with the fixing bolt 940 and nut 925. Further, the rubber cove 943 is also fixed by being held between the substrate 920 and the sheath of the operating part 903.

By the way, the rubber cover 943 is fixed as by bonding at the end on the side opposite the conductive rubber 921 on the outer periphery of the substrate 920 and then may be fixed in the recess of the operating part 903 with the fixing bolt 940 and nut 025.

The operation in this embodiment is the same as in the 14th embodiment. When the upper pad 926, lower pad 941, conductive rubber 921 and substrate 920 are formed integrally with the rubber cover 943, the rubber cover 943 will act as a packing between the bending switch 914 and operating part 903 and there will be an effect that the water-tightness will improve.

The other effects are the same as in the 14th embodiment.

Figure 42:
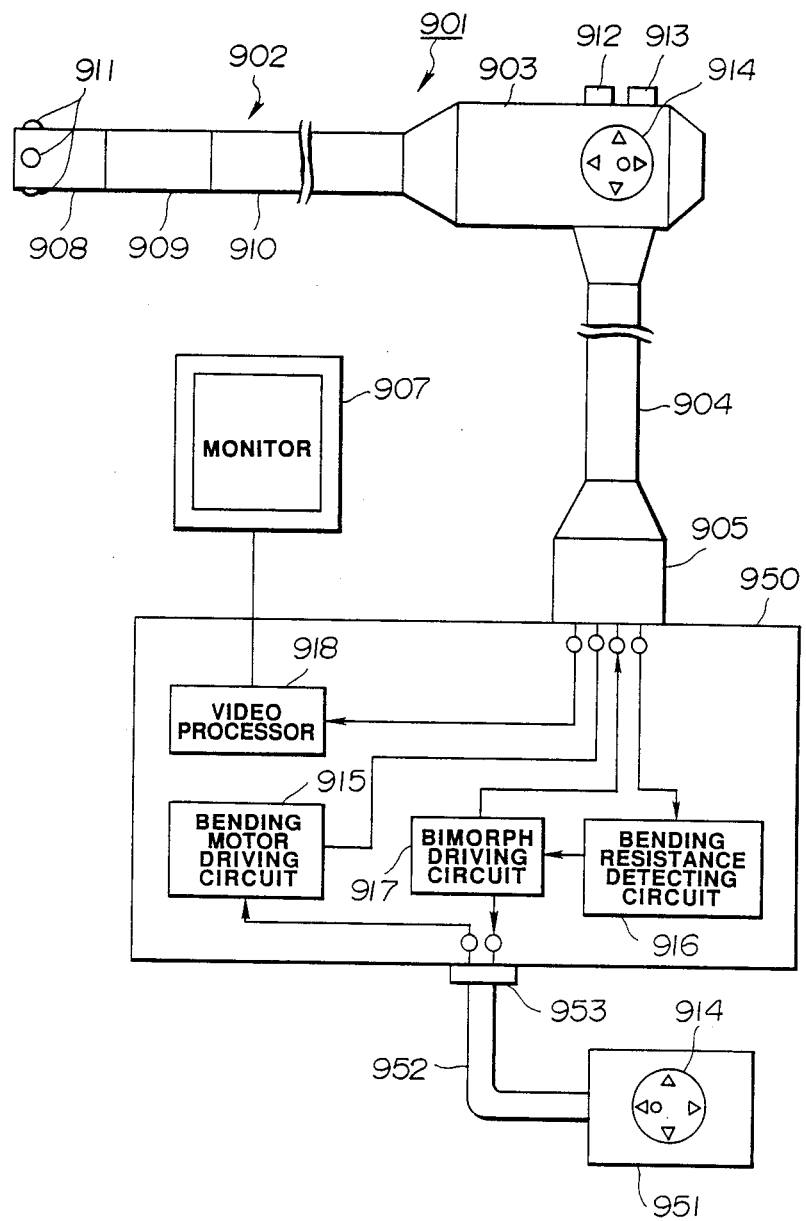
FIG. 42 relates to the 16th embodiment of the present inventiion.

In FIG. 42 is shown the 16th embodiment of the present invention.

By the way, the same components as in the 14th and 15th embodiments shall bear the same reference numerals and shall not be explained here.

As shown in FIG. 42, the light source apparatus 950 in this embodiment is of a formation in which a bending remote control 951 can be connected to the light source apparatus 906 of the 14th embodiment.

The above mentioned bending remote control 951 is provided with the above described bending switch 914. A connecting cord 952 is extended and is provided at the end with a connector 953.

The above mentioned bending remote control 951 is connected with the light source apparatus 950 by a connector 953 and is to be connected with a bending motor driving circuit 915 and bimorph driving circuit 917 provided in the light source apparatus 950.

The bending switch 914 provided in the bending remote control 951 may be the one explained in the 15th embodiment.

The operation in this embodiment is the same as in the 14th and 15th embodiments.

That is to say, there is an effect that, in case the tip part 908 of the endoscope 901 contacts such part to be inspected as the body cavity wall and the contact pressure has become higher than a predetermined value, the operator will be able to recognize the above mentioned state even by the bending switch 914 provided in the bending remote control.

The other effects are the same as in the 14th and 15th embodiments.

Figure 43:
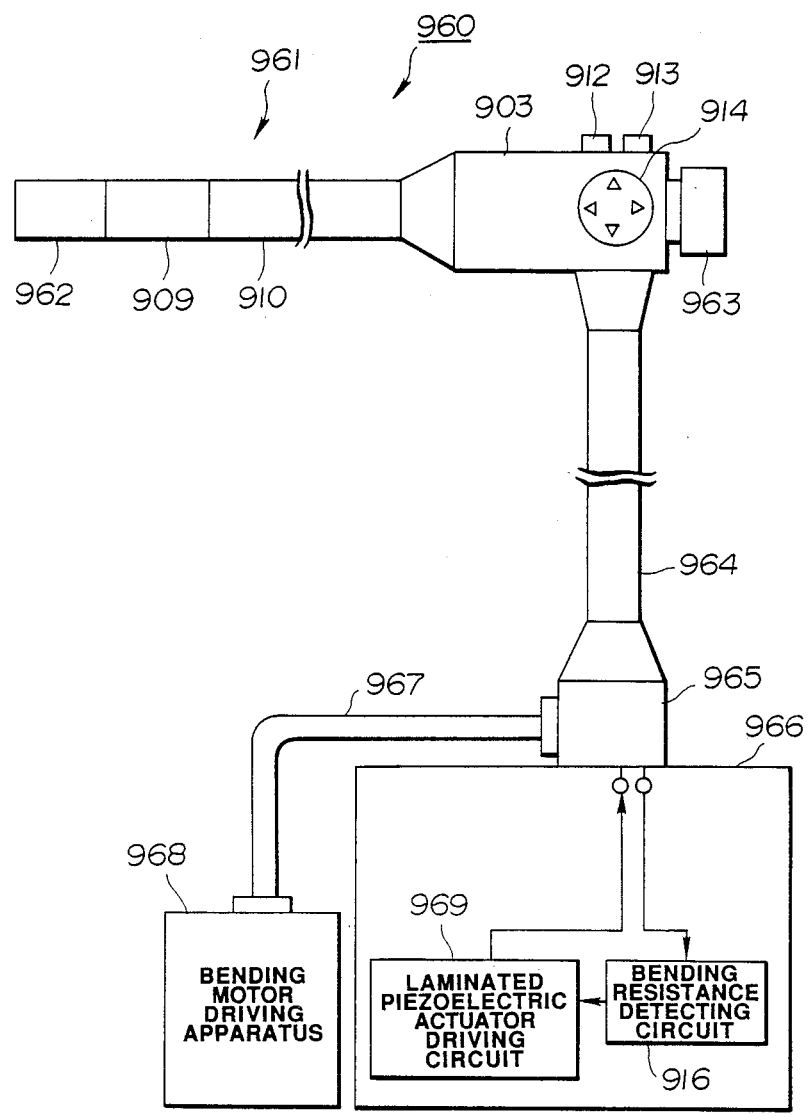
FIGS. 43 to 45 relate to the 17th embodiment of the present invention.
Figure 44:
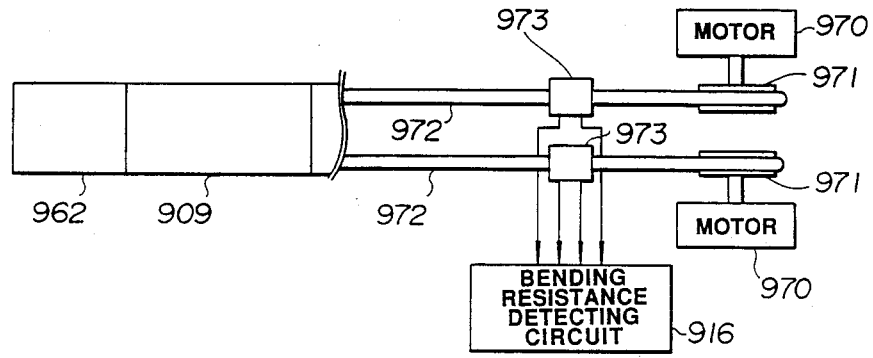
Figure 45:
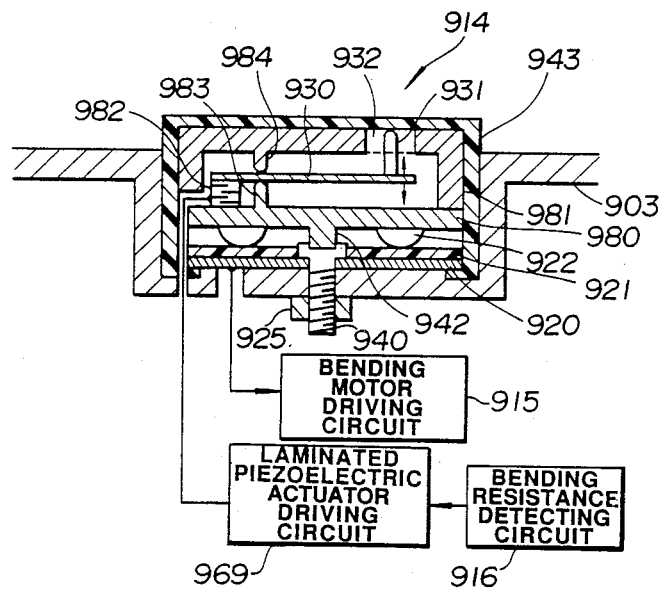

In FIGS. 43 to 45 is shown the 17th embodiment of the present invention.

By the way, the same components as in the 14th to 16th embodiments shall bear the same reference numerals and shall not be explained here.

As shown in FIG. 43, the endoscope apparatus comprises an endoscope 960 which is a fiber scope formed to be elongate so as to be insertable, for example, into a body cavity, a later described light source apparatus 966 to which a universal cord 964 of the above mentioned endoscope 960 is connected by a connector 965 and a later described bending motor driving apparatus 968 connected by a connecting cable 967 extended to the above mentioned connector 965.

The above mentioned endoscope 960 comprises an elogate insertable part 961, a thick operatig part 903 connected to this insertable part 961 at the rear end, an eyepiece part 963 provided at the rear end of this operating part 903, the universal cord 964 extended sidewise of the above mentioned operating part 903, a connector 965 provided on this universal cord at the end and the connecting cable 967 extended sidewise out of this connector 965.

The above mentioned insertable part 961 comprises a tip forming part 962 in which the exit end surface of the above described light guide and the entrance end surface of a later described image guide are arranged, a bendable part 909 connected to this tip forming part at the rear end and a flexible tube part 910 connected to this bendable part 909 at the rear end.

The above mentioned light guide is provided within the insertable part 961, operating part 903 and universal cord 964 and projects on the entrance end surface out of the connector 965.

The above mentioned image guide is provided within the insertable part 961 and operating part 903 and is opposed on the exit end surface to an eyepiece not illustrated arranged in the above mentioned eyepiece part 963.

The above mentioned light source apparatus 966 is provided with a light source unit not illustrated for feeding an illuminating light to the light guide not illustrated provided within the above mentioned endoscope 960 and projecting out of the connector 965, a bending resistance detecting circuit 916 and a laminated actuator driving circuit 969 driving a laminated actuator provided within a later described bending switch 914.

The above mentioned bending motor driving apparatus 968 is provided with a bending motor driving circuuit driving the bending motor with a control signal of the bending switch 914.

As shown in FIG. 44, the above mentioned bendable part 909 is to be bent vertically/horizontally by pushing and pulling bending wires 972 wound on pulleys 971 fitted and fixed to the shafts of motors 970.

Stress detecting devices 973 for detecting the stresses of the above mentioned bending wires 972 are provided, for example, near the pulleys 971 of the above mentioned bending wires 972 and are connected at the signal ends to a bending resistance detecting circuit 916.

As shown in FIG. 45, the lower pad 980 of the bending switch 914 in this embodiment is formed to be substantially disc-like and is provided with projections 922 on the above described conductive rubber 921 side. Further, this lower pad 980 has a bar-like projection 942 formed substantially in the center to project on the surface in the same direction as of the above mentioned projections 922, a laminated actuator 982 fixed, for example, by bonding at one end to the pheripheral part on the surface opposite this bar-like projection 942 and a supporting part 983 formed near the laminated actuator 982.

The upper pad 981 has a space between it and the above mentioned lower pad 980, is provided with a hole 932 in the part positioned on the sheath side of the above mentioned operating part 903 of the above mentioned pad 981 and has a supporting part 984 formed to be opposed to the supporting part 983 of the lower pad 980.

The above mentioned laminated actuator 982 has at the other end an elastic plate 930 fixed, for example, by bonding at one end. The elastic plate 930 has at the other end a pin 931 erected.

Further, a rubber cover 943 is applied to cover the above described upper pad 81, lower pad 980, conductive rubber 921 and substrate 920 and is formed to be turned at the end on the side opposite the conductive rubber 921 on the outer periphery of the substrate 920.

The thus formed bending switch 914 is fixed to the recess of the above described operating part 903 with a fixing bolt 940 and nut 925. Further, the rubber cover 943 is also fixed as held between the substrate 920 and the sheath of the operating part 903.

The operation of the thus formed endoscope apparatus shall be explained.

The illuminating light from the above mentioned light source unit will be led by the above mentioned light guide and will be radiated to such part as is within a body cavity from the exit end surface of the tip part 962. The image of the object to be imaged erradiated with this illuminating light will be formed on the entrance end surface of the above mentioned image guide by the objective lens not illustrated arranged in the tip part 962, will be led through the above mentioned image guide and will be observed by a naked eye or the like with an eyepiece not illustrated arranged as opposed to the exit end surface of the above mentioned image guide in the eyepiece part 963.

In the case of bending operating the bendable part 909, when the bending switch 914 is operated, a driving power will be fed to the motors 970 shown in FIG. 44 from the bending motor driving apparatus and the motors 970 will rotate. The pulleys 971 will rotate in response to the rotation of these motors 970 to push and pull the bending wires 972 wound on the above mentioned pulleys 970 so as to bend the bendable part 909 vertically/horizontally. The stresses, that is, bending resistances on these bending wires 972 will be made such electric signals as of the resistance value variations or electromotive forces by the stress detecting device 973 and will be input into the bending resistance detecting circuit 916.

Here, in case the tip part 962 contacts a body cavity wall or the like, when the stress, that is, bending resistance applied to the bending wire 972 increases and is judged to be a bending resistance higher than a predetermined bending resistance, for example, than a bending resistance freely set by the operator, the bending resistance detecting circuit 916 will output a control signal to the laminated actuator driving circuit 969 shown in FIG. 45. With this control signal, the laminated actuator driving circuit 969 will output a driving signal to the laminated actuator 982. With this driving signal, the laminated actuator 982 will oscillate and the pin 931 will be moved in esponse to the above mentioned oscillation by the elastic plate 930 supported by the supporting parts 983 and 984 and will sting the face of the finger of the operator through the rubber cover 943.

In this embodiment, there is an effect that the present invention can be adapted even to an endoscope difficult to arrange the pressure detecting device in the tip part 962.

The other effects are the same as in the 14th to 16th embodiments.

Figure 46:
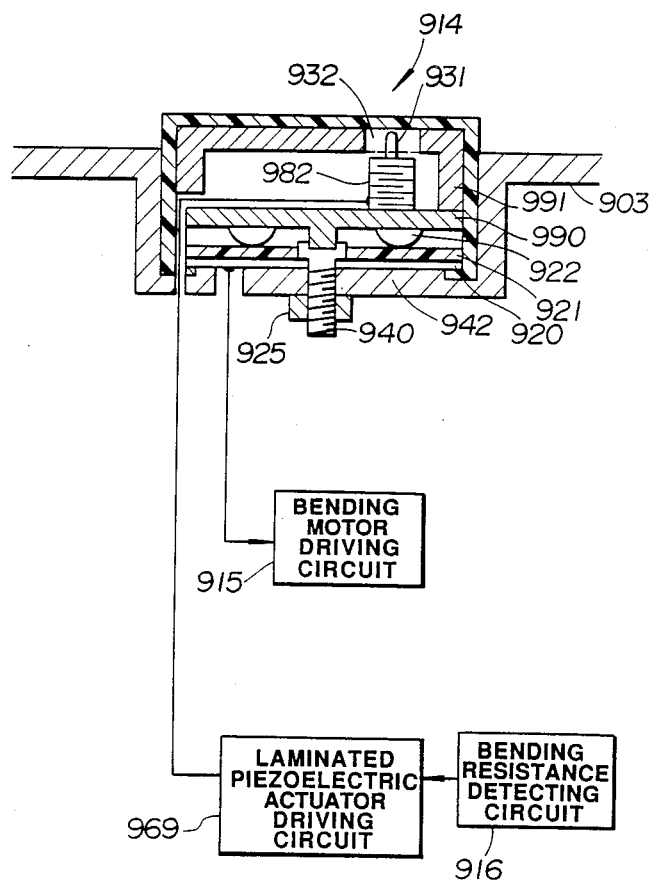
FIG. 46 relates to the 18th embodiment of the present invention.

In FIG. 46 is shown the 18th embodiment of the present invention.

By the way, the same components as in the 14th to 17th embodiments shall bear the same reference numerals and shall not be explained here.

As shown in FIG. 46, the lower pad 990 of the bending switch 914 in this embodiment is formed to be substantially disc-like, is provided with projections 922 on the above described conductive rubber 921 side, has a bar-like projection 942 formed substantially in the center to project on the surface in the same direction as of the above mentioned projections 922 and is provided on the surface opposite the above mentioned bar-like projectin 942 with the laminated actuator 982, for example, by boding at one end.

The upper pad 991 has a space between it and the above mentioned lower pad and is provided with a hole 932 in the part opposed to the above mentioned laminated actuator 982 and positioned on the sheath side of the above mentioned operating part.

Further, a rubber cover 943 is applied to cover the above described upper cover pad 981, lower pad 980, conductive rubber 921 and substrate 920 and is formed to be turned at the end on the side opposite the conductive rubber 921 on the outer periphery of the substrate 920.

By the way, the upper pad 991 and lower pad 990 may be made a pad of one member having a recess formed and provided in the above mentioned recess with the above mentioned laminated actuator 982.

In this embodiment, there is an effect that the oscillation of the laminated actuator 982 can directly sting the face of the finger of the operator through the rubber cover 943.

The other effects are the same as in the 14th to 17th embodiments.

By the way, in the 14th to 18th embodiment, the form of the bending switch may be cruciform or polygonal instead of being circular.

Also, the means of stinging the operator with the oscillation may vary the amplitude of the oscillation in response to the contact pressure or bending resistance.

By the way, in the case of making the pressure detecting device a means of detecting the bending resistance, the above mentioned pressure detecting device may be used as one of the members forming the endoscope tip forming part and the above mentioned pressure detecting devices may be provided on all the peripheral surface on the outer periphery of the endoscope tip forming part.

Also, in the oscillating wave motor, the means of detecting the bending resistance may be a means of detecting it by the voltage of the driving power and the phase difference of the current.

Further, the means of detecting the bending resistance may be a means wherein, for example, a photoreflector is provided on a pulley or the like and the driving power and the rotation amount of the above mentioned pulley are compared and detected by an operation process.

The notifying means may be used in common with an outside displaying apparatus or warning apparatus.

Figure 47:
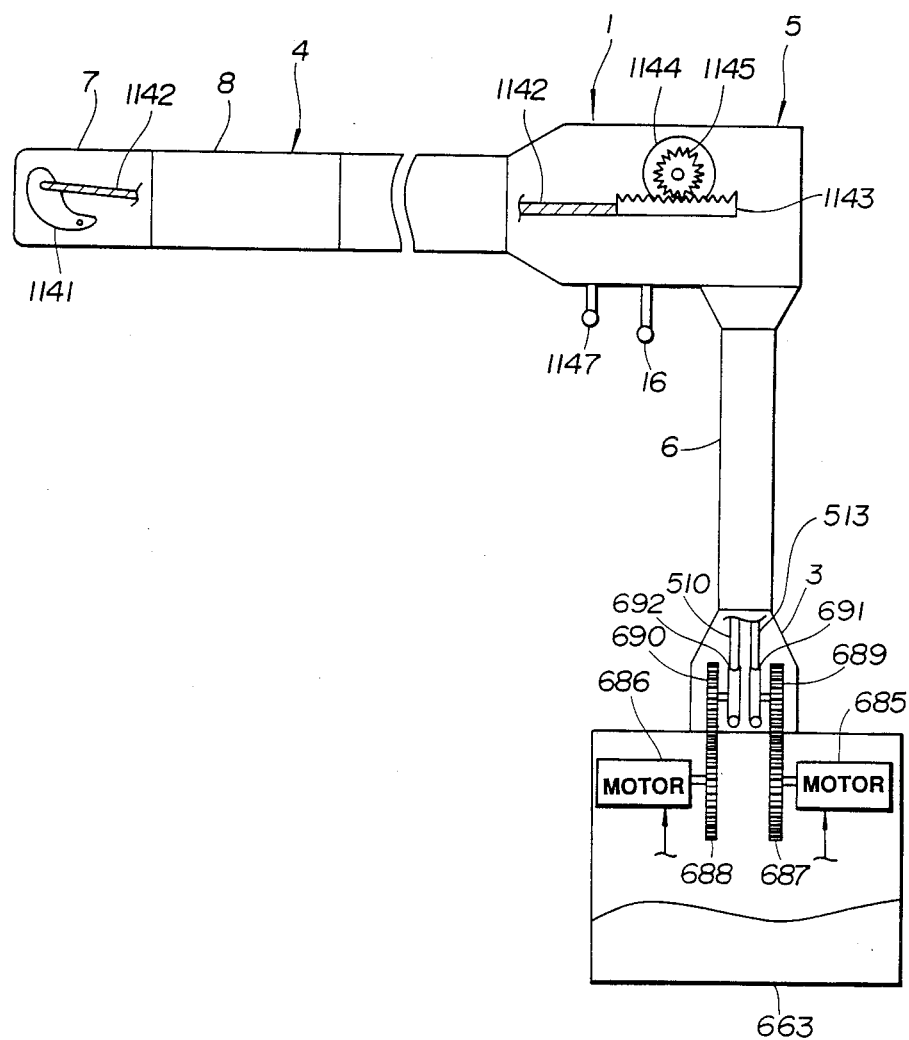
FIGS. 47 and 48 relate to the 19th embodiment of the present invention.
Figure 48:
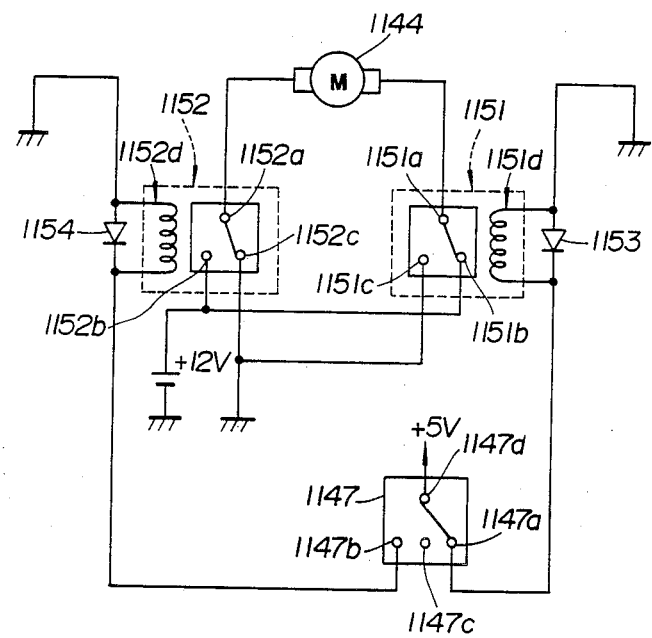
Figure 49:
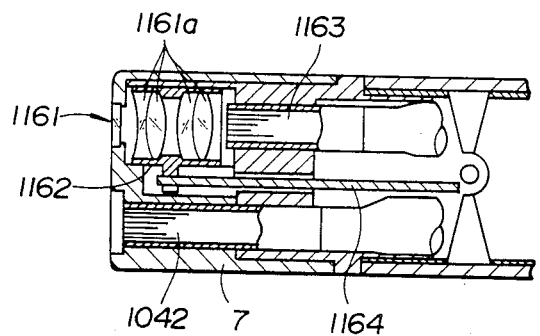
FIG. 49 relates to a modification of the 19th embodiment.

FIGS. 47 to 49 relate to the 19th embodiment of the present invention. FIG. 47 is an explanatory view showing the formation of the essential part of an endoscope apparatus. FIG. 48 is a circuit diagram showing a DC motor driving system. FIG. 49 is an explanatory view showing a tip part of an insertable part of an endoscope in a modification of this embodiment.

As shown in FIG. 47, the same as in the first embodiment, the endoscope 1 in this embodiment has an insertable part 4, operating part 5, universal cord 6 and connector 3 which is to be connected to the same bending controlling apparatus 663 as in the third embodiment. The same as in the ninth embodiment, gears 689 and 690 and pulleys 691 and 692 are provided within the connector 3 and bending wires 510 and 513 are fitted respectively to the above mentioned pulleys 691 and 692.

Also, a treating instrument channel not illustrated is provided within the insertable part 4 in this embodiment and a treating instrument raising stand 1141 for raising on the tip side the treating instrument inserted through the above mentioned treating instrument channel is provided within the tip part 7. A treating instrument raising wire 1142 for rotating this treating insatrument raising stand 1141 is fixed at the tip to this treating instrument raising stand 1141, is inserted through the insertable part 4 and is fitted at the rear end to a rack gear 1143 provided within the operating part 5. A pinion 1145 fitted to the output shaft of a DC motor 1144 provided within the operating part 5 meshes with this rack gear 1143.

A bending switch 16 for the bending operation and a treating instrument raising switch 1147 are provided on the operating part 5.

The formation of the above mentioned DC motor 1144 driving system shall be explained with reference to FIG. 48.

The DC motor 1144 is connected at one input end to a relay 1151 at a movable contact ll51a and is connected at the other input end to a relay 1152 at a movable contact 1152a. A power source voltage (+12V) is applied to the above mentioned relays 1151 and 1152 respectively at fixed contacts ll51b and 1152b on one side and the above mentioned relays 1151 and 1152 are earthed respectively at the other fixed contacts 1151c and 1152c. Also, the electromagnetic coil 1151d of the relay 1151 is connected at one end to the above mentioned treating instrument raising switch 1147 at a fixed contact 1147a and to a diode 1153 at the cathode, is earthed at the other end and is connected to the above mentioned diode 1153 at the anode. In the same manner, the electromagnetic coil 1152d of the relay 1152 is connected at one end to the above mentioned treating instrument raising switch 1147 at a fixed contact 1147b and to a diode 1154 at the cathode, is earthed at the other end and is connected to the above mentioned diode 1154 at the anode. Nothing is connected to the above mentioned treating instrument raising switch 1147 at another fixed contact 1147c. A power source voltage (+5V) is applied to the above mentioned treating instrument raising switch 1147 at a movable contact 1147d.

The operation of this embodiment shall be explained in the following.

When the movable contact 1147d of the treating instrument raising switch 1147 is connected to the fixed contact 1147a, an electric current will flow to the electromagnetic coil 1151d of the relay 1151, the movable contact 1151a and fixed contact 1151b will be connected with each other, no current will flow to the electromagnetic coil 1152d of the relay 1152 and the movable contact 1152a and fixed contact 1152c will be connected with each other. Therefore, a power source voltage will be applied to the DC motor 1144 at one input end and the DC motor 1144 will be earthed at the other input end. On the contrary, when the movable contact 1147d of the treating instrument raising switch 1147 is connected to the fixed contact 1147b, the movable contact 1151a and fixed contact 1151c of the relay 1151 will be connected with each other, the movable contact 1152a and fixed contact 1152b of the relay 1152 will be connected with each other, the DC motor 1144 will be earthed at one input end and a power source voltage will be applied to the DC motor 1144 at the other input end. When the movable contact 1147 of the treating instrument raising switch 1147 is thus selectively connected to one of the fixed contacts 1147b and 1147c, the DC motor 1144 will rotate normally or reversely. Also, when the movable contact 1147d of the treating instrument raising switch 1147 is connected to the fixed contact 1147c, the DC motor 1144 will stop. Thus, the treating instrument raising wire 1142 will be pushed or pulled and the treating instrument raising stand 1141 will be rotated.

Thus, in this embodiment, bending motors 685 and 686 are provided in a bending controlling apparatus 663 outside the endoscope 1 and a treating instrument raising DC motor 1144 is provided within the operating part 5. Therefore, while preventing the reduction of the responsibility on the treating instrument, the treating instrument raising operation can be electrically made and, by providing the bending motors 685 and 686 outside the endoscope 1, the operating part 5 can be prevented from being made large.

FIG. 49 shows a modification of this embodiment in which the focus of the objective lens system is electrically adjusated. As shown in FIG. 49, an objective lens system 1161 is provided within the tip part 7 and at least a part of lenses 1161a of this objective lens system 1161 is held in a lens barrel 1162 movable in the optical axial direction. The focus can be adjusted by moving the lenses 1161a in the optical axial direction. The tip surface of an image guide 1163 or a solid state imaging device is arranged in the image forming position of the above mentioned objective lens system 1161. A focus adjusting wire 1164 is fixed at the tip to the above mentioned lens barrel 1162, is inserted through the insertable part 4 and is fitted at the rear end to the rack gear 1143 provided within the operating part 5 shown in FIG. 47. The other formations are the same as in the case of the treating instrument raising shown in FIGS. 47 and 48. By the way, the reference numeral 1042 represents a liht guide transmitting an illuminating light. The switch 1147 in FIGS. 47 and 48 shall be a fucus adjusting switch.

In this modification, by operating the above mentioned switch 1147, the DC motor 1144 can be rotated normally and reversely or stopped and the lenses 1161a can be moved in the optical axial direction to adjust the focus.

According to this modification, while preventing the reduction of the responsibility of the focus adjustment, the focus can be electrically adjusted and, by providing the bending motors 685 and 686 outside the endoscope 1, the operating part 5 can be prevented from being made large.

The other formations, operations and effects of this embodiment and its modification are the same as in the third embodiment.

By the way, the present invention can be applied not only to an electronic endoscope provided with a solid state imaging device in the tip part of the insertable part but also to an endoscope of the type that an object image formed by an objective lens is transmitted to the base side of the insertable part through an image guide and is observed by a naked eye in the eyepiece part or is imaged by an imaging means.

The present invention can be applied not only to an oscillating wave motor but also to such electromagnetic motor as a stepping motor, DC motor or AC motor.

Further, the present invention can be applied not only to an endoscope apparatus used for medical purposes but also to an endoscope apparatus used, for example, for industrial purposes.

As described above, according to the present invention, there are such effects that, in case the bendable part of an endoscope strongly contacts such part to be inspected as a body cavity interior, the bendable part will be able to be operated so as to avoid the contact, a safe diagnosis or inspection will be able to be made, the operator will be able to have the bendable part at a predetermined bending angle which is substantially straight without requiring a skill, the inserting operation will be easy and the operatability will improve.

It is apparent that, in the present invention, working modes different in a wide range can be formed on the basis of this invention without deviating from the spirit and scope of the invention. This invention is not restricted by its specific working mode except being limited by the appended claims.

What is claimed is:

1. An endoscope apparatus comprising:
   an endoscope having an elongate insertable part having a bendable part and a driving means for bending and driving said bendable part;
   a first bending controlling means for controlling said driving means; and
   a second bending controlling means for controlling said driving means independently of said first bending controlling means when said first bending controlling means is controllable.

2. An endoscope apparatus comprising:
   an endoscope having an elongate insertable part having a bendable part and a driving means for bending and driving said bendable part;
   a first bending controlling means for controlling said driving means;
   a second bending controlling means for controlling said driving means independently of said first bending controlling means when said first bending controlling means is controllable; and
   a bending resistance detecting means for detecting the bending resistance of said insertable part.

3. An endoscope apparatus comprising:
   an endoscope having an elongate insertable part having a bendable part and a driving means for bending and driving said bendable part;
   a first bending controlling means for controlling said driving means;
   a second bending controlling means for controlling said driving means independently of said first bending controlling means when said first bending controlling means is controllable; and
   a switch means for controlling said second bending controlling means.

4. An endoscope apparatus according to claim 1 wherein said driving means includes an oscillating wave motor.

5. An endoscope apparatus according to claim 1 wherein said driving means includes an electromagnetic motor.

6. An endoscope apparatus according to claim 1 wherein said second bending controlling means includes a means for controlling said bendable part so as to be of a predetermined bending angle with a predetermined time.

7. An endoscope apparatus according to claim 2 wherein said bending resistance detecting means includes a contact sensor provided at the tip of said insertable part.

8. An endoscope apparatus according to claim 2 wherein said bending resistance detecting means includes a contact sensor interposed by a bending wire connecting said bendable part and bending driving means with each other.

9. An endoscope apparatus according to claim 2 wherein said driving means includes an oscillating wave motor and said bending resistance detecting means includes a means for detecting the bending resistance by the difference of a phase angle of the voltage and current of an electric power fed to said oscillating wave motor.

10. An endoscope apparatus according to claim 2 wherein said driving means includes an electromagnetic motor and said bending resistance detecting means inclues a means for detecting the bending resistance from the power amount of the driving power fed to said electromagnetic motor.

11. An endoscope apparatus according to claim 2 further comprising a bending resistance reducing means for reducing the bending resistance on the basis of the output of said bending resistance detecting means.

12. An endoscope apparatus accoring to claim 11 further comprising a selecting means for selecting whether said bending resistance reducing means is to be used or not.

13. An endoscope apparatus according to claim 11 wherein said bending resistance reducing means inclues being selecated prior to said first bending controlling means.

14. An endoscope apparatus according to claim 11 wherein said driving means includes an oscillating wave motor and said bending resistance reducing means includes a control means for controlling said oscillating wave motor to be free.

15. An endoscope apparatus according to claim 14 wherein said oscillating wave motor is controlled to separate the rotor and stator from each other in case said oscillating wave motor is to be made free.

16. An endoscope apparatus according to claim 11 wherein said driving means includes an oscillating wave motor and said bending resistance reducing means includes a controlling means for generating a standing wave in said oscillating wave motor.

17. An endoscope apparatus according to claim 11 wherein said bending resistance reducing means includes a means for controlling said second bending controlling means to drive said driving means in the direction of reducing the bending resistance.

18. An endoscope apparatus according to claim 11 wherein said bending resistance reducing means includes a means for controlling a driving force transmitting means to be free.

19. An endoscope apparatus according to claim 18 wherein said transmitting meanns includes an electromagnetic clutch.

20. An endoscope apparatus according to claim 2 wherein said second bending controlling means includes a means for controlling said bendable part to of a predetermined bending angle by the control of said bending resistance detecting means.

21. An endoscope apparatus according to claim 20 wherein said predetermined bending angle is substantially straight.

22. An endoscope apparatus according to claim 20 further comprising at least one bending angle setting means for setting said predetermined bending angle.

23. An endoscope apparatus according to claim 3 wherein said second bending angle controlling means includes a means for controlling said bendable part to be of a predetermined bending angle at predetermined time intervals.

24. An endoscope apparatus according to claim 3 wherein said second bending controlling means includes a means for controlling said bendable part to be of a predetermined bending angle by the control of said switch means.

25. An endoscope apparatus according to claim 24 wherein said predetermined bending angle is substantially straight.

26. An endoscope apparatus according to claim 24 further comprising at least one bending angle setting means for setting said predetermined bending angle.

27. An endoscope apparatus according to claim 1 wherein said second bending controlling means is of the case that said driving means is controlled by said first bending controlling means and for controling said driving means.

28. An endoscope apparatus according to claim 6 wherein said second bending controlling means is for controlling said bendable part to be of a predetermined bending angle at a bending speed higher than the bending speed by said first bending controlling means.

29. An endoscope apparatus according to claim 6 wherein said second bending controlling means is for controlling said bendable part to be of a predetermined bending angle at a bending speed lower than the bending speed by said first bending controlling means.

30. An endoscope apparatus according to claim 2 wherein said second bending controlling means is controlled on the basis of the output from said bending resistance detecting means.

31. An endoscope apparatus according to claim 2 wherein said second bending controlling means will control said driving means even in case said first bending controlling means is controlling said driving means.

32. An endoscope apparatus according to claim 3 wherein said second control means will control said driving means even in case said first bending controlling means is controlling said driving means on the basis of the control of said switch means.

33. An endoscope apparatus according to claim 3 wherein said second control means will conntrol said driving means even in case said first bending controlling means is not controlling said driving means on the basis of the control of said switch means.

34. An endoscope apparatus comprising:
an endoscope having an elongate insertable part having a bendable part and a driving means for bending driving said bendable part;
a bending controlling means for controlling said driving means; and
a means for controlling said driving means so as to reduce a bending resistance to be at least lower than a predetermined value when said bending resistance of said insertable part reaches said predetermined value during the operation.

35. An endoscope bending driving controlling apparatus comprising:
a connecting means having a bending resistance detecting means for detecting the bending resistance of the insertable part and at least electrically connectable with an endoscope bent and driven by a driving means; and
a means for controlling said bending controlling means so as to reduce said bending resistance to be lower than at reast a predetermined value when the detected result of said bending resistance detecting means reaches said predetermined value during the operation.

36. An endoscope bending driving controlling apparatus according to claim 35 further internally provided with said driving means.

37. An endoscope bending driving controlling apparatus according to claim 35 wherein said endoscope is internally provided with said driving means.

38. An endoscope bending driving controlling apparatus according to claim 35 further comprising a light source means generating an illuminating light and feeding said illuminating light to said endoscope through said connecting means.

* * * * *